United States Patent
Weber et al.

(10) Patent No.: US 11,292,846 B2
(45) Date of Patent: Apr. 5, 2022

(54) BISPECIFIC ANTIBODIES BINDING ALK-1 AND BMPR-2

(71) Applicant: BAYER AKTIENGESELLSCHAFT, Leverkusen (DE)

(72) Inventors: Ernst Weber, Langenfeld (DE); Joerg Meding, Wuppertal (DE); Florian Sohler, Essen (DE); Julian Marius Glueck, Essen (DE)

(73) Assignee: Bayer Aktiengesellschaft, Leverkusen (DE)

( * ) Notice: Subject to any disclaimer, the term of this patent is extended or adjusted under 35 U.S.C. 154(b) by 36 days.

(21) Appl. No.: 16/760,704

(22) PCT Filed: Oct. 25, 2018

(86) PCT No.: PCT/EP2018/079333
§ 371 (c)(1),
(2) Date: Apr. 30, 2020

(87) PCT Pub. No.: WO2019/086331
PCT Pub. Date: May 9, 2019

(65) Prior Publication Data
US 2020/0332013 A1    Oct. 22, 2020

(30) Foreign Application Priority Data

Nov. 2, 2017 (EP) .................................. 17199746
Nov. 8, 2017 (EP) .................................. 17200666

(51) Int. Cl.
*C07K 16/28* (2006.01)
*G01N 33/68* (2006.01)

(52) U.S. Cl.
CPC ..... *C07K 16/2863* (2013.01); *G01N 33/6854* (2013.01); *C07K 2317/31* (2013.01); *C07K 2317/622* (2013.01); *C07K 2317/75* (2013.01); *C07K 2317/92* (2013.01)

(58) Field of Classification Search
CPC ............ C07K 16/2863; C07K 2317/31; C07K 2317/622; C07K 2317/75; C07K 2317/92; G01N 33/6854
See application file for complete search history.

(56) References Cited

U.S. PATENT DOCUMENTS

| | | |
|---|---|---|
| 4,376,110 A | 3/1983 | David et al. |
| 4,634,664 A | 1/1987 | Oestberg |
| 4,634,666 A | 1/1987 | Engleman et al. |
| 4,676,980 A | 6/1987 | Segal et al. |
| 4,751,180 A | 6/1988 | Cousens et al. |
| 4,935,233 A | 6/1990 | Bell et al. |
| 5,731,168 A | 3/1998 | Carter et al. |
| 8,216,805 B2 | 7/2012 | Carter et al. |
| 2012/0171203 A1 | 7/2012 | Yan et al. |

FOREIGN PATENT DOCUMENTS

| | | |
|---|---|---|
| WO | 8809344 A1 | 12/1988 |
| WO | 9117271 A1 | 11/1991 |
| WO | 9201047 A1 | 1/1992 |
| WO | 9308829 A1 | 5/1993 |
| WO | 9623879 A1 | 8/1996 |
| WO | 9954440 A1 | 10/1999 |
| WO | 0104144 A2 | 1/2001 |
| WO | 03029462 A1 | 4/2003 |
| WO | 2011116212 A2 | 9/2011 |
| WO | 2016005756 A1 | 1/2016 |

OTHER PUBLICATIONS

Szabo Alexander; Et. Al., "Surface plasmon resonance and its use in biomolecular interaction analysis (BIA)", Current Opinion in Structural Biology, 1995, 699-705.
Traunecker Andre; Et. Al., "Bispecific single chain molecules (Janusins) target cytotoxic lymphocytes on HIV infected cells", The EMBO Journal, 1991, 10 / 12, 3655-3659.
Tutt A.; Et. Al., "Trispecific F (ab') 3 derivatives that use cooperative signaling via the TCR/CD3 complex and CD2 to activate and redirect resting cytotoxic T cells", The Journal of Immunology, 1991, 60-69.
Varga Alison C.; Et. Al., "The disparate role of BMP in stem cell biology", Oncogene, 2005, 5713-5721.
Wang Guoliang; Et. Al., "Novel homozygous BMP9 nonsense mutation causes pulmonary arterial hypertension: a case report", BMC Pulmonary Medicine, 2016.
Wang Shinong; Et. Al., "Bone Morphogenetic Protein-7 Signals Opposing TransformingGrowth Factorin Mesangial Cells", The Journal of Biological Chemistry, 2004, 279 / 22, 23200-23206.
Asahina; Izumi Et. Al., "Human Osteogenic Protein-1 Induces Chondroblastic, Osteoblastic, and/or Adipocytic Differentiation of Clonal Murine Target Cells", Experimental Cell Research, 1996, 38-47.
Atwell Shane; Et. Al., "Stable Heterodimers from Remodeling the Domain Interface of a Homodimer using a Phage Display Library", J. Mol. Biol., 1997, 26-35.
Beste Gerald; Et. Al., "Small antibody-like proteins with prescribed ligand specificites derived from the lipocalin fold", Proc. Natl. Adad. Sci., Mar. 1999, 1898-1903.
Bosse Roger; Et. Al., "Application Note Principles of AlphaScreen Amplified Luminesent Proximity Homogenous Assay", Perkin Elmer Life Sciences, 2002, 1-8.

(Continued)

*Primary Examiner* — Ruixiang Li

(57) ABSTRACT

Bispecific antibodies binding ALK-1 and BMPR-2 The present invention relates to bispecific antibodies binding human ALK-1 and human BMPR-2. Also provided are BsABs which are agonists of ALK-1/BMPR-2 signaling, and BsABs which do not trigger osteogenic signaling. Furthermore, the invention relates to pharmaceutical uses of the BsABs, in particular for the treatment of pulmonary hypertension. Also provided are methods to screen for BsABs for use in the therapy, e.g. of pulmonary hypertension.

2 Claims, 4 Drawing Sheets
Specification includes a Sequence Listing.

(56) References Cited

OTHER PUBLICATIONS

Brennan M.; Et. Al., "Preparation of Bispecific Antibodies by ChemicalRecombination of Monoclonal Immunoglobulin G1Fragments", Science, 1985, 229, 81-83.

Burton Victoria J.; Et. Al., "Bone morphogenetic protein receptor II regulates pulmonary artery endothelial cell barrier function", The American Society of Hematology, 2011, 117 / 1, 333-341.

Cheng Hongwei; Et. Al., "Osteogenic activity of the fourteen types of human bone morphogeneticproteins (BMPs)", The Journalof Bone & Joint Surgery, 2003, 85A, 1544-1552.

David Laurent; Et. Al., "Identification of BMP9 and BMP10 as functional activators of the orphan activinreceptor-like kinase 1 (ALK1) in endothelial cells", Blood Journal, 2007, 109 / 5, 1953-1961.

Fan Gaowei; Et. Al., "Bispecific antibodies and their applications", Journal of Hematology & Oncology, 2015.

Gill Davinder S.; Et. Al., "Biopharmaceutical drug discovery using novel proteinscaffolds", Current Opinion in Biotechnology, 2006, 653-658.

Gruber M.; Et. Al., "Efficient tumor cell lysis mediated by a bispecific single chain antibody expressed in *Escherichia coli*", Journal of Immunology, 1994, 5368-5374.

Hamers-Casterma C.; Et. Al., "Naturally occurring antibodies devoid of light chains", Nature, 1993, 363, 446-448.

Hoeper Marius M.; Et. Al., "Pulmonary Hypertension", Deutsches Ärzteblatt International, 2017, 114, 73-84.

Holliger Philipp; Et. Al., ""Diabodies": Small bivalent and bispecific antibody fragments", Proc. Natl. Acad. Sci. USA, 1993, 90, 6444-6448.

Holt Lucy J.; Et. Al., "Domain antibodies: proteins for therapy", Trends in Biotechnology, Nov. 2003, 21 /11, 484-490.

Huston James S.; Et. Al., "Protein engineering of antibody binding sites: Recovery of specificactivity in an anti-digoxin single-chain Fv analogue produced in*Escherichia coli*", Proc. Natl. Acad. Sci. USA, Aug. 1988, 85, 5879-58.

Inada Masaki; Et. Al., "Bone Morphogenetic Protein-12 and -13 Inhibit Terminal Differentiation ofMyoblasts, but Do Not Induce Their Differentiation into Osteoblasts", Biochemical and Biophysial Research Communications, 1996, 222, 317-322.

"International Preliminary Report on Patentability, PCT App. No. PCT/EP2018/079333", dated May 14, 2020.

"International Search Report and Written Opinion of PCT App. No. PCT/EP2018/079333", dated May 2, 2019.

Isaacs Michael J.; Et. Al., "Bone Morphogenetic Protein-2 and -6 HeterodimerIllustrates the Nature of Ligand-Receptor Assembly", Molecular Endocrinology, 2010, 24, 1469-1477.

Jortikka Leena; Et. Al., "Use of Myoblasts in Assaying the Osteoinductivity of Bonemorphogenetic Proteins", Life Sciences, 1998, 62 / 26, 2359-2368.

Knappik Achim; Et. Al., "Fully Synthetic Human Combinatorial Antibody Libraries (HuCAL) Based on Modular Consensus Frameworks and CDRs Randomized with Trinucleotides", J. Mol. Biol., 2000, 296, 57-86.

Kohler G.; Et. Al., "Continuous cultures of fused cells secreting antibody of predefined specificity", Nature, 1975, 256, 495-497.

Kostelny Sheri A.; Et. Al., "Formation of a Bispecific Antibody By the Use of Leucine Zippers", The Journal of Immunology, 1992, 148, 1547-1553.

Kusanagi Kiyoshi; Et. Al., "Characterization of a Bone Morphogenetic Protein-responsive Smad-binding Element", Molecular Biology of the Cell, Feb. 2000, 11, 555-565.

Kwon Yong-Uk; Et. Al., "Quantitative Evaluation of the Relative Cell Permeability of Peptoids and Peptides", J. Am. Chem. Soc., 2007, 129 / 6, 1508-1509.

Labrijn Aran F.; Et. Al., "Efficient generation of stable bispecific IgG1 bycontrolled Fab-arm exchange", Proc. Natl. Acad. Sci. USA, Mar. 2013, 110 / 13, 5145-5150.

Lane Nancy E.; Et. Al., "Both hPTH(1-34) and bFGF Increase Trabecular Bone Mass in OsteopenicRats but They Have Different Effects on Trabecular Bone Architecture", Journal of Bone and Mineral Research, Nov. 2003, 18, 2105-2115.

Long Lu; Et. Al., "Selective enhancement of endothelial BMPR-II with BMP9 reverses pulmonary arterial hypertension", Nat Med., Jul. 2015, 21 / 7, 777-785.

Lux Andreas; Et. Al., "ALK1 signalling analysis identifies angiogenesis related genes and reveals disparity between TGF-β and constitutively active receptor induced gene expression", BioMed Central, 2006.

Ma Lijiang; Et. Al., "Quantitative Analysis of Copy Number Variants Based on Real-Time LightCycler PCR", Human Genetics, 2014.

Masaka Inada; Et. Al., "Bone Morphogenetic Protein-12 and-13 Inhibit Terminal Differentiation of Myoblasts, but Do Not Induce Their Differentiation into Osteoblasts", Biochemical and Biophysial Research Communications, 1996, 222 / 2, 317-322.

McDonnell; James M., "Surface plasmon resonance: towards an understanding of themechanisms of biological molecular recognition", Current Opinion in Chemical Biology, 2001, 572-577.

Merchant A. Margaret; Et. Al., "An efficient route to human bispecific IgG", Nature Biotechnology, 1998, 677-681.

Merrifield; R.B., "Solid Phase Peptide Synthesis. I. The Synthesis of a Tetrapeptide", Am. Chem. Soc., 1963, 2149-2154.

Milstein C.; Et. Al., "Hybrid hybridomas andtheir use in immunohistochemistry", Nature, 1983, 537-540.

Miyazono Kohei; Et. Al., "Bone morphogenetic protein receptors and signal transduction", J. Biochem, 2010, 35-51.

Mosavi Leila K.; Et. Al., "The ankyrin repeat as molecular architecturefor protein recognition", The Protein Society, 2004, 1435-1448.

Napolitano Eugene W.; Et. Al., "Glubodies: randomized libraries of glutathionetransferase enzymes", Chemistry & Biology, 1996, 359-367.

Ostberg Lars; Et. Al., "Hybridomas Stably Producing Human Antibodies, 1983", 1983, 2 / 4, 361-367.

Pearce Kenneth H.; Et. Al., "Growth Hormone Binding Affinity for Its Receptor Surpasses the Requirements for Cellular Activity", Biochemistry, 1999, 81-89.

Piao Chunmei; Et. Al., "identification of multiple ACVRL/ mutations in patients with pulmonary arterial hYpertensidn by targeted exome capture", Clinical Science, 2016, 1559-1569.

Poljak Roberto J.; Et. Al., "Production and structure of diabodies", Structure, 1994, 1121-1123.

Ridgway John B. B.; Et. Al., "'Knobs-into-holes' engineering of antibody CH3 domains for heavychain heterodimerization", Protein Engineering, 1996, 9 / 7, 617-621.

Roberge Jacques Y.; Et. Al., "A Strategy for a Convergent Synthesis of N-Linked Glycopeptides on a Solid Support, 1995", Science, 1995, 269, 202-204.

Silverman Joshua; Et. Al., "Multivalent avimer proteins evolved by exon shuffling ofa family of human receptor domains", Nature Biotechnology, 2005, 23 / 12, 1556-1561.

Sjolander Stefan; Et. Al., "Integrated Fluid Handling System for Biomolecular Interaction Analysis", Anal. Chem., 1991, 2338-2345.

Skerra; Arne, "Engineered protein scaffolds for molecular recognition", Journal of Molecular Recognition, 2000, 167-187.

Songslivilai S.; Et. Al., "Bispecific antibody: a tool for diagnosis and treatment of disease", 1990, 1990, 315-321.

Staerz Uwe D.; Et. Al., "Hybrid antibodies can target sites for attack by T cells, 1985", Nature Publishing Group, 1985, 314, 628-631.

SEQUENCE LISTING

<160> NUMBER OF SEQ ID NOS: 117

<210> SEQ ID NO 1
<211> LENGTH: 477
<212> TYPE: PRT
<213> ORGANISM: Artificial Sequence
<220> FEATURE:
<223> OTHER INFORMATION: TPP-14696; 13654-13667-scFv-kih-IgG2_Fc; Chain1

<400> SEQUENCE: 1

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Phe Asp Tyr Trp Gly Gln Gly Thr Leu Val Thr Val Thr
            100                 105                 110

Ser Ser Gly Gly Gly Ser Gly Gly Gly Ser Gly Gly Gly
        115                 120                 125

Ser Gln Ser Val Leu Thr Gln Pro Pro Ser Ala Ser Gly Thr Pro Gly
        130                 135                 140

Gln Arg Val Thr Ile Ser Cys Ser Gly Ser Ser Asn Ile Gly Ser
145                 150                 155                 160

Asn Tyr Val Tyr Trp Tyr Gln Gln Leu Pro Gly Thr Ala Pro Lys Leu
                165                 170                 175

Leu Ile Tyr Gly Asn Ile Asn Arg Pro Ser Gly Val Pro Asp Arg Phe
            180                 185                 190

Ser Gly Ser Lys Ser Gly Thr Ser Ala Ser Leu Ala Ile Ser Gly Leu
        195                 200                 205

Arg Ser Glu Asp Glu Ala Asp Tyr Tyr Cys Ala Ala Trp Asp Asp Ser
        210                 215                 220

Leu Asn Gly Arg Val Phe Gly Gly Gly Thr Lys Leu Thr Val Leu Gly
225                 230                 235                 240

Gly Gly Gly Ser Gly Gly Gly Ser Gly Gly Gly Ser Gly Val
                245                 250                 255

Glu Cys Pro Pro Cys Pro Ala Pro Pro Val Ala Gly Pro Ser Val Phe
            260                 265                 270

Leu Phe Pro Pro Lys Pro Lys Asp Thr Leu Met Ile Ser Arg Thr Pro
        275                 280                 285

Glu Val Thr Cys Val Val Val Asp Val Ser His Glu Asp Pro Glu Val
        290                 295                 300

Gln Phe Asn Trp Tyr Val Asp Gly Val Glu Val His Asn Ala Lys Thr
305                 310                 315                 320

Lys Pro Arg Glu Glu Gln Phe Asn Ser Thr Phe Arg Val Val Ser Val
                325                 330                 335

Leu Thr Val Val His Gln Asp Trp Leu Asn Gly Lys Glu Tyr Lys Cys
            340                 345                 350

Lys Val Ser Asn Lys Gly Leu Pro Ala Pro Ile Glu Lys Thr Ile Ser
        355                 360                 365

Lys Thr Lys Gly Gln Pro Arg Glu Pro Gln Val Tyr Thr Leu Pro Pro
        370                 375                 380

Cys Arg Glu Glu Met Thr Lys Asn Gln Val Ser Leu Trp Cys Leu Val
385                 390                 395                 400

Lys Gly Phe Tyr Pro Ser Asp Ile Ala Val Glu Trp Glu Ser Asn Gly
                405                 410                 415

Gln Pro Glu Asn Asn Tyr Lys Thr Thr Pro Pro Met Leu Asp Ser Asp
            420                 425                 430

Gly Ser Phe Phe Leu Tyr Ser Lys Leu Thr Val Asp Lys Ser Arg Trp
        435                 440                 445

Gln Gln Gly Asn Val Phe Ser Cys Ser Val Met His Glu Ala Leu His
        450                 455                 460

Asn His Tyr Thr Gln Lys Ser Leu Ser Leu Ser Pro Gly
465                 470                 475

<210> SEQ ID NO 2
<211> LENGTH: 5
<212> TYPE: PRT
<213> ORGANISM: Artificial Sequence
<220> FEATURE:

```
<223> OTHER INFORMATION: TPP-14696; 13654-13667-scFv-kih-IgG2_Fc; Chain1
      HCDR1

<400> SEQUENCE: 2

Ile Tyr Ala Met Ser
1               5

<210> SEQ ID NO 3
<211> LENGTH: 17
<212> TYPE: PRT
<213> ORGANISM: Artificial Sequence
<220> FEATURE:
<223> OTHER INFORMATION: TPP-14696; 13654-13667-scFv-kih-IgG2_Fc; Chain1
      HCDR2

<400> SEQUENCE: 3

Ala Ile Ser Gly Ser Gly Gly Ser Thr Tyr Tyr Ala Asp Ser Val Lys
1               5                   10                  15

Gly

<210> SEQ ID NO 4
<211> LENGTH: 4
<212> TYPE: PRT
<213> ORGANISM: Artificial Sequence
<220> FEATURE:
<223> OTHER INFORMATION: TPP-14696; 13654-13667-scFv-kih-IgG2_Fc; Chain1
      HCDR3

<400> SEQUENCE: 4

Asp Phe Asp Tyr
1

<210> SEQ ID NO 5
<211> LENGTH: 13
<212> TYPE: PRT
<213> ORGANISM: Artificial Sequence
<220> FEATURE:
<223> OTHER INFORMATION: TPP-14696; 13654-13667-scFv-kih-IgG2_Fc; Chain1
      LCDR1

<400> SEQUENCE: 5

Ser Gly Ser Ser Ser Asn Ile Gly Ser Asn Tyr Val Tyr
1               5                   10

<210> SEQ ID NO 6
<211> LENGTH: 7
<212> TYPE: PRT
<213> ORGANISM: Artificial Sequence
<220> FEATURE:
<223> OTHER INFORMATION: TPP-14696; 13654-13667-scFv-kih-IgG2_Fc; Chain1
      LCDR2

<400> SEQUENCE: 6

Gly Asn Ile Asn Arg Pro Ser
1               5

<210> SEQ ID NO 7
<211> LENGTH: 11
<212> TYPE: PRT
<213> ORGANISM: Artificial Sequence
<220> FEATURE:
<223> OTHER INFORMATION: TPP-14696; 13654-13667-scFv-kih-IgG2_Fc; Chain1
      LCDR3

<400> SEQUENCE: 7

Ala Ala Trp Asp Asp Ser Leu Asn Gly Arg Val
1               5                   10
```

<210> SEQ ID NO 8
<211> LENGTH: 487
<212> TYPE: PRT
<213> ORGANISM: Artificial Sequence
<220> FEATURE:
<223> OTHER INFORMATION: TPP-14696; 13654-13667-scFv-kih-IgG2_Fc; Chain2

<400> SEQUENCE: 8

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Ala
            20                  25                  30

Trp Met Asn Trp Val Arg Gln Ala Pro Gly Lys Gly Leu Glu Trp Val
        35                  40                  45

Ser Ser Ile Ser Ser Ser Ser Tyr Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ala Val Ala Ala Gly Met Phe Trp Gly Leu Asp Gln Trp
            100                 105                 110

Gly Gln Gly Thr Leu Val Thr Val Thr Ser Ser Gly Gly Gly Gly Ser
        115                 120                 125

Gly Gly Gly Gly Ser Gly Gly Gly Ser Gln Ser Val Leu Thr Gln
    130                 135                 140

Pro Pro Ser Ala Ser Gly Thr Pro Gly Gln Arg Val Thr Ile Ser Cys
145                 150                 155                 160

Ser Gly Ser Arg Ser Asn Ile Gly Ser Asn Ser Val His Trp Tyr Gln
                165                 170                 175

Gln Leu Pro Gly Thr Ala Pro Lys Leu Leu Ile Tyr Gly Asn Ser Asn
            180                 185                 190

Arg Pro Ser Gly Val Pro Asp Arg Phe Ser Gly Ser Lys Ser Gly Thr
        195                 200                 205

Ser Ala Ser Leu Ala Ile Ser Gly Leu Arg Ser Glu Asp Glu Ala Asp
    210                 215                 220

Tyr Tyr Cys Gln Ser Tyr Asp Ser Ser Leu Asn Asp His Val Val Phe
225                 230                 235                 240

Gly Gly Gly Thr Lys Leu Thr Val Leu Gly Gly Gly Ser Gly Gly
                245                 250                 255

Gly Gly Ser Gly Gly Gly Gly Ser Gly Val Glu Cys Pro Pro Cys Pro
            260                 265                 270

Ala Pro Pro Val Ala Gly Pro Ser Val Phe Leu Phe Pro Pro Lys Pro
        275                 280                 285

Lys Asp Thr Leu Met Ile Ser Arg Thr Pro Glu Val Thr Cys Val Val
    290                 295                 300

Val Asp Val Ser His Glu Asp Pro Glu Val Gln Phe Asn Trp Tyr Val
305                 310                 315                 320

Asp Gly Val Glu Val His Asn Ala Lys Thr Lys Pro Arg Glu Glu Gln
                325                 330                 335

Phe Asn Ser Thr Phe Arg Val Val Ser Val Leu Thr Val Val His Gln
            340                 345                 350

Asp Trp Leu Asn Gly Lys Glu Tyr Lys Cys Lys Val Ser Asn Lys Gly
        355                 360                 365
```

```
Leu Pro Ala Pro Ile Glu Lys Thr Ile Ser Lys Thr Lys Gly Gln Pro
    370                 375                 380

Arg Glu Pro Gln Val Cys Thr Leu Pro Pro Ser Arg Glu Glu Met Thr
385                 390                 395                 400

Lys Asn Gln Val Ser Leu Ser Cys Ala Val Lys Gly Phe Tyr Pro Ser
                405                 410                 415

Asp Ile Ala Val Glu Trp Glu Ser Asn Gly Gln Pro Glu Asn Asn Tyr
            420                 425                 430

Lys Thr Thr Pro Pro Met Leu Asp Ser Asp Gly Ser Phe Phe Leu Val
        435                 440                 445

Ser Lys Leu Thr Val Asp Lys Ser Arg Trp Gln Gln Gly Asn Val Phe
    450                 455                 460

Ser Cys Ser Val Met His Glu Ala Leu His Asn His Tyr Thr Gln Lys
465                 470                 475                 480

Ser Leu Ser Leu Ser Pro Gly
                485

<210> SEQ ID NO 9
<211> LENGTH: 5
<212> TYPE: PRT
<213> ORGANISM: Artificial Sequence
<220> FEATURE:
<223> OTHER INFORMATION: TPP-14696; 13654-13667-scFv-kih-IgG2_Fc; Chain2
      HCDR1

<400> SEQUENCE: 9

Asn Ala Trp Met Asn
1               5

<210> SEQ ID NO 10
<211> LENGTH: 17
<212> TYPE: PRT
<213> ORGANISM: Artificial Sequence
<220> FEATURE:
<223> OTHER INFORMATION: TPP-14696; 13654-13667-scFv-kih-IgG2_Fc; Chain2
      HCDR2

<400> SEQUENCE: 10

Ser Ile Ser Ser Ser Ser Tyr Ile Tyr Tyr Ala Asp Ser Val Lys
1               5                   10                  15
Gly

<210> SEQ ID NO 11
<211> LENGTH: 13
<212> TYPE: PRT
<213> ORGANISM: Artificial Sequence
<220> FEATURE:
<223> OTHER INFORMATION: TPP-14696; 13654-13667-scFv-kih-IgG2_Fc; Chain2
      HCDR3

<400> SEQUENCE: 11

Ala Val Ala Ala Gly Gly Met Phe Trp Gly Leu Asp Gln
1               5                   10

<210> SEQ ID NO 12
<211> LENGTH: 13
<212> TYPE: PRT
<213> ORGANISM: Artificial Sequence
<220> FEATURE:
<223> OTHER INFORMATION: TPP-14696; 13654-13667-scFv-kih-IgG2_Fc; Chain2
      LCDR1

<400> SEQUENCE: 12
```

Ser Gly Ser Arg Ser Asn Ile Gly Ser Asn Ser Val His
1               5                   10

<210> SEQ ID NO 13
<211> LENGTH: 7
<212> TYPE: PRT
<213> ORGANISM: Artificial Sequence
<220> FEATURE:
<223> OTHER INFORMATION: TPP-14696; 13654-13667-scFv-kih-IgG2_Fc; Chain2
      LCDR2

<400> SEQUENCE: 13

Gly Asn Ser Asn Arg Pro Ser
1               5

<210> SEQ ID NO 14
<211> LENGTH: 12
<212> TYPE: PRT
<213> ORGANISM: Artificial Sequence
<220> FEATURE:
<223> OTHER INFORMATION: TPP-14696; 13654-13667-scFv-kih-IgG2_Fc; Chain2
      LCDR3

<400> SEQUENCE: 14

Gln Ser Tyr Asp Ser Ser Leu Asn Asp His Val Val
1               5                   10

<210> SEQ ID NO 15
<211> LENGTH: 1431
<212> TYPE: DNA
<213> ORGANISM: Artificial Sequence
<220> FEATURE:
<223> OTHER INFORMATION: TPP-14696; 13654-13667-scFv-kih-IgG2_Fc; Chain1

<400> SEQUENCE: 15
gaagttcagc tgctggaatc tggcggcgga ctggttcaac tggcggatc tctgagactg      60 agctgtgccg ccagcggctt cacctttagc atctacgcca tgagctgggt ccgacaggcc     120
cctggaaaag gccttgaatg gtgtccgcc atctctggca gcggcggcag cacatattac      180
gccgattctg tgaagggcag attcaccatc agccgggaca cagcaagaa caccctgtac     240 ctgcagatga acagcctgag agccgaggac accgccgtgt actattgcgc cagagacttc    300
gactattggg ccagggcac actggtcacc gtgacatcta gcggaggcgg aggatcaggt     360
ggcggtggaa gtggtggcgg aggttctcag tctgtgctga cacagcctcc tagcgcctct    420
ggaacacctg ccagagagt gaccatcagc tgtagcggca gcagcaa catcggcagc        480 aactacgtgt actggtatca gcagctgccc ggcacagccc taaactgct gatctacggc     540 aacatcaaca gacccagcgg cgtgcccgat agattcagcg gctctaagtc tggcacaagc    600
gccagcctgg ccatcagcgg actgagatct gaggacgagg ccgactacta ttgtgccgcc    660
tgggacgata gcctgaacgg cagagttttt ggcggaggca ccaagctgac agtgcttgga    720
ggtggtggat caggcggtgg cggaagcggc ggaggtggaa gcggagttga atgtcctcca    780
tgtcctgctc ctccagtggc cggaccttcc gtgtttctgt tccctccaaa gcctaaggac    840 acctgatga tcagcagaac ccctgaagtg acctgcgtgg tggtggatgt gtcccacgag    900
gatcctgagg tgcagttcaa ttggtacgtg gacggcgtgg aagtgcacaa cgccaagacc    960
aagcctagag aggaacagtt caacagcacc ttcagagtgg tgtccgtgct gaccgtggtg   1020
catcaggatt ggctgaacgg caaagagtac aagtgcaagg tgtccaacaa gggcctgcct   1080
gctcctatcg agaaaaccat cagcaagaca aagggccagc ctcgcgagcc ccaggtttac   1140

-continued

```
acacttcctc catgccggga agagatgacc aagaaccagg tgtccctgtg gtgcctggtc    1200
aagggcttct acccttccga tatcgccgtg aatgggaga gcaatggcca gcctgagaac    1260
aactacaaga ccacacctcc tatgctggac agcgacggct cattcttcct gtacagcaag    1320
ctgacagtgg acaagagcag atggcagcag ggcaacgtgt tcagctgcag cgtgatgcac    1380
gaggccctgc acaaccacta cacccagaag tccctgagcc tgtctcctgg a             1431
```

<210> SEQ ID NO 16
<211> LENGTH: 15
<212> TYPE: DNA
<213> ORGANISM: Artificial Sequence
<220> FEATURE:
<223> OTHER INFORMATION: TPP-14696; 13654-13667-scFv-kih-IgG2_Fc; Chain1
      HCDR1

<400> SEQUENCE: 16

```
atctacgcca tgagc                                                      15
```

<210> SEQ ID NO 17
<211> LENGTH: 51
<212> TYPE: DNA
<213> ORGANISM: Artificial Sequence
<220> FEATURE:
<223> OTHER INFORMATION: TPP-14696; 13654-13667-scFv-kih-IgG2_Fc; Chain1
      HCDR2

<400> SEQUENCE: 17

```
gccatctctg gcagcggcgg cagcacatat tacgccgatt ctgtgaaggg c              51
```

<210> SEQ ID NO 18
<211> LENGTH: 12
<212> TYPE: DNA
<213> ORGANISM: Artificial Sequence
<220> FEATURE:
<223> OTHER INFORMATION: TPP-14696; 13654-13667-scFv-kih-IgG2_Fc; Chain1
      HCDR3

<400> SEQUENCE: 18

```
gacttcgact at                                                         12
```

<210> SEQ ID NO 19
<211> LENGTH: 39
<212> TYPE: DNA
<213> ORGANISM: Artificial Sequence
<220> FEATURE:
<223> OTHER INFORMATION: TPP-14696; 13654-13667-scFv-kih-IgG2_Fc; Chain1
      LCDR1

<400> SEQUENCE: 19

```
agcggcagca gcagcaacat cggcagcaac tacgtgtac                            39
```

<210> SEQ ID NO 20
<211> LENGTH: 21
<212> TYPE: DNA
<213> ORGANISM: Artificial Sequence
<220> FEATURE:
<223> OTHER INFORMATION: TPP-14696; 13654-13667-scFv-kih-IgG2_Fc; Chain1
      LCDR2

<400> SEQUENCE: 20

```
ggcaacatca acagacccag c                                               21
```

<210> SEQ ID NO 21
<211> LENGTH: 33

```
<212> TYPE: DNA
<213> ORGANISM: Artificial Sequence
<220> FEATURE:
<223> OTHER INFORMATION: TPP-14696; 13654-13667-scFv-kih-IgG2_Fc; Chain1
      LCDR3

<400> SEQUENCE: 21
gccgcctggg acgatagcct gaacggcaga gtt                                    33

<210> SEQ ID NO 22
<211> LENGTH: 1461
<212> TYPE: DNA
<213> ORGANISM: Artificial Sequence
<220> FEATURE:
<223> OTHER INFORMATION: TPP-14696; 13654-13667-scFv-kih-IgG2_Fc; Chain2

<400> SEQUENCE: 22
gaagttcagc tgctggaatc tggcggcgga ctggttcaac tggcggatc tctgagactg         60 agctgtgccg ccagcggctt cacctttagc aacgcctgga tgaactgggt ccgacaggcc       120
cctggaaaag gcctggaatg ggtgtccagc atcagcagca gctccagcta catctactac       180
gccgacagcg tgaagggcag attcaccatc agccgggaca acagcaagaa cacccctgtac      240 ctgcagatga cagcctgag agccgaggac accgccgtgt actattgtgc cagagctgtt       300
gctgccggcg aatgttttg gggccttgat caatggggcc agggcaccct ggtcacagtg       360
acatctagcg gaggcggagg atcaggtggc ggtggaagtg gtggcggagg ttctcagtct       420
gtgctgacac agcctcctag cgcctctgga cacctggcc agagagtgac catcagctgt       480
agcggcagca gaagcaacat cggctccaac agcgtgcact ggtatcagca gctgcctggc       540
acagccccta aactgctgat ctacggcaac agcaacagac cagcggcgt gcccgataga       600 ttcagcggct ctaagtctgg cacctctgcc agctggcca tctctggcct gagatctgag       660
gacgaggccg actactactg ccagtcctac gacagcagcc tgaacgatca cgtggtgttt       720
ggcggaggca ccaagctgac agttcttgga ggtggtggaa gtggcggagg cggaagcggt       780
ggtggtggat ctggtgttga atgtcctcca tgtcctgctc ctccagtggc cggaccttcc       840
gtgtttctgt tccctccaaa gcctaaggac ccctgatga tcagcagaac ccctgaagtg       900
acctgcgtgg tggtggatgt gtcccacgag gatcctgagg tgcagttcaa ttggtacgtg       960
gacggcgtgg aagtgcacaa cgccaagacc aagcctagag aggaacagtt caacagcacc      1020
ttcagagtgg tgtccgtgct gaccgtggtg catcaggatt ggctgaacgg caaagagtac      1080
aagtgcaagg tgtccaacaa gggcctgcct gctcctatcg agaaaaccat cagcaagaca      1140
aagggccagc ctcgcgagcc ccaagtctgt acacttcctc caagccggga agagatgacc      1200
aagaaccagg tgtccctgag ctgtgccgtg aagggcttct acccttccga tatcgccgtg      1260
gaatgggaga gcaatggcca gcctgagaac aactacaaga ccacacctcc tatgctggac      1320
agcgacggct cattcttcct ggtgtccaag ctgacagtgg acaagagcag atggcagcag      1380
ggcaacgtgt tcagctgcag cgtgatgcac gaggccctgc acaaccacta cacccagaag      1440
tccctgtctc tgagccctgg a                                               1461

<210> SEQ ID NO 23
<211> LENGTH: 15
<212> TYPE: DNA
<213> ORGANISM: Artificial Sequence
<220> FEATURE:
<223> OTHER INFORMATION: TPP-14696; 13654-13667-scFv-kih-IgG2_Fc; Chain2
      HCDR1
```

<400> SEQUENCE: 23
aacgcctgga tgaac                                                    15

<210> SEQ ID NO 24
<211> LENGTH: 51
<212> TYPE: DNA
<213> ORGANISM: Artificial Sequence
<220> FEATURE:
<223> OTHER INFORMATION: TPP-14696; 13654-13667-scFv-kih-IgG2_Fc; Chain2
      HCDR2

<400> SEQUENCE: 24
agcatcagca gcagctccag ctacatctac tacgccgaca gcgtgaaggg c             51

<210> SEQ ID NO 25
<211> LENGTH: 39
<212> TYPE: DNA
<213> ORGANISM: Artificial Sequence
<220> FEATURE:
<223> OTHER INFORMATION: TPP-14696; 13654-13667-scFv-kih-IgG2_Fc; Chain2
      HCDR3

<400> SEQUENCE: 25
gctgttgctg ccggcggaat gttttggggc cttgatcaa                           39

<210> SEQ ID NO 26
<211> LENGTH: 39
<212> TYPE: DNA
<213> ORGANISM: Artificial Sequence
<220> FEATURE:
<223> OTHER INFORMATION: TPP-14696; 13654-13667-scFv-kih-IgG2_Fc; Chain2
      LCDR1

<400> SEQUENCE: 26
agcggcagca gaagcaacat cggctccaac agcgtgcac                           39

<210> SEQ ID NO 27
<211> LENGTH: 21
<212> TYPE: DNA
<213> ORGANISM: Artificial Sequence
<220> FEATURE:
<223> OTHER INFORMATION: TPP-14696; 13654-13667-scFv-kih-IgG2_Fc; Chain2
      LCDR2

<400> SEQUENCE: 27
ggcaacagca acagacccag c                                              21

<210> SEQ ID NO 28
<211> LENGTH: 36
<212> TYPE: DNA
<213> ORGANISM: Artificial Sequence
<220> FEATURE:
<223> OTHER INFORMATION: TPP-14696; 13654-13667-scFv-kih-IgG2_Fc; Chain2
      LCDR3

<400> SEQUENCE: 28
cagtcctacg acagcagcct gaacgatcac gtggtg                              36

<210> SEQ ID NO 29
<211> LENGTH: 477
<212> TYPE: PRT
<213> ORGANISM: Artificial Sequence
<220> FEATURE:
<223> OTHER INFORMATION: TPP-14719; 13660-13469-scFv-kih-IgG2_Fc; Chain1

<400> SEQUENCE: 29

-continued

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ala Asn Ile Asn Gln Asp Gly Ser Glu Lys Asn Tyr Val Asp Ser Met
    50                  55                  60

Arg Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Phe Asp Tyr Trp Gly Gln Gly Thr Leu Val Thr Val Thr
            100                 105                 110

Ser Ser Gly Gly Gly Ser Gly Gly Gly Ser Gly Gly Gly Gly
            115                 120                 125

Ser Gln Ser Val Leu Ala Gln Pro Pro Ser Ala Ser Gly Thr Pro Gly
    130                 135                 140

Gln Arg Val Thr Ile Ser Cys Ser Gly Ser Ser Asn Ile Gly Ser
145                 150                 155                 160

Asn Tyr Val Tyr Trp Tyr Gln Gln Leu Pro Gly Thr Ala Pro Lys Leu
            165                 170                 175

Leu Ile Tyr Gly Asn Asn Lys Arg Pro Ser Gly Val Pro Asp Arg Phe
            180                 185                 190

Ser Gly Ser Lys Ser Gly Thr Ser Ala Ser Leu Ala Ile Ser Gly Leu
            195                 200                 205

Arg Ser Glu Asp Glu Ala Asp Tyr Tyr Cys Ala Ala Trp Asp Asp Ser
210                 215                 220

Leu Asn Gly Arg Val Phe Gly Gly Gly Thr Lys Leu Thr Val Leu Gly
225                 230                 235                 240

Gly Gly Gly Ser Gly Gly Gly Ser Gly Gly Gly Ser Gly Val
            245                 250                 255

Glu Cys Pro Pro Cys Pro Ala Pro Pro Val Ala Gly Pro Ser Val Phe
            260                 265                 270

Leu Phe Pro Pro Lys Pro Lys Asp Thr Leu Met Ile Ser Arg Thr Pro
            275                 280                 285

Glu Val Thr Cys Val Val Val Asp Val Ser His Glu Asp Pro Glu Val
            290                 295                 300

Gln Phe Asn Trp Tyr Val Asp Gly Val Glu Val His Asn Ala Lys Thr
305                 310                 315                 320

Lys Pro Arg Glu Glu Gln Phe Asn Ser Thr Phe Arg Val Val Ser Val
            325                 330                 335

Leu Thr Val Val His Gln Asp Trp Leu Asn Gly Lys Glu Tyr Lys Cys
            340                 345                 350

Lys Val Ser Asn Lys Gly Leu Pro Ala Pro Ile Glu Lys Thr Ile Ser
            355                 360                 365

Lys Thr Lys Gly Gln Pro Arg Glu Pro Gln Val Tyr Thr Leu Pro Pro
            370                 375                 380

Cys Arg Glu Glu Met Thr Lys Asn Gln Val Ser Leu Trp Cys Leu Val
385                 390                 395                 400

Lys Gly Phe Tyr Pro Ser Asp Ile Ala Val Glu Trp Glu Ser Asn Gly
            405                 410                 415

Gln Pro Glu Asn Asn Tyr Lys Thr Thr Pro Pro Met Leu Asp Ser Asp
```

```
                420                 425                 430
Gly Ser Phe Phe Leu Tyr Ser Lys Leu Thr Val Asp Lys Ser Arg Trp
            435                 440                 445

Gln Gln Gly Asn Val Phe Ser Cys Ser Val Met His Glu Ala Leu His
        450                 455                 460

Asn His Tyr Thr Gln Lys Ser Leu Ser Leu Ser Pro Gly
465                 470                 475

<210> SEQ ID NO 30
<211> LENGTH: 5
<212> TYPE: PRT
<213> ORGANISM: Artificial Sequence
<220> FEATURE:
<223> OTHER INFORMATION: TPP-14719; 13660-13469-scFv-kih-IgG2_Fc; Chain1
      HCDR1

<400> SEQUENCE: 30

Ser Tyr Ala Met Ser
1               5

<210> SEQ ID NO 31
<211> LENGTH: 17
<212> TYPE: PRT
<213> ORGANISM: Artificial Sequence
<220> FEATURE:
<223> OTHER INFORMATION: TPP-14719; 13660-13469-scFv-kih-IgG2_Fc; Chain1
      HCDR2

<400> SEQUENCE: 31

Asn Ile Asn Gln Asp Gly Ser Glu Lys Asn Tyr Val Asp Ser Met Arg
1               5                   10                  15

Gly

<210> SEQ ID NO 32
<211> LENGTH: 4
<212> TYPE: PRT
<213> ORGANISM: Artificial Sequence
<220> FEATURE:
<223> OTHER INFORMATION: TPP-14719; 13660-13469-scFv-kih-IgG2_Fc; Chain1
      HCDR3

<400> SEQUENCE: 32

Glu Phe Asp Tyr
1

<210> SEQ ID NO 33
<211> LENGTH: 13
<212> TYPE: PRT
<213> ORGANISM: Artificial Sequence
<220> FEATURE:
<223> OTHER INFORMATION: TPP-14719; 13660-13469-scFv-kih-IgG2_Fc; Chain1
      LCDR1

<400> SEQUENCE: 33

Ser Gly Ser Ser Ser Asn Ile Gly Ser Asn Tyr Val Tyr
1               5                   10

<210> SEQ ID NO 34
<211> LENGTH: 7
<212> TYPE: PRT
<213> ORGANISM: Artificial Sequence
<220> FEATURE:
<223> OTHER INFORMATION: TPP-14719; 13660-13469-scFv-kih-IgG2_Fc; Chain1
      LCDR2

<400> SEQUENCE: 34
```

-continued

Gly Asn Asn Lys Arg Pro Ser
1               5

<210> SEQ ID NO 35
<211> LENGTH: 11
<212> TYPE: PRT
<213> ORGANISM: Artificial Sequence
<220> FEATURE:
<223> OTHER INFORMATION: TPP-14719; 13660-13469-scFv-kih-IgG2_Fc; Chain1
      LCDR3

<400> SEQUENCE: 35

Ala Ala Trp Asp Asp Ser Leu Asn Gly Arg Val
1               5                   10

<210> SEQ ID NO 36
<211> LENGTH: 485
<212> TYPE: PRT
<213> ORGANISM: Artificial Sequence
<220> FEATURE:
<223> OTHER INFORMATION: TPP-14719; 13660-13469-scFv-kih-IgG2_Fc; Chain2

<400> SEQUENCE: 36

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Met Thr Trp Ile Arg Gln Ala Pro Gly Lys Gly Leu Glu Trp Val
        35                  40                  45

Ser Ser Ile Ser Gly Gly Ser Thr Tyr Tyr Ala Asp Ser Arg Lys Gly
    50                  55                  60

Arg Phe Thr Ile Ser Arg Asp Asn Ser Glu Asn Thr Leu Tyr Leu Gln
65                  70                  75                  80

Met Asn Ser Leu Arg Ala Glu Asp Thr Ala Val Tyr Tyr Cys Ala Arg
                85                  90                  95

Asp Phe Gly Val Ala Gly Trp Phe Gly Gln Tyr Gly Met Asp Val Trp
            100                 105                 110

Gly Gln Gly Thr Leu Val Thr Val Ser Ser Gly Gly Gly Gly Ser Gly
        115                 120                 125

Gly Gly Gly Ser Gly Gly Gly Ser Gln Ser Val Leu Thr Gln Pro
    130                 135                 140

Pro Ser Ala Ser Gly Thr Pro Gly Gln Arg Val Thr Ile Ser Cys Thr
145                 150                 155                 160

Gly Ser Ser Ser Asn Ile Gly Ala Gly Tyr Asp Val His Trp Tyr Gln
                165                 170                 175

Gln Leu Pro Gly Thr Ala Pro Lys Leu Leu Ile Tyr Arg Ser Asn Gln
            180                 185                 190

Arg Pro Ser Gly Val Pro Asp Arg Phe Ser Gly Ser Lys Ser Gly Thr
        195                 200                 205

Ser Ala Ser Leu Ala Ile Ser Gly Leu Arg Ser Glu Asp Glu Ala Asp
    210                 215                 220

Tyr Tyr Cys Ser Ser Tyr Ala Gly Asn Tyr Asn Leu Val Phe Gly Gly
225                 230                 235                 240

Gly Thr Lys Leu Thr Val Leu Gly Gly Gly Ser Gly Gly Gly Gly
                245                 250                 255

Ser Gly Gly Gly Gly Ser Gly Val Glu Cys Pro Pro Cys Pro Ala Pro
            260                 265                 270

Pro Val Ala Gly Pro Ser Val Phe Leu Phe Pro Pro Lys Pro Lys Asp
            275                 280                 285

Thr Leu Met Ile Ser Arg Thr Pro Glu Val Thr Cys Val Val Val Asp
290                 295                 300

Val Ser His Glu Asp Pro Glu Val Gln Phe Asn Trp Tyr Val Asp Gly
305                 310                 315                 320

Val Glu Val His Asn Ala Lys Thr Lys Pro Arg Glu Glu Gln Phe Asn
                325                 330                 335

Ser Thr Phe Arg Val Val Ser Val Leu Thr Val Val His Gln Asp Trp
            340                 345                 350

Leu Asn Gly Lys Glu Tyr Lys Cys Lys Val Ser Asn Lys Gly Leu Pro
        355                 360                 365

Ala Pro Ile Glu Lys Thr Ile Ser Lys Thr Lys Gly Gln Pro Arg Glu
    370                 375                 380

Pro Gln Val Cys Thr Leu Pro Pro Ser Arg Glu Glu Met Thr Lys Asn
385                 390                 395                 400

Gln Val Ser Leu Ser Cys Ala Val Lys Gly Phe Tyr Pro Ser Asp Ile
                405                 410                 415

Ala Val Glu Trp Glu Ser Asn Gly Gln Pro Glu Asn Asn Tyr Lys Thr
            420                 425                 430

Thr Pro Pro Met Leu Asp Ser Asp Gly Ser Phe Phe Leu Val Ser Lys
        435                 440                 445

Leu Thr Val Asp Lys Ser Arg Trp Gln Gln Gly Asn Val Phe Ser Cys
    450                 455                 460

Ser Val Met His Glu Ala Leu His Asn His Tyr Thr Gln Lys Ser Leu
465                 470                 475                 480

Ser Leu Ser Pro Gly
                485

<210> SEQ ID NO 37
<211> LENGTH: 5
<212> TYPE: PRT
<213> ORGANISM: Artificial Sequence
<220> FEATURE:
<223> OTHER INFORMATION: TPP-14719; 13660-13469-scFv-kih-IgG2_Fc; Chain2
      HCDR1

<400> SEQUENCE: 37

Asp Tyr Tyr Met Thr
1               5

<210> SEQ ID NO 38
<211> LENGTH: 15
<212> TYPE: PRT
<213> ORGANISM: Artificial Sequence
<220> FEATURE:
<223> OTHER INFORMATION: TPP-14719; 13660-13469-scFv-kih-IgG2_Fc; Chain2
      HCDR2

<400> SEQUENCE: 38

Ser Ile Ser Gly Gly Ser Thr Tyr Tyr Ala Asp Ser Arg Lys Gly
1               5                   10                  15

<210> SEQ ID NO 39
<211> LENGTH: 15
<212> TYPE: PRT
<213> ORGANISM: Artificial Sequence
<220> FEATURE:
<223> OTHER INFORMATION: TPP-14719; 13660-13469-scFv-kih-IgG2_Fc; Chain2
      HCDR3

<400> SEQUENCE: 39

Asp Phe Gly Val Ala Gly Trp Phe Gly Gln Tyr Gly Met Asp Val
1               5                   10                  15

<210> SEQ ID NO 40
<211> LENGTH: 14
<212> TYPE: PRT
<213> ORGANISM: Artificial Sequence
<220> FEATURE:
<223> OTHER INFORMATION: TPP-14719; 13660-13469-scFv-kih-IgG2_Fc; Chain2
      LCDR1

<400> SEQUENCE: 40

Thr Gly Ser Ser Ser Asn Ile Gly Ala Gly Tyr Asp Val His
1               5                   10

<210> SEQ ID NO 41
<211> LENGTH: 7
<212> TYPE: PRT
<213> ORGANISM: Artificial Sequence
<220> FEATURE:
<223> OTHER INFORMATION: TPP-14719; 13660-13469-scFv-kih-IgG2_Fc; Chain2
      LCDR2

<400> SEQUENCE: 41

Arg Ser Asn Gln Arg Pro Ser
1               5

<210> SEQ ID NO 42
<211> LENGTH: 10
<212> TYPE: PRT
<213> ORGANISM: Artificial Sequence
<220> FEATURE:
<223> OTHER INFORMATION: TPP-14719; 13660-13469-scFv-kih-IgG2_Fc; Chain2
      LCDR3

<400> SEQUENCE: 42

Ser Ser Tyr Ala Gly Asn Tyr Asn Leu Val
1               5                   10

<210> SEQ ID NO 43
<211> LENGTH: 1431
<212> TYPE: DNA
<213> ORGANISM: Artificial Sequence
<220> FEATURE:
<223> OTHER INFORMATION: TPP-14719; 13660-13469-scFv-kih-IgG2_Fc; Chain1

<400> SEQUENCE: 43
gaagttcagc tgctggaatc tggcggcgga ctggttcaac tggcggatc tctgagactg       60 agctgtgccg ccagcggctt cacctttagc agctacgcca tgagctgggt ccgacaggct      120
cctggcaaag ccttgagtg gtcgccaac atcaaccagg atggcagcga agaactac          180 gtggacagca tgcggggcag attcaccatc agccgggaca cagcaagaa caccctgtac       240 ctgcagatga acagcctgag agccgaggac accgccgtgt actattgcgc cagagagttc     300
gactattggg ccagggcac actggtcacc gtgacatcta gcggaggcgg aggatcaggt      360
ggcggtggaa gtggtggcgg aggttctcaa tctgtgctgg cccaacctcc tagcgcctct    420
ggaacacctg gacagagagt gaccatcagc tgtagcggca gcagcaa catcggcagc        480 aactacgtgt actggtatca gcagctgccc ggcacagccc ctaaactgct gatctacggc    540
aacaacaagc ggcctagcgg cgtgcccgat agattttctg gcagcaagag cggcacaagc    600
gccagcctgg ctattagcgg actgagatct gaggacgagg ccgactacta ttgtgccgcc    660

```
tgggacgata gcctgaacgg cagagttttt ggcggaggca ccaagctgac agtgcttgga      720
ggtggtggat caggcggtgg cggaagcggc ggaggtggaa gcggagttga atgtcctcca      780
tgtcctgctc ctccagtggc cggaccttcc gtgtttctgt tccctccaaa gcctaaggac      840
accctgatga tcagcagaac ccctgaagtg acctgcgtgg tggtggatgt gtcccacgag      900
gatcctgagg tgcagttcaa ttggtacgtg gacggcgtgg aagtgcacaa cgccaagacc      960
aagcctagag aggaacagtt caacagcacc ttcagagtgg tgtccgtgct gaccgtggtg     1020
catcaggatt ggctgaacgg caaagagtac aagtgcaagg tgtccaacaa gggcctgcct     1080
gctcctatcg agaaaaccat cagcaagaca aaggcccagc ctcgcgagcc ccaggtttac     1140
acacttcctc catgccggga agagatgacc aagaaccagg tgtccctgtg gtgcctggtc     1200
aagggcttct accccagcga tatcgccgtg gaatggagag caatggcca gcctgagaac     1260 aactacaaga ccacacctcc tatgctggac agcgacggct cattcttcct gtacagcaag     1320
ctgacagtgg acaagagcag atggcagcag ggcaacgtgt tcagctgcag cgtgatgcac     1380
gaggccctgc acaaccacta cacccagaag tccctgagcc tgtctcctgg a              1431
```

```
<210> SEQ ID NO 44
<211> LENGTH: 15
<212> TYPE: DNA
<213> ORGANISM: Artificial Sequence
<220> FEATURE:
<223> OTHER INFORMATION: TPP-14719; 13660-13469-scFv-kih-IgG2_Fc; Chain1
      HCDR1

<400> SEQUENCE: 44
agctacgcca tgagc                                                        15

<210> SEQ ID NO 45
<211> LENGTH: 51
<212> TYPE: DNA
<213> ORGANISM: Artificial Sequence
<220> FEATURE:
<223> OTHER INFORMATION: TPP-14719; 13660-13469-scFv-kih-IgG2_Fc; Chain1
      HCDR2

<400> SEQUENCE: 45
aacatcaacc aggatggcag cgagaagaac tacgtggaca gcatgcgggg c                51

<210> SEQ ID NO 46
<211> LENGTH: 12
<212> TYPE: DNA
<213> ORGANISM: Artificial Sequence
<220> FEATURE:
<223> OTHER INFORMATION: TPP-14719; 13660-13469-scFv-kih-IgG2_Fc; Chain1
      HCDR3

<400> SEQUENCE: 46
gagttcgact at                                                           12

<210> SEQ ID NO 47
<211> LENGTH: 39
<212> TYPE: DNA
<213> ORGANISM: Artificial Sequence
<220> FEATURE:
<223> OTHER INFORMATION: TPP-14719; 13660-13469-scFv-kih-IgG2_Fc; Chain1
      LCDR1

<400> SEQUENCE: 47
agcggcagca gcagcaacat cggcagcaac tacgtgtac                              39
```

<210> SEQ ID NO 48
<211> LENGTH: 21
<212> TYPE: DNA
<213> ORGANISM: Artificial Sequence
<220> FEATURE:
<223> OTHER INFORMATION: TPP-14719; 13660-13469-scFv-kih-IgG2_Fc; Chain1 LCDR2

<400> SEQUENCE: 48

```
ggcaacaaca agcggcctag c                                              21
```

<210> SEQ ID NO 49
<211> LENGTH: 33
<212> TYPE: DNA
<213> ORGANISM: Artificial Sequence
<220> FEATURE:
<223> OTHER INFORMATION: TPP-14719; 13660-13469-scFv-kih-IgG2_Fc; Chain1 LCDR3

<400> SEQUENCE: 49

```
gccgcctggg acgatagcct gaacggcaga gtt                                 33
```

<210> SEQ ID NO 50
<211> LENGTH: 1455
<212> TYPE: DNA
<213> ORGANISM: Artificial Sequence
<220> FEATURE:
<223> OTHER INFORMATION: TPP-14719; 13660-13469-scFv-kih-IgG2_Fc; Chain2

<400> SEQUENCE: 50

```
gaagttcagc tgctggaatc tggcggcgga ctggttcaac ctggcggatc tctgagactg    60
agctgtgccg ccagcggctt caccttcagc gactactaca tgacctggat cagacaggcc   120
cctggcaaag gcctggaatg ggtgtcctct atctctggcg gcagcaccta ctacgccgac   180
tccagaaagg gcagattcac catcagccgg acaacagcg agaacaccct gtacctgcag   240
atgaacagcc tgagagccga ggacaccgcc gtgtactact gcgccagaga ctttggagtg   300
gccggatggt tcggccagta cggcatggat gtttggggcc agggaaccct ggtcacagtt   360
tctagcggag gcggaggatc aggtggcggt ggatctggcg gtggtggttc tcagtctgtg   420
ctgacacagc ctcctagcgc ctctggaaca cctggccaga gagtgaccat cagctgtaca   480
ggcagcagca gcaatatcgg agccggctat gacgtgcact ggtatcagca gctgcctggc   540
acagccccta aactgctgat ctacagaagc aaccagcggc tagcggcgt gcccgataga   600
tttttctggca gcaagagcgg cacaagcgcc agcctggcta ttagcggact gagatctgag   660
gacgaggccg attactactg cagcagctac gccggcaact acaacctggt ttttggcgga   720
ggcaccaagc tgacagtgct tggtggcgga ggaagtggcg gcggaggttc aggcggtggc   780
ggaagcggag ttgaatgtcc tccatgtcct gctcctccag tggccggacc ttccgtgttt   840
ctgttccctc caaagcctaa ggacaccctg atgatcagca accccctga gtgacctgc   900
gtggtggtgg atgtgtccca cgaggatcct gaggtgcagt tcaattggta cgtggacggc   960
gtggaagtgc acaacgccaa gaccaagcct agagaggaac agttcaacag cacttcaga   1020
gtggtgtccg tgctgaccgt ggtgcatcag gattggctga acggcaaaga gtacaagtgc   1080
aaggtgtcca caagggcct gcctgctcct atcgagaaaa ccatcagcaa acaaagggc   1140
cagcctcgcg agccccaagt ctgtacactt cctccaagcc gggaagagat gaccaagaac   1200
caggtgtccc tgagctgtgc cgtgaagggc ttctaccctt ccgatatcgc cgtgaatgg   1260
gagagcaatg gccagcctga gaacaactac aagaccacac ctcctatgct ggacagcgac   1320
```

```
ggctcattct tcctggtgtc caagctgaca gtggacaaga gcagatggca gcagggcaac      1380
gtgttcagct gcagcgtgat gcacgaggcc ctgcacaacc actacaccca gaagtccctg      1440
tctctgagcc ctgga                                                       1455
```

<210> SEQ ID NO 51
<211> LENGTH: 15
<212> TYPE: DNA
<213> ORGANISM: Artificial Sequence
<220> FEATURE:
<223> OTHER INFORMATION: TPP-14719; 13660-13469-scFv-kih-IgG2_Fc; Chain2
      HCDR1

<400> SEQUENCE: 51

```
gactactaca tgacc                                                         15
```

<210> SEQ ID NO 52
<211> LENGTH: 45
<212> TYPE: DNA
<213> ORGANISM: Artificial Sequence
<220> FEATURE:
<223> OTHER INFORMATION: TPP-14719; 13660-13469-scFv-kih-IgG2_Fc; Chain2
      HCDR2

<400> SEQUENCE: 52

```
tctatctctg gcggcagcac ctactacgcc gactccagaa agggc                        45
```

<210> SEQ ID NO 53
<211> LENGTH: 45
<212> TYPE: DNA
<213> ORGANISM: Artificial Sequence
<220> FEATURE:
<223> OTHER INFORMATION: TPP-14719; 13660-13469-scFv-kih-IgG2_Fc; Chain2
      HCDR3

<400> SEQUENCE: 53

```
gactttggag tggccggatg gttcggccag tacggcatgg atgtt                        45
```

<210> SEQ ID NO 54
<211> LENGTH: 42
<212> TYPE: DNA
<213> ORGANISM: Artificial Sequence
<220> FEATURE:
<223> OTHER INFORMATION: TPP-14719; 13660-13469-scFv-kih-IgG2_Fc; Chain2
      LCDR1

<400> SEQUENCE: 54

```
acaggcagca gcagcaatat cggagccggc tatgacgtgc ac                          42
```

<210> SEQ ID NO 55
<211> LENGTH: 21
<212> TYPE: DNA
<213> ORGANISM: Artificial Sequence
<220> FEATURE:
<223> OTHER INFORMATION: TPP-14719; 13660-13469-scFv-kih-IgG2_Fc; Chain2
      LCDR2

<400> SEQUENCE: 55

```
agaagcaacc agcggcctag c                                                 21
```

<210> SEQ ID NO 56
<211> LENGTH: 30
<212> TYPE: DNA
<213> ORGANISM: Artificial Sequence
<220> FEATURE:
<223> OTHER INFORMATION: TPP-14719; 13660-13469-scFv-kih-IgG2_Fc; Chain2
      LCDR3

```
<400> SEQUENCE: 56
agcagctacg ccggcaacta caacctggtt                                     30

<210> SEQ ID NO 57
<211> LENGTH: 5
<212> TYPE: PRT
<213> ORGANISM: Artificial Sequence
<220> FEATURE:
<223> OTHER INFORMATION: TPP-13469; 484A-M010-C06-scFv-Fc-hIgG2; HCDR1

<400> SEQUENCE: 57

Asp Tyr Tyr Met Thr
1               5

<210> SEQ ID NO 58
<211> LENGTH: 15
<212> TYPE: PRT
<213> ORGANISM: Artificial Sequence
<220> FEATURE:
<223> OTHER INFORMATION: TPP-13469; 484A-M010-C06-scFv-Fc-hIgG2; HCDR2

<400> SEQUENCE: 58

Ser Ile Ser Gly Gly Ser Thr Tyr Tyr Ala Asp Ser Arg Lys Gly
1               5                   10                  15

<210> SEQ ID NO 59
<211> LENGTH: 15
<212> TYPE: PRT
<213> ORGANISM: Artificial Sequence
<220> FEATURE:
<223> OTHER INFORMATION: TPP-13469; 484A-M010-C06-scFv-Fc-hIgG2; HCDR3

<400> SEQUENCE: 59

Asp Phe Gly Val Ala Gly Trp Phe Gly Gln Tyr Gly Met Asp Val
1               5                   10                  15

<210> SEQ ID NO 60
<211> LENGTH: 14
<212> TYPE: PRT
<213> ORGANISM: Artificial Sequence
<220> FEATURE:
<223> OTHER INFORMATION: TPP-13469; 484A-M010-C06-scFv-Fc-hIgG2; LCDR1

<400> SEQUENCE: 60

Thr Gly Ser Ser Ser Asn Ile Gly Ala Gly Tyr Asp Val His
1               5                   10

<210> SEQ ID NO 61
<211> LENGTH: 7
<212> TYPE: PRT
<213> ORGANISM: Artificial Sequence
<220> FEATURE:
<223> OTHER INFORMATION: TPP-13469; 484A-M010-C06-scFv-Fc-hIgG2; LCDR2

<400> SEQUENCE: 61

Arg Ser Asn Gln Arg Pro Ser
1               5

<210> SEQ ID NO 62
<211> LENGTH: 10
<212> TYPE: PRT
<213> ORGANISM: Artificial Sequence
<220> FEATURE:
<223> OTHER INFORMATION: TPP-13469; 484A-M010-C06-scFv-Fc-hIgG2; LCDR3

<400> SEQUENCE: 62
```

Ser Ser Tyr Ala Gly Asn Tyr Asn Leu Val
1               5                   10

<210> SEQ ID NO 63
<211> LENGTH: 15
<212> TYPE: DNA
<213> ORGANISM: Artificial Sequence
<220> FEATURE:
<223> OTHER INFORMATION: TPP-13469; 484A-M010-C06-scFv-Fc-hIgG2; HCDR1

<400> SEQUENCE: 63
gactactaca tgacc                                                    15

<210> SEQ ID NO 64
<211> LENGTH: 45
<212> TYPE: DNA
<213> ORGANISM: Artificial Sequence
<220> FEATURE:
<223> OTHER INFORMATION: TPP-13469; 484A-M010-C06-scFv-Fc-hIgG2; HCDR2

<400> SEQUENCE: 64
tctatctctg gcggcagcac ctactacgcc gactccagaa agggc                   45

<210> SEQ ID NO 65
<211> LENGTH: 45
<212> TYPE: DNA
<213> ORGANISM: Artificial Sequence
<220> FEATURE:
<223> OTHER INFORMATION: TPP-13469; 484A-M010-C06-scFv-Fc-hIgG2; HCDR3

<400> SEQUENCE: 65
gactttggag tggccggatg gttcggccag tacggcatgg atgtt                   45

<210> SEQ ID NO 66
<211> LENGTH: 42
<212> TYPE: DNA
<213> ORGANISM: Artificial Sequence
<220> FEATURE:
<223> OTHER INFORMATION: TPP-13469; 484A-M010-C06-scFv-Fc-hIgG2; LCDR1

<400> SEQUENCE: 66
acaggcagca gcagcaatat cggagccggc tatgacgtgc ac                      42

<210> SEQ ID NO 67
<211> LENGTH: 21
<212> TYPE: DNA
<213> ORGANISM: Artificial Sequence
<220> FEATURE:
<223> OTHER INFORMATION: TPP-13469; 484A-M010-C06-scFv-Fc-hIgG2; LCDR2

<400> SEQUENCE: 67
agaagcaacc agcggcctag c                                             21

<210> SEQ ID NO 68
<211> LENGTH: 30
<212> TYPE: DNA
<213> ORGANISM: Artificial Sequence
<220> FEATURE:
<223> OTHER INFORMATION: TPP-13469; 484A-M010-C06-scFv-Fc-hIgG2; LCDR3

<400> SEQUENCE: 68
agcagctacg ccggcaacta caacctggtt                                    30

<210> SEQ ID NO 69
<211> LENGTH: 485

```
<212> TYPE: PRT
<213> ORGANISM: Artificial Sequence
<220> FEATURE:
<223> OTHER INFORMATION: TPP-13469; 484A-M010-C06-scFv-Fc-hIgG2; scFv

<400> SEQUENCE: 69

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Met Thr Trp Ile Arg Gln Ala Pro Gly Lys Gly Leu Glu Trp Val
        35                  40                  45

Ser Ser Ile Ser Gly Gly Ser Thr Tyr Tyr Ala Asp Ser Arg Lys Gly
    50                  55                  60

Arg Phe Thr Ile Ser Arg Asp Asn Ser Glu Asn Thr Leu Tyr Leu Gln
65                  70                  75                  80

Met Asn Ser Leu Arg Ala Glu Asp Thr Ala Val Tyr Tyr Cys Ala Arg
                85                  90                  95

Asp Phe Gly Val Ala Gly Trp Phe Gly Gln Tyr Gly Met Asp Val Trp
            100                 105                 110

Gly Gln Gly Thr Leu Val Thr Val Ser Ser Gly Gly Gly Gly Ser Gly
        115                 120                 125

Gly Gly Gly Ser Gly Gly Gly Gly Ser Gln Ser Val Leu Thr Gln Pro
    130                 135                 140

Pro Ser Ala Ser Gly Thr Pro Gly Gln Arg Val Thr Ile Ser Cys Thr
145                 150                 155                 160

Gly Ser Ser Ser Asn Ile Gly Ala Gly Tyr Asp Val His Trp Tyr Gln
                165                 170                 175

Gln Leu Pro Gly Thr Ala Pro Lys Leu Leu Ile Tyr Arg Ser Asn Gln
            180                 185                 190

Arg Pro Ser Gly Val Pro Asp Arg Phe Ser Gly Ser Lys Ser Gly Thr
        195                 200                 205

Ser Ala Ser Leu Ala Ile Ser Gly Leu Arg Ser Glu Asp Glu Ala Asp
    210                 215                 220

Tyr Tyr Cys Ser Ser Tyr Ala Gly Asn Tyr Asn Leu Val Phe Gly Gly
225                 230                 235                 240

Gly Thr Lys Leu Thr Val Leu Gly Gly Gly Gly Ser Gly Gly Gly Gly
                245                 250                 255

Ser Gly Gly Gly Gly Ser Gly Val Glu Cys Pro Pro Cys Pro Ala Pro
            260                 265                 270

Pro Val Ala Gly Pro Ser Val Phe Leu Phe Pro Pro Lys Pro Lys Asp
        275                 280                 285

Thr Leu Met Ile Ser Arg Thr Pro Glu Val Thr Cys Val Val Val Asp
    290                 295                 300

Val Ser His Glu Asp Pro Glu Val Gln Phe Asn Trp Tyr Val Asp Gly
305                 310                 315                 320

Val Glu Val His Asn Ala Lys Thr Lys Pro Arg Glu Glu Gln Phe Asn
                325                 330                 335

Ser Thr Phe Arg Val Val Ser Val Leu Thr Val Val His Gln Asp Trp
            340                 345                 350

Leu Asn Gly Lys Glu Tyr Lys Cys Lys Val Ser Asn Lys Gly Leu Pro
        355                 360                 365

Ala Pro Ile Glu Lys Thr Ile Ser Lys Thr Lys Gly Gln Pro Arg Glu
    370                 375                 380
```

```
Pro Gln Val Tyr Thr Leu Pro Pro Ser Arg Glu Glu Met Thr Lys Asn
385                 390                 395                 400

Gln Val Ser Leu Thr Cys Leu Val Lys Gly Phe Tyr Pro Ser Asp Ile
            405                 410                 415

Ala Val Glu Trp Glu Ser Asn Gly Gln Pro Glu Asn Asn Tyr Lys Thr
        420                 425                 430

Thr Pro Pro Met Leu Asp Ser Asp Gly Ser Phe Phe Leu Tyr Ser Lys
            435                 440                 445

Leu Thr Val Asp Lys Ser Arg Trp Gln Gln Gly Asn Val Phe Ser Cys
        450                 455                 460

Ser Val Met His Glu Ala Leu His Asn His Tyr Thr Gln Lys Ser Leu
465                 470                 475                 480

Ser Leu Ser Pro Gly
            485

<210> SEQ ID NO 70
<211> LENGTH: 1455
<212> TYPE: DNA
<213> ORGANISM: Artificial Sequence
<220> FEATURE:
<223> OTHER INFORMATION: TPP-13469; 484A-M010-C06-scFv-Fc-hIgG2; scFv

<400> SEQUENCE: 70
gaagttcagc tgctggaatc tggcggcgga ctggttcaac tggcggatc tctgagactg     60 agctgtgccg ccagcggctt caccttcagc gactactaca tgacctggat cagacaggcc   120
cctggcaaag gcctggaatg ggtgtcctct atctctggcg cagcaccta ctacgccgac    180 tccagaaagg gcagattcac catcagccgg acaacagcg agaacaccct gtacctgcag    240
atgaacagcc tgagagccga ggacaccgcc gtgtactact cgccagaga ctttggagtg    300 gccggatggt tcggccagta cggcatggat gtttggggcc agggaaccct ggtcacagtt   360
tctagcggag cgcgaggatc aggtggcggt ggatctggcg gtggtggttc tcagtctgtg   420
ctgacacagc ctcctagcgc tctggaaca cctggccaga gagtgaccat cagctgtaca    480
ggcagcagca gcaatatcgg agccggctat gacgtgcact ggtatcagca gctgcctggc   540
acagccccta aactgctgat ctacagaagc aaccagcggc ctagcggcgt gcccgataga   600
ttttctggca gcaagagcgg cacaagcgcc agcctggcta ttagcggact gagatctgag   660
gacgaggccg attactactg cagcagctac gccggcaact acaacctggt ttttggcgga   720
ggcaccaagc tgacagtgct tggtggcgga ggaagtggcg gcggaggttc aggcggtggc   780
ggaagcggag ttgaatgtcc tccatgtcct gctcctccag tggccggacc ttccgtgttt   840
ctgttcccct caaagcctaa ggacaccctg atgatcagca gaacccctga gtgacctgc    900 gtggtggtga tgtgtcccca cgaggatcct gaggtgcagt tcaattggta cgtggacggc   960
gtggaagtgc acaacgccaa gaccaagcct agagaggaac agttcaacag caccttcaga  1020
gtggtgtccg tgctgaccgt ggtgcatcag gattggctga acggcaaaga gtacaagtgc  1080
aaggtgtcca caagggcct gctgctcct atcgagaaaa ccatcagcaa gacaagggc     1140 cagcctcgcg agccccaggt ttacacactt cctccaagcc gggaagagat gaccaagaac  1200
caggtgtccc tgacctgcct ggtcaagggc ttctaccctt ccgatatcgc cgtggaatgg  1260
gagagcaatg gccagcctga gaacaactac aagaccacac ctcctatgct ggacagcgac  1320
ggctcattct tcctgtacag caagctgaca gtggacaaga gcagatggca gcagggcaac  1380
gtgttcagct gcagcgtgat gcacgaggcc ctgcacaacc actacaccca gaagtccctg  1440
```

```
agcctgtctc ctgga                                                     1455
```

<210> SEQ ID NO 71
<211> LENGTH: 5
<212> TYPE: PRT
<213> ORGANISM: Artificial Sequence
<220> FEATURE:
<223> OTHER INFORMATION: TPP-13654; 484A-M233-M07-scFv-Fc-hIgG2; HCDR1

<400> SEQUENCE: 71

Ile Tyr Ala Met Ser
1               5

<210> SEQ ID NO 72
<211> LENGTH: 17
<212> TYPE: PRT
<213> ORGANISM: Artificial Sequence
<220> FEATURE:
<223> OTHER INFORMATION: TPP-13654; 484A-M233-M07-scFv-Fc-hIgG2; HCDR2

<400> SEQUENCE: 72

Ala Ile Ser Gly Ser Gly Gly Ser Thr Tyr Tyr Ala Asp Ser Val Lys
1               5                   10                  15

Gly

<210> SEQ ID NO 73
<211> LENGTH: 4
<212> TYPE: PRT
<213> ORGANISM: Artificial Sequence
<220> FEATURE:
<223> OTHER INFORMATION: TPP-13654; 484A-M233-M07-scFv-Fc-hIgG2; HCDR3

<400> SEQUENCE: 73

Asp Phe Asp Tyr
1

<210> SEQ ID NO 74
<211> LENGTH: 13
<212> TYPE: PRT
<213> ORGANISM: Artificial Sequence
<220> FEATURE:
<223> OTHER INFORMATION: TPP-13654; 484A-M233-M07-scFv-Fc-hIgG2; LCDR1

<400> SEQUENCE: 74

Ser Gly Ser Ser Ser Asn Ile Gly Ser Asn Tyr Val Tyr
1               5                   10

<210> SEQ ID NO 75
<211> LENGTH: 7
<212> TYPE: PRT
<213> ORGANISM: Artificial Sequence
<220> FEATURE:
<223> OTHER INFORMATION: TPP-13654; 484A-M233-M07-scFv-Fc-hIgG2; LCDR2

<400> SEQUENCE: 75

Gly Asn Ile Asn Arg Pro Ser
1               5

<210> SEQ ID NO 76
<211> LENGTH: 11
<212> TYPE: PRT
<213> ORGANISM: Artificial Sequence
<220> FEATURE:
<223> OTHER INFORMATION: TPP-13654; 484A-M233-M07-scFv-Fc-hIgG2; LCDR3

<400> SEQUENCE: 76

Ala Ala Trp Asp Asp Ser Leu Asn Gly Arg Val
1               5                   10

<210> SEQ ID NO 77
<211> LENGTH: 15
<212> TYPE: DNA
<213> ORGANISM: Artificial Sequence
<220> FEATURE:
<223> OTHER INFORMATION: TPP-13654; 484A-M233-M07-scFv-Fc-hIgG2; HCDR1

<400> SEQUENCE: 77
atctacgcca tgagc                                                     15

<210> SEQ ID NO 78
<211> LENGTH: 51
<212> TYPE: DNA
<213> ORGANISM: Artificial Sequence
<220> FEATURE:
<223> OTHER INFORMATION: TPP-13654; 484A-M233-M07-scFv-Fc-hIgG2; HCDR2

<400> SEQUENCE: 78
gccatctctg gcagcggcgg cagcacatat tacgccgatt ctgtgaaggg c              51

<210> SEQ ID NO 79
<211> LENGTH: 12
<212> TYPE: DNA
<213> ORGANISM: Artificial Sequence
<220> FEATURE:
<223> OTHER INFORMATION: TPP-13654; 484A-M233-M07-scFv-Fc-hIgG2; HCDR3

<400> SEQUENCE: 79
gacttcgact at                                                        12

<210> SEQ ID NO 80
<211> LENGTH: 39
<212> TYPE: DNA
<213> ORGANISM: Artificial Sequence
<220> FEATURE:
<223> OTHER INFORMATION: TPP-13654; 484A-M233-M07-scFv-Fc-hIgG2; LCDR1

<400> SEQUENCE: 80
agcggcagca gcagcaacat cggcagcaac tacgtgtac                           39

<210> SEQ ID NO 81
<211> LENGTH: 21
<212> TYPE: DNA
<213> ORGANISM: Artificial Sequence
<220> FEATURE:
<223> OTHER INFORMATION: TPP-13654; 484A-M233-M07-scFv-Fc-hIgG2; LCDR2

<400> SEQUENCE: 81
ggcaacatca acagacccag c                                              21

<210> SEQ ID NO 82
<211> LENGTH: 33
<212> TYPE: DNA
<213> ORGANISM: Artificial Sequence
<220> FEATURE:
<223> OTHER INFORMATION: TPP-13654; 484A-M233-M07-scFv-Fc-hIgG2; LCDR3

<400> SEQUENCE: 82
gccgcctggg acgatagcct gaacggcaga gtt                                 33

<210> SEQ ID NO 83
<211> LENGTH: 477
<212> TYPE: PRT

<213> ORGANISM: Artificial Sequence
<220> FEATURE:
<223> OTHER INFORMATION: TPP-13654; 484A-M233-M07-scFv-Fc-hIgG2; scFv

<400> SEQUENCE: 83

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Phe Asp Tyr Trp Gly Gln Gly Thr Leu Val Thr Val Thr
            100                 105                 110

Ser Ser Gly Gly Gly Gly Ser Gly Gly Gly Gly Ser Gly Gly Gly Gly
        115                 120                 125

Ser Gln Ser Val Leu Thr Gln Pro Pro Ser Ala Ser Gly Thr Pro Gly
    130                 135                 140

Gln Arg Val Thr Ile Ser Cys Ser Gly Ser Ser Ser Asn Ile Gly Ser
145                 150                 155                 160

Asn Tyr Val Tyr Trp Tyr Gln Gln Leu Pro Gly Thr Ala Pro Lys Leu
                165                 170                 175

Leu Ile Tyr Gly Asn Ile Asn Arg Pro Ser Gly Val Pro Asp Arg Phe
            180                 185                 190

Ser Gly Ser Lys Ser Gly Thr Ser Ala Ser Leu Ala Ile Ser Gly Leu
        195                 200                 205

Arg Ser Glu Asp Glu Ala Asp Tyr Tyr Cys Ala Ala Trp Asp Asp Ser
    210                 215                 220

Leu Asn Gly Arg Val Phe Gly Gly Gly Thr Lys Leu Thr Val Leu Gly
225                 230                 235                 240

Gly Gly Gly Ser Gly Gly Gly Gly Ser Gly Gly Gly Ser Gly Val
                245                 250                 255

Glu Cys Pro Pro Cys Pro Ala Pro Pro Val Ala Gly Pro Ser Val Phe
            260                 265                 270

Leu Phe Pro Pro Lys Pro Lys Asp Thr Leu Met Ile Ser Arg Thr Pro
        275                 280                 285

Glu Val Thr Cys Val Val Val Asp Val Ser His Glu Asp Pro Glu Val
    290                 295                 300

Gln Phe Asn Trp Tyr Val Asp Gly Val Glu Val His Asn Ala Lys Thr
305                 310                 315                 320

Lys Pro Arg Glu Glu Gln Phe Asn Ser Thr Phe Arg Val Val Ser Val
                325                 330                 335

Leu Thr Val Val His Gln Asp Trp Leu Asn Gly Lys Glu Tyr Lys Cys
            340                 345                 350

Lys Val Ser Asn Lys Gly Leu Pro Ala Pro Ile Glu Lys Thr Ile Ser
        355                 360                 365

Lys Thr Lys Gly Gln Pro Arg Glu Pro Gln Val Tyr Thr Leu Pro Pro
    370                 375                 380

Ser Arg Glu Glu Met Thr Lys Asn Gln Val Ser Leu Thr Cys Leu Val
```

```
385                 390                 395                 400
Lys Gly Phe Tyr Pro Ser Asp Ile Ala Val Glu Trp Glu Ser Asn Gly
                405                 410                 415

Gln Pro Glu Asn Asn Tyr Lys Thr Thr Pro Pro Met Leu Asp Ser Asp
                420                 425                 430

Gly Ser Phe Phe Leu Tyr Ser Lys Leu Thr Val Asp Lys Ser Arg Trp
                435                 440                 445

Gln Gln Gly Asn Val Phe Ser Cys Ser Val Met His Glu Ala Leu His
            450                 455                 460

Asn His Tyr Thr Gln Lys Ser Leu Ser Leu Ser Pro Gly
465                 470                 475

<210> SEQ ID NO 84
<211> LENGTH: 1431
<212> TYPE: DNA
<213> ORGANISM: Artificial Sequence
<220> FEATURE:
<223> OTHER INFORMATION: TPP-13654; 484A-M233-M07-scFv-Fc-hIgG2; scFv

<400> SEQUENCE: 84
gaagttcagc tgctggaatc tggcggcgga ctggttcaac tggcggatc tctgagactg      60
agctgtgccg ccagcggctt cacctttagc atctacgcca tgagctgggt ccgacaggcc    120
cctggaaaag gccttgaatg ggtgtccgcc atctctggca gcggcggcag cacatattac    180
gccgattctg tgaagggcag attcaccatc agccgggaca acagcaagaa caccctgtac    240
ctgcagatga acagcctgag agccgaggac accgccgtgt actattgcgc cagagacttc    300
gactattggg gccagggcac actggtcacc gtgacatcta gcggaggcgg aggatcaggt    360
ggcggtggaa gtggtggcgg aggttctcag tctgtgctga cacagcctcc tagcgcctct    420
ggaacacctg gccagagagt gaccatcagc tgtagcggca gcagcaa catcggcagc       480
aactacgtgt actggtatca gcagctgccc ggcacagccc ctaaactgct gatctacggc    540
aacatcaaca gacccagcgg cgtgcccgat agattcagcg gctctaagtc tggcacaagc    600
gccagcctgg ccatcagcgg actgagatct gaggacgagg ccgactacta ttgtgccgcc    660
tgggacgata gcctgaacgg cagagttttt ggcgaaggcc caagctgac agtgcttgga    720
ggtggtggat caggcggtgg cggaagcggc ggaggtggaa gcggagttga atgtcctcca    780
tgtcctgctc ctccagtggc cggaccttcc gtgtttctgt tccctccaaa gcctaaggac    840
accctgatga tcagcagaac ccctgaagtg acctgcgtgg tggtggatgt gtcccacgag    900
gatcctgagg tgcagttcaa ttggtacgtg acggcgtgg aagtgcacaa cgccaagacc    960
aagcctagag aggaacagtt caacagcacc ttcagagtgg tgtccgtgct gaccgtggtg   1020
catcaggatt ggctgaacgg caaagagtac aagtgcaagg tgtccaacaa gggcctgcct   1080
gctcctatcg agaaaaccat cagcaagaca aagggccagc ctcgcgagcc ccaggtttac   1140
acacttcctc caagccggga agagatgacc aagaaccagg tgtccctgac tgcctggtc    1200
aagggcttct acccttccga tatcgccgtg gaatgggaga gcaatggcca gcctgagaac   1260
aactacaaga ccacacctcc tatgctggac agcgacggct cattcttcct gtacagcaag   1320
ctgacagtgg acaagagcag atggcagcag ggcaacgtgt tcagctgcag cgtgatgcac   1380
gaggccctgc acaaccacta cacccagaag tccctgagcc tgtctcctgg a            1431

<210> SEQ ID NO 85
<211> LENGTH: 5
<212> TYPE: PRT
```

```
<213> ORGANISM: Artificial Sequence
<220> FEATURE:
<223> OTHER INFORMATION: TPP-13660; 484A-M232-A14-scFv-Fc-hIgG2; HCDR1

<400> SEQUENCE: 85

Ser Tyr Ala Met Ser
1               5

<210> SEQ ID NO 86
<211> LENGTH: 17
<212> TYPE: PRT
<213> ORGANISM: Artificial Sequence
<220> FEATURE:
<223> OTHER INFORMATION: TPP-13660; 484A-M232-A14-scFv-Fc-hIgG2; HCDR2

<400> SEQUENCE: 86

Asn Ile Asn Gln Asp Gly Ser Glu Lys Asn Tyr Val Asp Ser Met Arg
1               5                   10                  15

Gly

<210> SEQ ID NO 87
<211> LENGTH: 4
<212> TYPE: PRT
<213> ORGANISM: Artificial Sequence
<220> FEATURE:
<223> OTHER INFORMATION: TPP-13660; 484A-M232-A14-scFv-Fc-hIgG2; HCDR3

<400> SEQUENCE: 87

Glu Phe Asp Tyr
1

<210> SEQ ID NO 88
<211> LENGTH: 13
<212> TYPE: PRT
<213> ORGANISM: Artificial Sequence
<220> FEATURE:
<223> OTHER INFORMATION: TPP-13660; 484A-M232-A14-scFv-Fc-hIgG2; LCDR1

<400> SEQUENCE: 88

Ser Gly Ser Ser Ser Asn Ile Gly Ser Asn Tyr Val Tyr
1               5                   10

<210> SEQ ID NO 89
<211> LENGTH: 7
<212> TYPE: PRT
<213> ORGANISM: Artificial Sequence
<220> FEATURE:
<223> OTHER INFORMATION: TPP-13660; 484A-M232-A14-scFv-Fc-hIgG2; LCDR2

<400> SEQUENCE: 89

Gly Asn Asn Lys Arg Pro Ser
1               5

<210> SEQ ID NO 90
<211> LENGTH: 11
<212> TYPE: PRT
<213> ORGANISM: Artificial Sequence
<220> FEATURE:
<223> OTHER INFORMATION: TPP-13660; 484A-M232-A14-scFv-Fc-hIgG2; LCDR3

<400> SEQUENCE: 90

Ala Ala Trp Asp Asp Ser Leu Asn Gly Arg Val
1               5                   10

<210> SEQ ID NO 91
<211> LENGTH: 15
```

```
<212> TYPE: DNA
<213> ORGANISM: Artificial Sequence
<220> FEATURE:
<223> OTHER INFORMATION: TPP-13660; 484A-M232-A14-scFv-Fc-hIgG2; HCDR1

<400> SEQUENCE: 91
agctacgcca tgagc                                                          15

<210> SEQ ID NO 92
<211> LENGTH: 51
<212> TYPE: DNA
<213> ORGANISM: Artificial Sequence
<220> FEATURE:
<223> OTHER INFORMATION: TPP-13660; 484A-M232-A14-scFv-Fc-hIgG2; HCDR2

<400> SEQUENCE: 92
aacatcaacc aggatggcag cgagaagaac tacgtggaca gcatgcgggg c                  51

<210> SEQ ID NO 93
<211> LENGTH: 12
<212> TYPE: DNA
<213> ORGANISM: Artificial Sequence
<220> FEATURE:
<223> OTHER INFORMATION: TPP-13660; 484A-M232-A14-scFv-Fc-hIgG2; HCDR3

<400> SEQUENCE: 93
gagttcgact at                                                             12

<210> SEQ ID NO 94
<211> LENGTH: 39
<212> TYPE: DNA
<213> ORGANISM: Artificial Sequence
<220> FEATURE:
<223> OTHER INFORMATION: TPP-13660; 484A-M232-A14-scFv-Fc-hIgG2; LCDR1

<400> SEQUENCE: 94
agcggcagca gcagcaacat cggcagcaac tacgtgtac                                39

<210> SEQ ID NO 95
<211> LENGTH: 21
<212> TYPE: DNA
<213> ORGANISM: Artificial Sequence
<220> FEATURE:
<223> OTHER INFORMATION: TPP-13660; 484A-M232-A14-scFv-Fc-hIgG2; LCDR2

<400> SEQUENCE: 95
ggcaacaaca agcggcctag c                                                   21

<210> SEQ ID NO 96
<211> LENGTH: 33
<212> TYPE: DNA
<213> ORGANISM: Artificial Sequence
<220> FEATURE:
<223> OTHER INFORMATION: TPP-13660; 484A-M232-A14-scFv-Fc-hIgG2; LCDR3

<400> SEQUENCE: 96
gccgcctggg acgatagcct gaacggcaga gtt                                      33

<210> SEQ ID NO 97
<211> LENGTH: 477
<212> TYPE: PRT
<213> ORGANISM: Artificial Sequence
<220> FEATURE:
<223> OTHER INFORMATION: TPP-13660; 484A-M232-A14-scFv-Fc-hIgG2; scFv

<400> SEQUENCE: 97
```

-continued

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ala Asn Ile Asn Gln Asp Gly Ser Glu Lys Asn Tyr Val Asp Ser Met
50                      55                  60

Arg Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Phe Asp Tyr Trp Gly Gln Gly Thr Leu Val Thr Val Thr
            100                 105                 110

Ser Ser Gly Gly Gly Gly Ser Gly Gly Gly Gly Ser Gly Gly Gly Gly
        115                 120                 125

Ser Gln Ser Val Leu Ala Gln Pro Pro Ser Ala Ser Gly Thr Pro Gly
    130                 135                 140

Gln Arg Val Thr Ile Ser Cys Ser Gly Ser Ser Ser Asn Ile Gly Ser
145                 150                 155                 160

Asn Tyr Val Tyr Trp Tyr Gln Gln Leu Pro Gly Thr Ala Pro Lys Leu
                165                 170                 175

Leu Ile Tyr Gly Asn Asn Lys Arg Pro Ser Gly Val Pro Asp Arg Phe
            180                 185                 190

Ser Gly Ser Lys Ser Gly Thr Ser Ala Ser Leu Ala Ile Ser Gly Leu
        195                 200                 205

Arg Ser Glu Asp Glu Ala Asp Tyr Tyr Cys Ala Ala Trp Asp Asp Ser
210                 215                 220

Leu Asn Gly Arg Val Phe Gly Gly Gly Thr Lys Leu Thr Val Leu Gly
225                 230                 235                 240

Gly Gly Gly Ser Gly Gly Gly Gly Ser Gly Gly Gly Gly Ser Gly Val
                245                 250                 255

Glu Cys Pro Pro Cys Pro Ala Pro Pro Val Ala Gly Pro Ser Val Phe
            260                 265                 270

Leu Phe Pro Pro Lys Pro Lys Asp Thr Leu Met Ile Ser Arg Thr Pro
        275                 280                 285

Glu Val Thr Cys Val Val Val Asp Val Ser His Glu Asp Pro Glu Val
    290                 295                 300

Gln Phe Asn Trp Tyr Val Asp Gly Val Glu Val His Asn Ala Lys Thr
305                 310                 315                 320

Lys Pro Arg Glu Glu Gln Phe Asn Ser Thr Phe Arg Val Val Ser Val
                325                 330                 335

Leu Thr Val Val His Gln Asp Trp Leu Asn Gly Lys Glu Tyr Lys Cys
            340                 345                 350

Lys Val Ser Asn Lys Gly Leu Pro Ala Pro Ile Glu Lys Thr Ile Ser
        355                 360                 365

Lys Thr Lys Gly Gln Pro Arg Glu Pro Gln Val Tyr Thr Leu Pro Pro
    370                 375                 380

Ser Arg Glu Glu Met Thr Lys Asn Gln Val Ser Leu Thr Cys Leu Val
385                 390                 395                 400

Lys Gly Phe Tyr Pro Ser Asp Ile Ala Val Glu Trp Glu Ser Asn Gly
                405                 410                 415

Gln Pro Glu Asn Asn Tyr Lys Thr Thr Pro Pro Met Leu Asp Ser Asp
```

```
            420              425              430
Gly Ser Phe Phe Leu Tyr Ser Lys Leu Thr Val Asp Lys Ser Arg Trp
            435              440              445

Gln Gln Gly Asn Val Phe Ser Cys Ser Val Met His Glu Ala Leu His
    450              455              460

Asn His Tyr Thr Gln Lys Ser Leu Ser Leu Ser Pro Gly
465             470              475
```

```
<210> SEQ ID NO 98
<211> LENGTH: 1431
<212> TYPE: DNA
<213> ORGANISM: Artificial Sequence
<220> FEATURE:
<223> OTHER INFORMATION: TPP-13660; 484A-M232-A14-scFv-Fc-hIgG2; scFv

<400> SEQUENCE: 98
```

| | | | | | |
|---|---|---|---|---|---|
| gaagttcagc | tgctggaatc | tggcggcgga | ctggttcaac | ctggcggatc | tctgagactg | 60 |
| agctgtgccg | ccagcggctt | cacctttagc | agctacgcca | tgagctgggt | ccgacaggct | 120 |
| cctggcaaag | ccttgagtg | gtcgccaac | atcaaccagg | atggcagcga | agaactac | 180 |
| gtggacagca | tgcggggcag | attcaccatc | agcggaca | acagcaagaa | caccctgtac | 240 |
| ctgcagatga | acagcctgag | agccgaggac | accgccgtgt | actattgcgc | cagagagttc | 300 |
| gactattggg | gccagggcac | actggtcacc | gtgacatcta | gcggaggcgg | aggatcaggt | 360 |
| ggcggtggaa | gtggtggcgg | aggttctcaa | tctgtgctgg | cccaacctcc | tagcgcctct | 420 |
| ggaacacctg | gacagagagt | gaccatcagc | tgtagcggca | gcagcagcaa | catcggcagc | 480 |
| aactacgtgt | actggtatca | gcagctgccc | ggcacagccc | ctaaactgct | gatctacggc | 540 |
| aacaacaagc | ggcctagcgg | cgtgcccgat | agattttctg | gcagcaagag | cggcacaagc | 600 |
| gccagcctgg | ctattagcgg | actgagatct | gaggacgagg | ccgactacta | ttgtgccgcc | 660 |
| tgggacgata | gcctgaacgg | cagagttttt | ggcggaggca | ccaagctgac | agtgcttgga | 720 |
| ggtggtggat | caggcggtgg | cggaagcggc | ggaggtggaa | gcggagttga | atgtcctcca | 780 |
| tgtcctgctc | ctccagtggc | cggaccttcc | gtgtttctgt | tccctccaaa | gcctaaggac | 840 |
| accctgatga | tcagcagaac | ccctgaagtg | acctgcgtgg | tggtggatgt | gtcccacgag | 900 |
| gatcctgagg | tgcagttcaa | ttggtacgtg | gacggcgtgg | aagtgcacaa | cgccaagacc | 960 |
| aagcctagag | aggaacagtt | caacagcacc | ttcagagtg | tgtccgtgct | gaccgtggtg | 1020 |
| catcaggatt | ggctgaacgg | caaagagtac | aagtgcaagg | tgtccaacaa | gggcctgcct | 1080 |
| gctcctatcg | agaaaaccat | cagcaagaca | aagggccagc | ctcgcgagcc | ccaggtttac | 1140 |
| acacttcctc | caagccggga | agagatgacc | aagaaccagg | tgtccctgac | ctgcctggtc | 1200 |
| aagggcttct | acccttccga | tatcgccgtg | gaatgggaga | gcaatggcca | gcctgagaac | 1260 |
| aactacaaga | ccacacctcc | tatgctggac | agcgacggct | cattcttcct | gtacagcaag | 1320 |
| ctgacagtgg | acaagagcag | atggcagcag | ggcaacgtgt | tcagctgcag | cgtgatgcac | 1380 |
| gaggccctgc | acaaccacta | cacccagaag | tccctgagcc | tgtctcctgg | a | 1431 |

```
<210> SEQ ID NO 99
<211> LENGTH: 5
<212> TYPE: PRT
<213> ORGANISM: Artificial Sequence
<220> FEATURE:
<223> OTHER INFORMATION: TPP-13667; 484A-M198-J22-scFv-Fc-hIgG2; HCDR1

<400> SEQUENCE: 99
```

Asn Ala Trp Met Asn
1               5

<210> SEQ ID NO 100
<211> LENGTH: 17
<212> TYPE: PRT
<213> ORGANISM: Artificial Sequence
<220> FEATURE:
<223> OTHER INFORMATION: TPP-13667; 484A-M198-J22-scFv-Fc-hIgG2; HCDR2

<400> SEQUENCE: 100

Ser Ile Ser Ser Ser Ser Ser Tyr Ile Tyr Tyr Ala Asp Ser Val Lys
1               5                   10                  15

Gly

<210> SEQ ID NO 101
<211> LENGTH: 13
<212> TYPE: PRT
<213> ORGANISM: Artificial Sequence
<220> FEATURE:
<223> OTHER INFORMATION: TPP-13667; 484A-M198-J22-scFv-Fc-hIgG2; HCDR3

<400> SEQUENCE: 101

Ala Val Ala Ala Gly Gly Met Phe Trp Gly Leu Asp Gln
1               5                   10

<210> SEQ ID NO 102
<211> LENGTH: 13
<212> TYPE: PRT
<213> ORGANISM: Artificial Sequence
<220> FEATURE:
<223> OTHER INFORMATION: TPP-13667; 484A-M198-J22-scFv-Fc-hIgG2; LCDR1

<400> SEQUENCE: 102

Ser Gly Ser Arg Ser Asn Ile Gly Ser Asn Ser Val His
1               5                   10

<210> SEQ ID NO 103
<211> LENGTH: 7
<212> TYPE: PRT
<213> ORGANISM: Artificial Sequence
<220> FEATURE:
<223> OTHER INFORMATION: TPP-13667; 484A-M198-J22-scFv-Fc-hIgG2; LCDR2

<400> SEQUENCE: 103

Gly Asn Ser Asn Arg Pro Ser
1               5

<210> SEQ ID NO 104
<211> LENGTH: 12
<212> TYPE: PRT
<213> ORGANISM: Artificial Sequence
<220> FEATURE:
<223> OTHER INFORMATION: TPP-13667; 484A-M198-J22-scFv-Fc-hIgG2; LCDR3

<400> SEQUENCE: 104

Gln Ser Tyr Asp Ser Ser Leu Asn Asp His Val Val
1               5                   10

<210> SEQ ID NO 105
<211> LENGTH: 15
<212> TYPE: DNA
<213> ORGANISM: Artificial Sequence
<220> FEATURE:
<223> OTHER INFORMATION: TPP-13667; 484A-M198-J22-scFv-Fc-hIgG2; HCDR1

<400> SEQUENCE: 105
aacgcctgga tgaac                                            15

<210> SEQ ID NO 106
<211> LENGTH: 51
<212> TYPE: DNA
<213> ORGANISM: Artificial Sequence
<220> FEATURE:
<223> OTHER INFORMATION: TPP-13667; 484A-M198-J22-scFv-Fc-hIgG2; HCDR2

<400> SEQUENCE: 106
agcatcagca gcagctccag ctacatctac tacgccgaca gcgtgaaggg c    51

<210> SEQ ID NO 107
<211> LENGTH: 39
<212> TYPE: DNA
<213> ORGANISM: Artificial Sequence
<220> FEATURE:
<223> OTHER INFORMATION: TPP-13667; 484A-M198-J22-scFv-Fc-hIgG2; HCDR3

<400> SEQUENCE: 107
gctgttgctg ccggcggaat gttttggggc cttgatcaa                  39

<210> SEQ ID NO 108
<211> LENGTH: 39
<212> TYPE: DNA
<213> ORGANISM: Artificial Sequence
<220> FEATURE:
<223> OTHER INFORMATION: TPP-13667; 484A-M198-J22-scFv-Fc-hIgG2; LCDR1

<400> SEQUENCE: 108
agcggcagca gaagcaacat cggctccaac agcgtgcac                  39

<210> SEQ ID NO 109
<211> LENGTH: 21
<212> TYPE: DNA
<213> ORGANISM: Artificial Sequence
<220> FEATURE:
<223> OTHER INFORMATION: TPP-13667; 484A-M198-J22-scFv-Fc-hIgG2; LCDR2

<400> SEQUENCE: 109
ggcaacagca acagacccag c                                     21

<210> SEQ ID NO 110
<211> LENGTH: 36
<212> TYPE: DNA
<213> ORGANISM: Artificial Sequence
<220> FEATURE:
<223> OTHER INFORMATION: TPP-13667; 484A-M198-J22-scFv-Fc-hIgG2; LCDR3

<400> SEQUENCE: 110
cagtcctacg acagcagcct gaacgatcac gtggtg                     36

<210> SEQ ID NO 111
<211> LENGTH: 487
<212> TYPE: PRT
<213> ORGANISM: Artificial Sequence
<220> FEATURE:
<223> OTHER INFORMATION: TPP-13667; 484A-M198-J22-scFv-Fc-hIgG2; scFv

<400> SEQUENCE: 111

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Ala
            20                  25                  30

```
Trp Met Asn Trp Val Arg Gln Ala Pro Gly Lys Gly Leu Glu Trp Val
        35                  40                  45

Ser Ser Ile Ser Ser Ser Ser Tyr Ile Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Ala Val Ala Ala Gly Gly Met Phe Trp Gly Leu Asp Gln Trp
                100                 105                 110

Gly Gln Gly Thr Leu Val Thr Val Thr Ser Ser Gly Gly Gly Gly Ser
                115                 120                 125

Gly Gly Gly Gly Ser Gly Gly Gly Ser Gln Ser Val Leu Thr Gln
 130                 135                 140

Pro Pro Ser Ala Ser Gly Thr Pro Gly Gln Arg Val Thr Ile Ser Cys
145                 150                 155                 160

Ser Gly Ser Arg Ser Asn Ile Gly Ser Asn Ser Val His Trp Tyr Gln
                165                 170                 175

Gln Leu Pro Gly Thr Ala Pro Lys Leu Leu Ile Tyr Gly Asn Ser Asn
                180                 185                 190

Arg Pro Ser Gly Val Pro Asp Arg Phe Ser Gly Ser Lys Ser Gly Thr
                195                 200                 205

Ser Ala Ser Leu Ala Ile Ser Gly Leu Arg Ser Glu Asp Glu Ala Asp
210                 215                 220

Tyr Tyr Cys Gln Ser Tyr Asp Ser Ser Leu Asn Asp His Val Val Phe
225                 230                 235                 240

Gly Gly Gly Thr Lys Leu Thr Val Leu Gly Gly Gly Ser Gly Gly
                245                 250                 255

Gly Gly Ser Gly Gly Gly Ser Gly Val Glu Cys Pro Pro Cys Pro
                260                 265                 270

Ala Pro Pro Val Ala Gly Pro Ser Val Phe Leu Phe Pro Pro Lys Pro
                275                 280                 285

Lys Asp Thr Leu Met Ile Ser Arg Thr Pro Glu Val Thr Cys Val Val
290                 295                 300

Val Asp Val Ser His Glu Asp Pro Glu Val Gln Phe Asn Trp Tyr Val
305                 310                 315                 320

Asp Gly Val Glu Val His Asn Ala Lys Thr Lys Pro Arg Glu Glu Gln
                325                 330                 335

Phe Asn Ser Thr Phe Arg Val Val Ser Val Leu Thr Val Val His Gln
                340                 345                 350

Asp Trp Leu Asn Gly Lys Glu Tyr Lys Cys Lys Val Ser Asn Lys Gly
                355                 360                 365

Leu Pro Ala Pro Ile Glu Lys Thr Ile Ser Lys Thr Lys Gly Gln Pro
                370                 375                 380

Arg Glu Pro Gln Val Tyr Thr Leu Pro Pro Ser Arg Glu Glu Met Thr
385                 390                 395                 400

Lys Asn Gln Val Ser Leu Thr Cys Leu Val Lys Gly Phe Tyr Pro Ser
                405                 410                 415

Asp Ile Ala Val Glu Trp Glu Ser Asn Gly Gln Pro Glu Asn Asn Tyr
                420                 425                 430

Lys Thr Thr Pro Pro Met Leu Asp Ser Asp Gly Ser Phe Phe Leu Tyr
                435                 440                 445

Ser Lys Leu Thr Val Asp Lys Ser Arg Trp Gln Gln Gly Asn Val Phe
```

```
                450             455             460
Ser Cys Ser Val Met His Glu Ala Leu His Asn His Tyr Thr Gln Lys
465                 470             475                 480
Ser Leu Ser Leu Ser Pro Gly
                485

<210> SEQ ID NO 112
<211> LENGTH: 1461
<212> TYPE: DNA
<213> ORGANISM: Artificial Sequence
<220> FEATURE:
<223> OTHER INFORMATION: TPP-13667; 484A-M198-J22-scFv-Fc-hIgG2; scFv

<400> SEQUENCE: 112
```

| | | | | | |
|---|---|---|---|---|---|
| gaagttcagc | tgctggaatc | tggcggcgga | ctggttcaac | ctggcggatc | tctgagactg | 60 |
| agctgtgccg | ccagcggctt | cacctttagc | aacgcctgga | tgaactgggt | ccgacaggcc | 120 |
| cctggaaaag | gcctggaatg | ggtgtccagc | atcagcagca | gctccagcta | catctactac | 180 |
| gccgacagcg | tgaagggcag | attcaccatc | agccgggaca | acagcaagaa | caccctgtac | 240 |
| ctgcagatga | acagcctgag | agccgaggac | accgccgtgt | actattgtgc | cagagctgtt | 300 |
| gctgccggcg | gaatgttttg | gggccttgat | caatggggcc | agggcaccct | ggtcacagtg | 360 |
| acatctagcg | gaggcggagg | atcaggtggc | ggtggaagtg | gtggcggagg | ttctcagtct | 420 |
| gtgctgacac | agcctcctag | cgcctctgga | acacctggcc | agagagtgac | catcagctgt | 480 |
| agcggcagca | gaagcaacat | cggctccaac | agcgtgcact | ggtatcagca | gctgcctggc | 540 |
| acagccccta | actgctgat | ctacggcaac | agcaacagac | cagcggcgt | gcccgataga | 600 |
| ttcagcggct | ctaagtctgg | cacctctgcc | agcctggcca | tctctggcct | gagatctgag | 660 |
| gacgaggccg | actactactg | ccagtcctac | gacagcagcc | tgaacgatca | cgtggtgttt | 720 |
| ggcggaggca | ccaagctgac | agttcttgga | ggtggtggaa | gtggcggagg | cggaagcggt | 780 |
| ggtggtggat | ctggtgttga | atgtcctcca | tgtcctgctc | ctccagtggc | cggaccttcc | 840 |
| gtgtttctgt | tccctccaaa | gcctaaggac | accctgatga | tcagcagaac | ccctgaagtg | 900 |
| acctgcgtgg | tggtggatgt | gtcccacgag | gatcctgagg | tgcagttcaa | ttggtacgtg | 960 |
| gacggcgtgg | aagtgcacaa | cgccaagacc | aagcctagag | aggaacagtt | caacagcacc | 1020 |
| ttcagagtgg | tgtccgtgct | gaccgtggtg | catcaggatt | ggctgaacgg | caaagagtac | 1080 |
| aagtgcaagg | tgtccaacaa | gggcctgcct | gctcctatcg | agaaaaccat | cagcaagaca | 1140 |
| aagggccagc | ctcgcgagcc | ccaggtttac | acacttcctc | caagccggga | agagatgacc | 1200 |
| aagaaccagg | tgtccctgac | ctgcctggtc | aagggcttct | acccttccga | tatcgccgtg | 1260 |
| gaatgggaga | gcaatggcca | gcctgagaac | aactacaaga | ccacacctcc | tatgctggac | 1320 |
| agcgacggct | cattcttcct | gtacagcaag | ctgacagtgg | acaagagcag | atggcagcag | 1380 |
| ggcaacgtgt | tcagctgcag | cgtgatgcac | gaggccctgc | acaaccacta | cacccagaag | 1440 |
| tccctgagcc | tgtctcctgg | a | | | | 1461 |

```
<210> SEQ ID NO 113
<211> LENGTH: 621
<212> TYPE: PRT
<213> ORGANISM: Artificial Sequence
<220> FEATURE:
<223> OTHER INFORMATION: TPP-3188; hROR1-Fc antigen

<400> SEQUENCE: 113

Gln Glu Thr Glu Leu Ser Val Ser Ala Glu Leu Val Pro Thr Ser Ser
```

```
1               5                   10                  15
Trp Asn Ile Ser Ser Glu Leu Asn Lys Asp Ser Tyr Leu Thr Leu Asp
                20                  25                  30

Glu Pro Met Asn Asn Ile Thr Thr Ser Leu Gly Gln Thr Ala Glu Leu
            35                  40                  45

His Cys Lys Val Ser Gly Asn Pro Pro Thr Ile Arg Trp Phe Lys
        50                  55                  60

Asn Asp Ala Pro Val Val Gln Glu Pro Arg Arg Leu Ser Phe Arg Ser
65                  70                  75                  80

Thr Ile Tyr Gly Ser Arg Leu Arg Ile Arg Asn Leu Asp Thr Asp
                85                  90                  95

Thr Gly Tyr Phe Gln Cys Val Ala Thr Asn Gly Lys Glu Val Val Ser
                100                 105                 110

Ser Thr Gly Val Leu Phe Val Lys Phe Gly Pro Pro Thr Ala Ser
            115                 120                 125

Pro Gly Tyr Ser Asp Glu Tyr Glu Glu Asp Gly Phe Cys Gln Pro Tyr
            130                 135                 140

Arg Gly Ile Ala Cys Ala Arg Phe Ile Gly Asn Arg Thr Val Tyr Met
145                 150                 155                 160

Glu Ser Leu His Met Gln Gly Glu Ile Glu Asn Gln Ile Thr Ala Ala
                165                 170                 175

Phe Thr Met Ile Gly Thr Ser Ser His Leu Ser Asp Lys Cys Ser Gln
                180                 185                 190

Phe Ala Ile Pro Ser Leu Cys His Tyr Ala Phe Pro Tyr Cys Asp Glu
            195                 200                 205

Thr Ser Ser Val Pro Lys Pro Arg Asp Leu Cys Arg Asp Glu Cys Glu
    210                 215                 220

Ile Leu Glu Asn Val Leu Cys Gln Thr Glu Tyr Ile Phe Ala Arg Ser
225                 230                 235                 240

Asn Pro Met Ile Leu Met Arg Leu Lys Leu Pro Asn Cys Glu Asp Leu
                245                 250                 255

Pro Gln Pro Glu Ser Pro Glu Ala Ala Asn Cys Ile Arg Ile Gly Ile
            260                 265                 270

Pro Met Ala Asp Pro Ile Asn Lys Asn His Lys Cys Tyr Asn Ser Thr
        275                 280                 285

Gly Val Asp Tyr Arg Gly Thr Val Ser Val Thr Lys Ser Gly Arg Gln
            290                 295                 300

Cys Gln Pro Trp Asn Ser Gln Tyr Pro His Thr His Thr Phe Thr Ala
305                 310                 315                 320

Leu Arg Phe Pro Glu Leu Asn Gly Gly His Ser Tyr Cys Arg Asn Pro
            325                 330                 335

Gly Asn Gln Lys Glu Ala Pro Trp Cys Phe Thr Leu Asp Glu Asn Phe
        340                 345                 350

Lys Ser Asp Leu Cys Asp Ile Pro Ala Cys Asp Ser Lys Asp Ser Lys
            355                 360                 365

Glu Lys Asn Lys Met Glu Gly Gly Ser Ile Glu Gly Arg Met Asp
        370                 375                 380

Pro Lys Ser Cys Asp Lys Thr His Thr Cys Pro Pro Cys Pro Ala Pro
385                 390                 395                 400

Glu Leu Leu Gly Gly Pro Ser Val Phe Leu Phe Pro Pro Lys Pro Lys
                405                 410                 415

Asp Thr Leu Met Ile Ser Arg Thr Pro Glu Val Thr Cys Val Val Val
                420                 425                 430
```

```
Asp Val Ser His Glu Asp Pro Glu Val Lys Phe Asn Trp Tyr Val Asp
            435                 440                 445

Gly Val Glu Val His Asn Ala Lys Thr Lys Pro Arg Glu Glu Gln Tyr
    450                 455                 460

Asn Ser Thr Tyr Arg Val Val Ser Val Leu Thr Val Leu His Gln Asp
465                 470                 475                 480

Trp Leu Asn Gly Lys Glu Tyr Lys Cys Lys Val Ser Asn Lys Ala Leu
                485                 490                 495

Pro Ala Pro Ile Glu Lys Thr Ile Ser Lys Ala Lys Gly Gln Pro Arg
            500                 505                 510

Glu Pro Gln Val Tyr Thr Leu Pro Pro Ser Arg Glu Met Thr Lys
            515                 520                 525

Asn Gln Val Ser Leu Thr Cys Leu Val Lys Gly Phe Tyr Pro Ser Asp
            530                 535                 540

Ile Ala Val Glu Trp Glu Ser Asn Gly Gln Pro Glu Asn Asn Tyr Lys
545                 550                 555                 560

Thr Thr Pro Pro Val Leu Asp Ser Asp Gly Ser Phe Phe Leu Tyr Ser
                565                 570                 575

Lys Leu Thr Val Asp Lys Ser Arg Trp Gln Gln Gly Asn Val Phe Ser
            580                 585                 590

Cys Ser Val Met His Glu Ala Leu His Asn His Tyr Thr Gln Lys Ser
            595                 600                 605

Leu Ser Leu Ser Pro Gly Lys His His His His His
            610                 615                 620

<210> SEQ ID NO 114
<211> LENGTH: 334
<212> TYPE: PRT
<213> ORGANISM: Artificial Sequence
<220> FEATURE:
<223> OTHER INFORMATION: TPP-3188; murine Alk1-Fc antigen

<400> SEQUENCE: 114

Asp Leu Ala Lys Pro Ser Lys Leu Val Asn Cys Thr Cys Glu Ser Pro
1               5                   10                  15

His Cys Lys Arg Pro Phe Cys Gln Gly Ser Trp Cys Thr Val Val Leu
            20                  25                  30

Val Arg Glu Gln Gly Arg His Pro Gln Val Tyr Arg Gly Cys Gly Ser
        35                  40                  45

Leu Asn Gln Glu Leu Cys Leu Gly Arg Pro Thr Glu Phe Leu Asn His
    50                  55                  60

His Cys Cys Tyr Arg Ser Phe Cys Asn His Asn Val Ser Leu Met Leu
65                  70                  75                  80

Glu Ala Thr Gln Thr Pro Ser Glu Glu Pro Glu Val Asp Ala His Leu
                85                  90                  95

Pro Ile Glu Gly Arg Met Asp Pro Lys Ser Cys Asp Lys Thr His Thr
            100                 105                 110

Cys Pro Pro Cys Pro Ala Pro Glu Leu Leu Gly Gly Pro Ser Val Phe
        115                 120                 125

Leu Phe Pro Pro Lys Pro Lys Asp Thr Leu Met Ile Ser Arg Thr Pro
    130                 135                 140

Glu Val Thr Cys Val Val Val Asp Val Ser His Glu Asp Pro Glu Val
145                 150                 155                 160

Lys Phe Asn Trp Tyr Val Asp Gly Val Glu Val His Asn Ala Lys Thr
                165                 170                 175
```

```
Lys Pro Arg Glu Glu Gln Tyr Asn Ser Thr Tyr Arg Val Val Ser Val
                180                 185                 190

Leu Thr Val Leu His Gln Asp Trp Leu Asn Gly Lys Glu Tyr Lys Cys
            195                 200                 205

Lys Val Ser Asn Lys Ala Leu Pro Ala Pro Ile Glu Lys Thr Ile Ser
        210                 215                 220

Lys Ala Lys Gly Gln Pro Arg Glu Pro Gln Val Tyr Thr Leu Pro Pro
225                 230                 235                 240

Ser Arg Asp Glu Leu Thr Lys Asn Gln Val Ser Leu Thr Cys Leu Val
                245                 250                 255

Lys Gly Phe Tyr Pro Ser Asp Ile Ala Val Glu Trp Glu Ser Asn Gly
            260                 265                 270

Gln Pro Glu Asn Asn Tyr Lys Thr Thr Pro Pro Val Leu Asp Ser Asp
        275                 280                 285

Gly Ser Phe Phe Leu Tyr Ser Lys Leu Thr Val Asp Lys Ser Arg Trp
    290                 295                 300

Gln Gln Gly Asn Val Phe Ser Cys Ser Val Met His Glu Ala Leu His
305                 310                 315                 320

Asn His Tyr Thr Gln Lys Ser Leu Ser Leu Ser Pro Gly Lys
                325                 330

<210> SEQ ID NO 115
<211> LENGTH: 370
<212> TYPE: PRT
<213> ORGANISM: Artificial Sequence
<220> FEATURE:
<223> OTHER INFORMATION: TPP-11725; BMPR2-FcHis6 antigen

<400> SEQUENCE: 115

Met Ala Ser Gln Asn Gln Glu Arg Leu Cys Ala Phe Lys Asp Pro Tyr
1               5                   10                  15

Gln Gln Asp Leu Gly Ile Gly Glu Ser Arg Ile Ser His Glu Asn Gly
            20                  25                  30

Thr Ile Leu Cys Ser Lys Gly Ser Thr Cys Tyr Gly Leu Trp Glu Lys
        35                  40                  45

Ser Lys Gly Asp Ile Asn Leu Val Lys Gln Gly Cys Trp Ser His Ile
    50                  55                  60

Gly Asp Pro Gln Glu Cys His Tyr Glu Glu Cys Val Val Thr Thr Thr
65                  70                  75                  80

Pro Pro Ser Ile Gln Asn Gly Thr Tyr Arg Phe Cys Cys Cys Ser Thr
                85                  90                  95

Asp Leu Cys Asn Val Asn Phe Thr Glu Asn Phe Pro Pro Pro Asp Thr
            100                 105                 110

Thr Pro Leu Ser Pro Pro His Ser Phe Asn Arg Asp Glu Thr Ile Ile
        115                 120                 125

Glu Gly Arg Met Asp Pro Lys Ser Cys Asp Lys Thr His Thr Cys Pro
    130                 135                 140

Pro Cys Pro Ala Pro Glu Leu Leu Gly Gly Pro Ser Val Phe Leu Phe
145                 150                 155                 160

Pro Pro Lys Pro Lys Asp Thr Leu Met Ile Ser Arg Thr Pro Glu Val
                165                 170                 175

Thr Cys Val Val Val Asp Val Ser His Glu Asp Pro Glu Val Lys Phe
            180                 185                 190

Asn Trp Tyr Val Asp Gly Val Glu Val His Asn Ala Lys Thr Lys Pro
        195                 200                 205
```

```
Arg Glu Glu Gln Tyr Asn Ser Thr Tyr Arg Val Val Ser Val Leu Thr
    210                 215                 220

Val Leu His Gln Asp Trp Leu Asn Gly Lys Glu Tyr Lys Cys Lys Val
225                 230                 235                 240

Ser Asn Lys Ala Leu Pro Ala Pro Ile Glu Lys Thr Ile Ser Lys Ala
                245                 250                 255

Lys Gly Gln Pro Arg Glu Pro Gln Val Tyr Thr Leu Pro Pro Ser Arg
                260                 265                 270

Asp Glu Leu Thr Lys Asn Gln Val Ser Leu Thr Cys Leu Val Lys Gly
            275                 280                 285

Phe Tyr Pro Ser Asp Ile Ala Val Glu Trp Ser Asn Gly Gln Pro
    290                 295                 300

Glu Asn Asn Tyr Lys Thr Thr Pro Pro Val Leu Asp Ser Asp Gly Ser
305                 310                 315                 320

Phe Phe Leu Tyr Ser Lys Leu Thr Val Asp Lys Ser Arg Trp Gln Gln
                325                 330                 335

Gly Asn Val Phe Ser Cys Ser Val Met His Glu Ala Leu His Asn His
                340                 345                 350

Tyr Thr Gln Lys Ser Leu Ser Leu Ser Pro Gly Lys His His His His
            355                 360                 365

His His
    370

<210> SEQ ID NO 116
<211> LENGTH: 334
<212> TYPE: PRT
<213> ORGANISM: Artificial Sequence
<220> FEATURE:
<223> OTHER INFORMATION: TPP-11726; human Alk1-Fc antigen

<400> SEQUENCE: 116

Asp Pro Val Lys Pro Ser Arg Gly Pro Leu Val Thr Cys Thr Cys Glu
1               5                   10                  15

Ser Pro His Cys Lys Gly Pro Thr Cys Arg Gly Ala Trp Cys Thr Val
                20                  25                  30

Val Leu Val Arg Glu Glu Gly Arg His Pro Gln Glu His Arg Gly Cys
            35                  40                  45

Gly Asn Leu His Arg Glu Leu Cys Arg Gly Arg Pro Thr Glu Phe Val
        50                  55                  60

Asn His Tyr Cys Cys Asp Ser His Leu Cys Asn His Asn Val Ser Leu
65                  70                  75                  80

Val Leu Glu Ala Thr Gln Pro Pro Ser Glu Gln Pro Gly Thr Asp Gly
                85                  90                  95

Gln Ile Glu Gly Arg Ile Asp Pro Lys Ser Cys Asp Lys Thr His Thr
            100                 105                 110

Cys Pro Pro Cys Pro Ala Pro Glu Leu Leu Gly Gly Pro Ser Val Phe
        115                 120                 125

Leu Phe Pro Pro Lys Pro Lys Asp Thr Leu Met Ile Ser Arg Thr Pro
    130                 135                 140

Glu Val Thr Cys Val Val Val Asp Val Ser His Glu Asp Pro Glu Val
145                 150                 155                 160

Lys Phe Asn Trp Tyr Val Asp Gly Val Glu Val His Asn Ala Lys Thr
                165                 170                 175

Lys Pro Arg Glu Glu Gln Tyr Asn Ser Thr Tyr Arg Val Val Ser Val
            180                 185                 190
```

```
Leu Thr Val Leu His Gln Asp Trp Leu Asn Gly Lys Glu Tyr Lys Cys
            195                 200                 205

Lys Val Ser Asn Lys Ala Leu Pro Ala Pro Ile Glu Lys Thr Ile Ser
        210                 215                 220

Lys Ala Lys Gly Gln Pro Arg Glu Pro Gln Val Tyr Thr Leu Pro Pro
225                 230                 235                 240

Ser Arg Asp Glu Leu Thr Lys Asn Gln Val Ser Leu Thr Cys Leu Val
                245                 250                 255

Lys Gly Phe Tyr Pro Ser Asp Ile Ala Val Glu Trp Glu Ser Asn Gly
            260                 265                 270

Gln Pro Glu Asn Asn Tyr Lys Thr Thr Pro Pro Val Leu Asp Ser Asp
        275                 280                 285

Gly Ser Phe Phe Leu Tyr Ser Lys Leu Thr Val Asp Lys Ser Arg Trp
    290                 295                 300

Gln Gln Gly Asn Val Phe Ser Cys Ser Val Met His Glu Ala Leu His
305                 310                 315                 320

Asn His Tyr Thr Gln Lys Ser Leu Ser Leu Ser Pro Gly Lys
                325                 330

<210> SEQ ID NO 117
<211> LENGTH: 339
<212> TYPE: PRT
<213> ORGANISM: Artificial Sequence
<220> FEATURE:
<223> OTHER INFORMATION: TPP-17233; rhActivin RIA/ALK-2 Fc Chimera
      antigen

<400> SEQUENCE: 117

Asp Glu Lys Pro Lys Val Asn Pro Lys Leu Tyr Met Cys Val Cys Glu
1               5                   10                  15

Gly Leu Ser Cys Gly Asn Glu Asp His Cys Glu Gly Gln Gln Cys Phe
            20                  25                  30

Ser Ser Leu Ser Ile Asn Asp Gly Phe His Val Tyr Gln Lys Gly Cys
        35                  40                  45

Phe Gln Val Tyr Glu Gln Gly Lys Met Thr Cys Lys Thr Pro Pro Ser
    50                  55                  60

Pro Gly Gln Ala Val Glu Cys Cys Gln Gly Asp Trp Cys Asn Arg Asn
65                  70                  75                  80

Ile Thr Ala Gln Leu Pro Thr Lys Gly Lys Ser Phe Pro Gly Thr Gln
                85                  90                  95

Asn Phe His Leu Glu Val Gly Leu Ile Ile Leu Ser Val Val Phe Ala
            100                 105                 110

Val Cys Leu Leu Ala Cys Leu Leu Gly Val Ala Leu Arg Lys Phe Lys
        115                 120                 125

Arg Arg Asn Gln Glu Arg Leu Asn Pro Arg Asp Val Glu Tyr Gly Thr
130                 135                 140

Ile Glu Gly Leu Ile Thr Thr Asn Val Gly Asp Ser Thr Leu Ala Asp
145                 150                 155                 160

Leu Leu Asp His Ser Cys Thr Ser Gly Ser Gly Ser Gly Leu Pro Phe
                165                 170                 175

Leu Val Gln Arg Thr Val Ala Arg Gln Ile Thr Leu Leu Glu Cys Val
            180                 185                 190

Gly Lys Gly Arg Tyr Gly Glu Val Trp Arg Gly Ser Trp Gln Gly Glu
        195                 200                 205

Asn Val Ala Val Lys Ile Phe Ser Ser Arg Asp Glu Lys Ser Trp Phe
```

-continued

```
                         210                 215                 220
Arg Glu Thr Glu Leu Tyr Asn Thr Val Met Leu Arg His Glu Asn Ile
225                     230                 235                 240

Leu Gly Phe Ile Ala Ser Asp Met Thr Ser Arg His Ser Ser Thr Gln
                245                 250                 255

Leu Trp Leu Ile Thr His Tyr His Glu Met Gly Ser Leu Tyr Asp Tyr
                260                 265                 270

Leu Gln Leu Thr Thr Leu Asp Thr Val Ser Cys Leu Arg Ile Val Leu
            275                 280                 285

Ser Ile Ala Ser Gly Leu Ala His Leu His Ile Glu Ile Phe Gly Thr
            290                 295                 300

Gln Gly Lys Pro Ala Ile Ala His Arg Asp Leu Lys Ser Lys Asn Ile
305                 310                 315                 320

Leu Val Lys Lys Asn Gly Gln Cys Cys Ile Ala Asp Leu His His His
                325                 330                 335

His His His
```

BISPECIFIC ANTIBODIES BINDING ALK-1 AND BMPR-2

FIELD OF THE DISCLOSURE

The present invention relates to bispecific antibodies binding human ALK-1 and human BMPR-2. Also provided are BsABs which are agonists of ALK-1/BMPR-2 signaling, and BsABs which do not trigger osteogenic signaling. Furthermore, the invention relates to pharmaceutical uses of the BsABs, in particular for the treatment of pulmonary hypertension. Also provided are methods to screen for BsABs for use in the therapy, e.g. of pulmonary hypertension.

BACKGROUND

Vascular disease is triggered by endothelial cell dysfunction. Due to various factors, the endothelial cells start secretion of cytokines and chemokines and express adhesion molecules on their surface. Thereby, white blood cells (monocytes, granulocytes and lymphocytes) are recruited, which can infiltrate the blood vessel wall.

Cytokine stimulation of the smooth muscle cell layer and recruitment of white blood cells cause smooth muscle cells to proliferate and migrate towards the lumen of the blood vessel, resulting in thickening of the vessel wall and plaque formation.

Plaque results in obstructed blood flow leading to diminished amounts of oxygen and nutrients in the target organ. Finally, upon rupture, the plaque may also result in clot formation and stroke.

Pulmonary hypertension (PH) and its subcategory Pulmonary arterial hypertension (PAH) are life-threatening diseases affecting the blood vessels of the lungs.

PH is a haemodynamic abnormality of diverse aetiology and pathogenesis that challenges physicians with both its diagnosis and treatment. PH is clinically defined by a resting mean pulmonary arterial pressure ≥25 mmHg measured by right heart catheterization. The prognosis is poor, without specific treatment 1-, 3- and 5-year survivals are 68, 48 and 34%, respectively.

PH is characterized by the constriction of precapillary pulmonary arteries, associated with irreversible remodeling. The resulting increase in the pulmonary arterial pressure leads to right ventricular hypertrophy and eventually death from right heart failure.

Excess proliferation of pulmonary arterial endothelial and smooth muscle cells (SMC) is one result of pulmonary artery endothelial cell dysfunction in pulmonary arterial hypertension (PAH). As a result of the constriction of precapillary pulmonary arteries, precapillary pulmonary hypertension occurs, with elevated pulmonary vascular resistance, i.e., a mean pulmonary artery pressure of ≥25 mm Hg. In addition, PAH is defined by a normal pulmonary arterial wedge pressure ≤15 mm Hg and pulmonary vascular resistance of >240 dyn$\times$s$\times$cm$^{-5}$. Initially PAH was thought to be a disease that mostly affected young women. However, the mean age of patients diagnosed with PAH in Germany has steadily increased; presently the mean age is 65 years (Hoeper, MM, et al. Dtsch Arztebl Int (2017) 114: 73-84). In PAH, remodeling of pulmonary arteries leads to increased vascular resistance and an increase of pulmonary blood pressure. The increase in the pulmonary arterial pressure leads to right ventricular hypertrophy and eventually death from right heart failure.

Symptoms of PAH include shortness of breath, syncope, fatigue, chest pain, swelling of the legs, and fast heartbeat.

Treatment depends on the type, i.e., if the PH is arterial, venous, hypoxic, thromboembolic, or miscellaneous. Most treatments aim at optimizing left ventricular function by the application of diuretics, digoxins, blood thinners, or by repair/replacement of mitral valve or aortic valve. Various therapeutic approaches rely on a decreasing blood pressure by relaxation of the pulmonary arteries (Ca antagonists, ET antagonists, PDE V inhibitors, sGC stimulators, etc.). Most available treatments thus target the symptoms while the overall prognosis remains poor.

In consequence, there is a long felt need to provide an anti-remodeling drug. Furthermore, a hemodynamically neutral anti-remodeling drug might be applicable in combination with therapy approaches based on lowering the blood pressure.

Based on genetic studies it has been suggested that compromised bone morphogenetic protein (BMP) receptor type II (BMPR-2) signaling in endothelial cells plays an important role in the pathobiology of PAH. Other PAH mutations in the BMP pathway have likewise been described. While BMPR-2 mutations are found in 70% of heritable PAH and 10-40% of idiopathic PAH (Ma & Chung, 2014, Human Genetics), more than 300 loss-of-function mutations of BMPR-2 have been identified in PAH patients. Other mutations in the BMP pathway include alterations in ALK-1, SMAD9, and ENG. Recently, a novel BMP-9 mutation was identified in a pediatric PAH patient (Wang et al. 2016, BMC Pulmonary Medicine).

In several animal models, e.g., in a genetic BMPR-2 mutated mouse model as well as in Sugen/Hypoxia rat models, BMP-9 has been shown to revert PAH (Long et al Nat Med. 2015 July; 21(7):777-85). For instance, right ventricular systolic blood pressure (RVSP) and vessel muscularization were elevated in the genetic mouse model and were found to be reversed by daily i.p. injection of 75 ng BMP-9 for four weeks. BMP-9 has furthermore been described to prevent endothelial cell apoptosis and decrease endothelial permeability (Long et al Nat Med. 2015 July; 21(7):777-85). Administration of exogenous BMP-9 has been shown to augment endothelial BMPR-2 signaling and reverse PAH in several rodent models of disease.

The BMPR-2/ALK-1 signaling complex with its preferred ligand BMP-9 was therefore hypothesized to be a potential therapeutic target for building a remodeling drug. One option to restore or increase signaling of the BMPR-2/ALK-1 heterotetrameric complex is the application of recombinant BMP-9 or recombinant designer BMP-9s.

BMP-9 (also GDF-2, growth differentiation factor 2) belongs to the TGF-beta family. The TGF-beta superfamily comprises three different subfamilies: activins, TGF-betas and bone morphogenetic/growth differentiation factor proteins (BMP/GDF). In addition to BMP-9 (GDF2), further members of the BMPs include for example BMP-2, BMP-3 (osteogenin), BMP-3b (GDF-10), BMP-4 (BMP-2b), BMP-5, BMP-6, BMP-7, BMP-8, BMP-8b, BMP-10, BMP-11 (GDF11), BMP-12, BMP-13, BMP-14 and BMP-15.

Alternative names for BMPs comprise osteogenic proteins (OPs), growth differentiation factors (GDFs) or cartilage-derived morphogenetic proteins (CDMPs). Originally identified due to their involvement in the formation of bone and cartilage tissue, BMPs were found to control various cellular and developmental processes (Varga et al, 2005; Oncogene 24:5713-5721, Miyazono et al 2010, J Biochem. 147:35-51). Among these processes are embryonic pattern formation and tissue specification, wound healing and tissue repair processes. The members of this family are regulators of cell growth and differentiation in both embryonic and adult tissues. Rodent studies suggest a role of BMP-9 in the adult liver and in differentiation of cholinergic central nervous system neurons.

The first step of BMP signal transduction is the binding of a BMP dimer to two type I and two type II serine/threonine kinase receptors. Type II receptors bind ligands in the absence of type I receptors, but require their respective type I receptors for signaling. In contrast, type I receptors require their respective type II receptors for binding of the ligand. Type I receptors comprise ALK-1, ALK-2 (ACVR1A), ALK-3 (BMPR1A), and ALK-6 (BMPR1B). Type II receptors comprise ActR11a, ActR11b, and BMPR-2 (BMPR-II). After binding of BMP, a phosphorylation cascade is started, wherein type II receptors phosphorylate type I receptors and the type I receptors subsequently phosphorylate SMAD family members. SMADs are a family of transcription factors and-upon activation-translocate to the nucleus, where they control the expression of their respective target genes. BMP-9 has been described to trigger the phosphorylation of SMAD1 and SMAD5.

BMPs are furthermore characterized by a polybasic proteolytic processing site which is cleaved to release a mature protein comprising seven conserved cysteine residues. BMP-9 is synthesized with a signal peptide and a pro-domain. Upon homo-dimerization, BMP-9 is cleaved by a convertase into its active form. In contrast to other BMPs, the pro-region can remain tightly associated with the mature protein, without affecting the activity. With its nearest neighbor BMP-10, BMP-9 shares 60% identity at the amino acid level. BMP-9 and 10 both represent ligands circulating in the blood that selectively bind and activate BMPR-2 receptor complexes on endothelial cells.

BMPR-2 and ALK-1 are primarily expressed on endothelial cells and form the receptor complex for their ligand BMP-9. BMPR-2 mutations or BMPR-2 silencing have been found to increase endothelial permeability in vitro and in vivo (Burton et al. 2010, Vasc. Biol.). Likewise, TNFα-induced apoptosis and LPS-induced permeability are increased in BMPR-2-mutated blood outgrowth endothelial cells (BOECs), but can be attenuated by BMP-9 treatment (Long et al Nat Med. 2015 July; 21(7):777-85).

Unmodified and modified variants of the natural ligand BMP-9 have been described in order to activate the ALK-1/BMPR-2 complex (WO 2016/005756 and Long et al. 2015 doi:10.1038/nm.3877). However, the application of BMP-9 or variants thereof (see for instance WO2016/005756) has several drawbacks. The shortcomings of a BMP-9 replacement therapy in a therapeutic setting comprise i) the short half-life, ii) the severe risk of immunogenicity, iii) the low yields and challenges in the development, and iv) potential side effects through osteogenic activity.

Bone morphogenic proteins (BMPs) are known to promote osteogenic activity including osteogenesis, osteocalcin induction and matrix mineralization. Natural BMP-9 and most synthetic variants of BMP-9 can initiate osteogenic signaling and bone formation upon administration in vivo. Without being bound by theory, BMP-9 signaling via ALK-2 has been hypothesized to be involved in this osteogenic activity. Alignment of the sequences for ALK-1 and ALK-2 using the BLAST algorithm results in <60% sequence identity.

SUMMARY

According to a first aspect, the current invention provides a bispecific antibody (BsAB), wherein said antibody comprises two binding domains, wherein the first binding domain is specific for human ALK-1 and the second binding domain is specific for human BMPR-2.

BsABs according to the current invention are usually characterized by a longer half-life than the natural ligand of the ALK-1/BMPR-2 complex, BMP-9, or its variants. Furthermore, BsABs according to the current invention can be produced with high yields. Affinities are better accessible than for BMP-9 and its variants, because the BsABs or their binding domains can be easily maturated, or screening approaches can be used to detect binders with optimized binding capabilities. For BsABs, each binding site can be optimized individually. Finally, even in the absence of functional BMP-9 signaling, e.g. due to a genetic defect, an antibody approach could still be able to rescue the ALK-1/BMPR-2 signaling cascade.

In a preferred embodiment according to the first aspect, the ALK-1 is human ALK-1 or a fragment thereof, and/or the BMPR-2 is human BMPR-2 or a fragment thereof. In some preferred embodiment according to the first aspect, the bispecific antibody or at least one portion thereof, is monoclonal. In particular embodiments, the antibody, or at least one portion thereof, is chimeric, or humanized, or fully human.

According to a second aspect, the current invention comprises a bispecific antibody which has agonistic activity for ALK-1/BMPR-2 signaling in a target cell, such as an endothelial cell.

BsAB with agonistic activity for ALK-1/BMPR-2 signaling have a higher probability to revert vessel muscularization and restore barrier function in lung endothelial cells by decreasing the endothelial permeability.

In a preferred embodiment according to the second aspect, the BsAB promotes dimerization of ALK-1 and BMPR-2 and this can be shown for example in the PathHunter Dimerization assay using the U2OS ACVRL1/BMPR-2 Dimerization Cell Line.

In another preferred embodiment for a BsAB which is agonistic for ALK-1/BMPR-2 signaling, the EC50 of the bispecific antibody according to the current invention is higher than or equal to the EC50 of BMP-9.

In a preferred embodiment according to the second aspect, an effective dose of the BsAB promotes phosphorylation of SMAD1 and/or SMAD5.

In a preferred embodiment according to the second aspect, an effective dose of said antibody reduces the apoptotic index of endothelial cells.

According to a third aspect of the current invention, the antibody according to the first aspect or the antibody according to the second aspect has a lower osteogenic activity than rhBMP-9.

BsABs with lower osteogenic activity than rhBMP-9 have a lower risk to induce bone formation as a side effect.

In a particularly preferred embodiment, there is provided a BsAB according to any of the aforementioned aspects, wherein said BsAB has agonistic activity with respect to ALK-1/BMPR-2 signaling, and wherein an EC50 of said BsAB has a lower osteogenic activity than an EC50 of rhBMP-9, or has no osteogenic activity.

In a particularly preferred embodiment, there is provided a BsAB, wherein said BsAB comprises two binding domains, wherein the first binding domain is specific for ALK-1 and the second binding domain is specific for BMPR-2, and wherein said BsAB has agonistic activity with respect to ALK-1/BMPR-2 signaling, and wherein an EC50 of said BsAB has a lower osteogenic activity than an EC50 of rhBMP-9, or has no osteogenic activity.

BsAB with agonistic activity for ALK-1/BMPR-2 signaling but with lower osteogenic activity than rhBMP-9 and/or without osteogenic activity are likely to revert endothelial dysfunction, decrease right ventricular systolic blood pressure (RVSP), and/or revert PAH.

Bone morphogenic proteins (BMPs) are known to promote osteogenesis. Whereas human BMP-9, BMP-9 variants and designer BMP-9s, such as mutated BMP-9 versions are likely to induce osteogenic activities via ALK-2 signaling, this is different for BsABs targeting only and specifically the ALK-1/BMPR-2 receptor complex. Due to their genuine specificity for ALK-1 (and BMPR-2), induction of signaling via ALK-2 is unlikely for antibodies according to the current invention, and can furthermore be easily excluded by specific assays.

In a preferred embodiment according to the third aspect, the BsAB according to the second aspect is characterized in that C2C12 cells treated with the EC50 of rhBMP-9 have a higher alkaline phosphatase (ALP) activity than C2C12 cells treated with the same concentration of the BsAB or treated with the EC50 of the BsAB.

The invention further provides BsABs for use as a medicament as well as BsABs for use in the treatment of vascular disease or pulmonary hypertension. In some embodiments the use in the treatment of vascular disease or pulmonary hypertension comprises increasing or rescuing the ALK-1/BMPR-2 signaling in at least one target cell of a subject. In some embodiments, the at least one target cell is an endothelial cell, such as a lung endothelial cell. In some embodiments, the subject is a human or a mammal. In some embodiments, the PH is a PAH.

Further provided are pharmaceutical compositions comprising both, a BsAB as described herein, and a pharmaceutically acceptable vehicle.

Also provided are methods to screen for BsABs with a profile that resembles BMP-9 with respect to ALK-1/BMPR-2 signaling, but differ from BMP-9 with respect to the induction of bone formation. In particular, there is provided a method to test the suitability of a BsAB for use in the therapy, e.g. of pulmonary hypertension, comprising the steps of (i) evaluating the agonistic activity of the BsAB for ALK-1/BMPR-2 signaling, and optionally (ii) evaluating the osteogenic activity of the BsAB.

BRIEF DESCRIPTION OF THE SEQUENCE IDS

Figure 1:
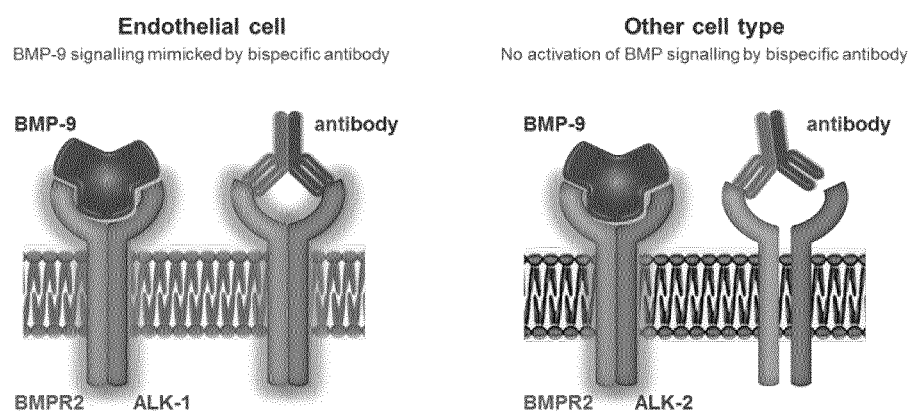
FIG. 1 is a schematic representation of an antibody selectively activating endothelial ALK-1/BMPR-2 in an endothelial cell. In other cell types expressing ALK-2/BMPR-2, ALK-2 signaling is not activated.

| Seq ID | Construct | Antibody ID | Construct Sequence Name | Sequence Region | VH/VL or CDR | Type |
|---|---|---|---|---|---|---|
| 1 | BsAB | TPP-14696 | 13654-13667-scFv-kih-IgG2__Fc | Chain1 | | PRT |
| 2 | BsAB | TPP-14696 | 13654-13667-scFv-kih-IgG2__Fc | Chain1 | HCDR1 | PRT |
| 3 | BsAB | TPP-14696 | 13654-13667-scFv-kih-IgG2__Fc | Chain1 | HCDR2 | PRT |
| 4 | BsAB | TPP-14696 | 13654-13667-scFv-kih-IgG2__Fc | Chain1 | HCDR3 | PRT |
| 5 | BsAB | TPP-14696 | 13654-13667-scFv-kih-IgG2__Fc | Chain1 | LCDR1 | PRT |
| 6 | BsAB | TPP-14696 | 13654-13667-scFv-kih-IgG2__Fc | Chain1 | LCDR2 | PRT |

-continued

| Seq ID | Construct | Antibody ID | Construct Sequence Name | Sequence Region | VH/VL or CDR | Type |
|---|---|---|---|---|---|---|
| 7 | BsAB | TPP-14696 | 13654-13667-scFv-kih-IgG2_Fc | Chain1 | LCDR3 | PRT |
| 8 | BsAB | TPP-14696 | 13654-13667-scFv-kih-IgG2_Fc | Chain2 | | PRT |
| 9 | BsAB | TPP-14696 | 13654-13667-scFv-kih-IgG2_Fc | Chain2 | HCDR1 | PRT |
| 10 | BsAB | TPP-14696 | 13654-13667-scFv-kih-IgG2_Fc | Chain2 | HCDR2 | PRT |
| 11 | BsAB | TPP-14696 | 13654-13667-scFv-kih-IgG2_Fc | Chain2 | HCDR3 | PRT |
| 12 | BsAB | TPP-14696 | 13654-13667-scFv-kih-IgG2_Fc | Chain2 | LCDR1 | PRT |
| 13 | BsAB | TPP-14696 | 13654-13667-scFv-kih-IgG2_Fc | Chain2 | LCDR2 | PRT |
| 14 | BsAB | TPP-14696 | 13654-13667-scFv-kih-IgG2_Fc | Chain2 | LCDR3 | PRT |
| 15 | BsAB | TPP-14696 | 13654-13667-scFv-kih-IgG2_Fc | Chain1 | | DNA |
| 16 | BsAB | TPP-14696 | 13654-13667-scFv-kih-IgG2_Fc | Chain1 | HCDR1 | DNA |
| 17 | BsAB | TPP-14696 | 13654-13667-scFv-kih-IgG2_Fc | Chain1 | HCDR2 | DNA |
| 18 | BsAB | TPP-14696 | 13654-13667-scFv-kih-IgG2_Fc | Chain1 | HCDR3 | DNA |
| 19 | BsAB | TPP-14696 | 13654-13667-scFv-kih-IgG2_Fc | Chain1 | LCDR1 | DNA |
| 20 | BsAB | TPP-14696 | 13654-13667-scFv-kih-IgG2_Fc | Chain1 | LCDR2 | DNA |
| 21 | BsAB | TPP-14696 | 13654-13667-scFv-kih-IgG2_Fc | Chain1 | LCDR3 | DNA |
| 22 | BsAB | TPP-14696 | 13654-13667-scFv-kih-IgG2_Fc | Chain2 | | DNA |
| 23 | BsAB | TPP-14696 | 13654-13667-scFv-kih-IgG2_Fc | Chain2 | HCDR1 | DNA |
| 24 | BsAB | TPP-14696 | 13654-13667-scFv-kih-IgG2_Fc | Chain2 | HCDR2 | DNA |
| 25 | BsAB | TPP-14696 | 13654-13667-scFv-kih-IgG2_Fc | Chain2 | HCDR3 | DNA |
| 26 | BsAB | TPP-14696 | 13654-13667-scFv-kih-IgG2_Fc | Chain2 | LCDR1 | DNA |
| 27 | BsAB | TPP-14696 | 13654-13667-scFv-kih-IgG2_Fc | Chain2 | LCDR2 | DNA |
| 28 | BsAB | TPP-14696 | 13654-13667-scFv-kih-IgG2_Fc | Chain2 | LCDR3 | DNA |
| 29 | BsAB | TPP-14719 | 13660-13469-scFv-kih-IgG2_Fc | Chain1 | | PRT |
| 30 | BsAB | TPP-14719 | 13660-13469-scFv-kih-IgG2_Fc | Chain1 | HCDR1 | PRT |
| 31 | BsAB | TPP-14719 | 13660-13469-scFv-kih-IgG2_Fc | Chain1 | HCDR2 | PRT |
| 32 | BsAB | TPP-14719 | 13660-13469-scFv-kih-IgG2_Fc | Chain1 | HCDR3 | PRT |
| 33 | BsAB | TPP-14719 | 13660-13469-scFv-kih-IgG2_Fc | Chain1 | LCDR1 | PRT |
| 34 | BsAB | TPP-14719 | 13660-13469-scFv-kih-IgG2_Fc | Chain1 | LCDR2 | PRT |
| 35 | BsAB | TPP-14719 | 13660-13469-scFv-kih-IgG2_Fc | Chain1 | LCDR3 | PRT |
| 36 | BsAB | TPP-14719 | 13660-13469-scFv-kih-IgG2_Fc | Chain2 | | PRT |
| 37 | BsAB | TPP-14719 | 13660-13469-scFv-kih-IgG2_Fc | Chain2 | HCDR1 | PRT |
| 38 | BsAB | TPP-14719 | 13660-13469-scFv-kih-IgG2_Fc | Chain2 | HCDR2 | PRT |
| 39 | BsAB | TPP-14719 | 13660-13469-scFv-kih-IgG2_Fc | Chain2 | HCDR3 | PRT |
| 40 | BsAB | TPP-14719 | 13660-13469-scFv-kih-IgG2_Fc | Chain2 | LCDR1 | PRT |
| 41 | BsAB | TPP-14719 | 13660-13469-scFv-kih-IgG2_Fc | Chain2 | LCDR2 | PRT |
| 42 | BsAB | TPP-14719 | 13660-13469-scFv-kih-IgG2_Fc | Chain2 | LCDR3 | PRT |
| 43 | BsAB | TPP-14719 | 13660-13469-scFv-kih-IgG2_Fc | Chain1 | | DNA |
| 44 | BsAB | TPP-14719 | 13660-13469-scFv-kih-IgG2_Fc | Chain1 | HCDR1 | DNA |
| 45 | BsAB | TPP-14719 | 13660-13469-scFv-kih-IgG2_Fc | Chain1 | HCDR2 | DNA |
| 46 | BsAB | TPP-14719 | 13660-13469-scFv-kih-IgG2_Fc | Chain1 | HCDR3 | DNA |
| 47 | BsAB | TPP-14719 | 13660-13469-scFv-kih-IgG2_Fc | Chain1 | LCDR1 | DNA |
| 48 | BsAB | TPP-14719 | 13660-13469-scFv-kih-IgG2_Fc | Chain1 | LCDR2 | DNA |
| 49 | BsAB | TPP-14719 | 13660-13469-scFv-kih-IgG2_Fc | Chain1 | LCDR3 | DNA |
| 50 | BsAB | TPP-14719 | 13660-13469-scFv-kih-IgG2_Fc | Chain2 | | DNA |
| 51 | BsAB | TPP-14719 | 13660-13469-scFv-kih-IgG2_Fc | Chain2 | HCDR1 | DNA |
| 52 | BsAB | TPP-14719 | 13660-13469-scFv-kih-IgG2_Fc | Chain2 | HCDR2 | DNA |
| 53 | BsAB | TPP-14719 | 13660-13469-scFv-kih-IgG2_Fc | Chain2 | HCDR3 | DNA |
| 54 | BsAB | TPP-14719 | 13660-13469-scFv-kih-IgG2_Fc | Chain2 | LCDR1 | DNA |
| 55 | BsAB | TPP-14719 | 13660-13469-scFv-kih-IgG2_Fc | Chain2 | LCDR2 | DNA |
| 56 | BsAB | TPP-14719 | 13660-13469-scFv-kih-IgG2_Fc | Chain2 | LCDR3 | DNA |
| 57 | MsAB | TPP-13469 | 484A-M010-C06-scFv-Fc-hIgG2 | | HCDR1 | PRT |
| 58 | MsAB | TPP-13469 | 484A-M010-C06-scFv-Fc-hIgG2 | | HCDR2 | PRT |
| 59 | MsAB | TPP-13469 | 484A-M010-C06-scFv-Fc-hIgG2 | | HCDR3 | PRT |
| 60 | MsAB | TPP-13469 | 484A-M010-C06-scFv-Fc-hIgG2 | | LCDR1 | PRT |
| 61 | MsAB | TPP-13469 | 484A-M010-C06-scFv-Fc-hIgG2 | | LCDR2 | PRT |
| 62 | MsAB | TPP-13469 | 484A-M010-C06-scFv-Fc-hIgG2 | | LCDR3 | PRT |
| 63 | MsAB | TPP-13469 | 484A-M010-C06-scFv-Fc-hIgG2 | | HCDR1 | DNA |
| 64 | MsAB | TPP-13469 | 484A-M010-C06-scFv-Fc-hIgG2 | | HCDR2 | DNA |
| 65 | MsAB | TPP-13469 | 484A-M010-C06-scFv-Fc-hIgG2 | | HCDR3 | DNA |
| 66 | MsAB | TPP-13469 | 484A-M010-C06-scFv-Fc-hIgG2 | | LCDR1 | DNA |
| 67 | MsAB | TPP-13469 | 484A-M010-C06-scFv-Fc-hIgG2 | | LCDR2 | DNA |
| 68 | MsAB | TPP-13469 | 484A-M010-C06-scFv-Fc-hIgG2 | | LCDR3 | DNA |
| 69 | MsAB | TPP-13469 | 484A-M010-C06-scFv-Fc-hIgG2 | | scFv | PRT |
| 70 | MsAB | TPP-13469 | 484A-M010-C06-scFv-Fc-hIgG2 | | scFv | DNA |
| 71 | MsAB | TPP-13654 | 484A-M233-M07-scFv-Fc-hIgG2 | | HCDR1 | PRT |
| 72 | MsAB | TPP-13654 | 484A-M233-M07-scFv-Fc-hIgG2 | | HCDR2 | PRT |
| 73 | MsAB | TPP-13654 | 484A-M233-M07-scFv-Fc-hIgG2 | | HCDR3 | PRT |
| 74 | MsAB | TPP-13654 | 484A-M233-M07-scFv-Fc-hIgG2 | | LCDR1 | PRT |
| 75 | MsAB | TPP-13654 | 484A-M233-M07-scFv-Fc-hIgG2 | | LCDR2 | PRT |
| 76 | MsAB | TPP-13654 | 484A-M233-M07-scFv-Fc-hIgG2 | | LCDR3 | PRT |
| 77 | MsAB | TPP-13654 | 484A-M233-M07-scFv-Fc-hIgG2 | | HCDR1 | DNA |
| 78 | MsAB | TPP-13654 | 484A-M233-M07-scFv-Fc-hIgG2 | | HCDR2 | DNA |
| 79 | MsAB | TPP-13654 | 484A-M233-M07-scFv-Fc-hIgG2 | | HCDR3 | DNA |
| 80 | MsAB | TPP-13654 | 484A-M233-M07-scFv-Fc-hIgG2 | | LCDR1 | DNA |
| 81 | MsAB | TPP-13654 | 484A-M233-M07-scFv-Fc-hIgG2 | | LCDR2 | DNA |
| 82 | MsAB | TPP-13654 | 484A-M233-M07-scFv-Fc-hIgG2 | | LCDR3 | DNA |

-continued

| Seq ID | Construct | Antibody ID | Construct Sequence Name | Sequence Region | VH/VL or CDR | Type |
|---|---|---|---|---|---|---|
| 83 | MsAB | TPP-13654 | 484A-M233-M07-scFv-Fc-hIgG2 | | scFv | PRT |
| 84 | MsAB | TPP-13654 | 484A-M233-M07-scFv-Fc-hIgG2 | | scFv | DNA |
| 85 | MsAB | TPP-13660 | 484A-M232-A14-scFv-Fc-hIgG2 | | HCDR1 | PRT |
| 86 | MsAB | TPP-13660 | 484A-M232-A14-scFv-Fc-hIgG2 | | HCDR2 | PRT |
| 87 | MsAB | TPP-13660 | 484A-M232-A14-scFv-Fc-hIgG2 | | HCDR3 | PRT |
| 88 | MsAB | TPP-13660 | 484A-M232-A14-scFv-Fc-hIgG2 | | LCDR1 | PRT |
| 89 | MsAB | TPP-13660 | 484A-M232-A14-scFv-Fc-hIgG2 | | LCDR2 | PRT |
| 90 | MsAB | TPP-13660 | 484A-M232-A14-scFv-Fc-hIgG2 | | LCDR3 | PRT |
| 91 | MsAB | TPP-13660 | 484A-M232-A14-scFv-Fc-hIgG2 | | HCDR1 | DNA |
| 92 | MsAB | TPP-13660 | 484A-M232-A14-scFv-Fc-hIgG2 | | HCDR2 | DNA |
| 93 | MsAB | TPP-13660 | 484A-M232-A14-scFv-Fc-hIgG2 | | HCDR3 | DNA |
| 94 | MsAB | TPP-13660 | 484A-M232-A14-scFv-Fc-hIgG2 | | LCDR1 | DNA |
| 95 | MsAB | TPP-13660 | 484A-M232-A14-scFv-Fc-hIgG2 | | LCDR2 | DNA |
| 96 | MsAB | TPP-13660 | 484A-M232-A14-scFv-Fc-hIgG2 | | LCDR3 | DNA |
| 97 | MsAB | TPP-13660 | 484A-M232-A14-scFv-Fc-hIgG2 | | scFv | PRT |
| 98 | MsAB | TPP-13660 | 484A-M232-A14-scFv-Fc-hIgG2 | | scFv | DNA |
| 99 | MsAB | TPP-13667 | 484A-M198-J22-scFv-Fc-hIgG2 | | HCDR1 | PRT |
| 100 | MsAB | TPP-13667 | 484A-M198-J22-scFv-Fc-hIgG3 | | HCDR2 | PRT |
| 101 | MsAB | TPP-13667 | 484A-M198-J22-scFv-Fc-hIgG4 | | HCDR3 | PRT |
| 102 | MsAB | TPP-13667 | 484A-M198-J22-scFv-Fc-hIgG5 | | LCDR1 | PRT |
| 103 | MsAB | TPP-13667 | 484A-M198-J22-scFv-Fc-hIgG6 | | LCDR2 | PRT |
| 104 | MsAB | TPP-13667 | 484A-M198-J22-scFv-Fc-hIgG7 | | LCDR3 | PRT |
| 105 | MsAB | TPP-13667 | 484A-M198-J22-scFv-Fc-hIgG8 | | HCDR1 | DNA |
| 106 | MsAB | TPP-13667 | 484A-M198-J22-scFv-Fc-hIgG9 | | HCDR2 | DNA |
| 107 | MsAB | TPP-13667 | 484A-M198-J22-scFv-Fc-hIgG10 | | HCDR3 | DNA |
| 108 | MsAB | TPP-13667 | 484A-M198-J22-scFv-Fc-hIgG11 | | LCDR1 | DNA |
| 109 | MsAB | TPP-13667 | 484A-M198-J22-scFv-Fc-hIgG12 | | LCDR2 | DNA |
| 110 | MsAB | TPP-13667 | 484A-M198-J22-scFv-Fc-hIgG13 | | LCDR3 | DNA |
| 111 | MsAB | TPP-13667 | 484A-M198-J22-scFv-Fc-hIgG14 | | scFv | PRT |
| 112 | MsAB | TPP-13667 | 484A-M198-J22-scFv-Fc-hIgG15 | | scFv | DNA |
| 113 | Antigen | TPP-3188 | hROR1-Fc | Chain1 | | PRT |
| 114 | Antigen | TPP-11724 | murine ALK-1-Fc | Chain1 | | PRT |
| 115 | Antigen | TPP-11725 | BMPR-2-FcHis6 | Chain1 | | PRT |
| 116 | Antigen | TPP-11726 | human ALK-1-Fc | Chain1 | | PRT |
| 117 | Antigen | TPP-17233 | hActivin RIA/ALK-2 Fc Chimera | Chain1 | | PRT |

DETAILED DESCRIPTION

Definitions

Unless otherwise defined, all other scientific and technical terms used in the description, figures and claims have their ordinary meaning as commonly understood by one of ordinary skill in the art. All publications, patent applications, patents, and other references mentioned herein are incorporated by reference in their entirety. In case of conflict, the present specification, including definitions, will prevail. If two or more documents incorporated by reference include conflicting and/or inconsistent disclosure with respect to each other, then the document having the later effective date shall control. The materials, methods, and examples are illustrative only and not intended to be limiting.

Unless otherwise stated, the following terms used in this document, including the description and claims, have the definitions given below.

The word "about" as used herein refers to a value being within an acceptable error range for the particular value as determined by one of ordinary skill in the art, which will depend in part on how the value is measured or determined, i.e., on the limitations of the measurement system. For example, "about" can mean within 1 or more than 1 standard deviation, per the practice in the art. The term "about" is also used to indicate that the amount or value in question may be the value designated or some other value that is approximately the same. The phrase is intended to convey that similar values promote equivalent results or effects as described herein. In this context "about" may refer to a range above and/or below of up to 10%. Wherever the term "about" is specified for a certain assay or embodiment, that definition prevails for the particular context.

The terms "comprising", "including", "containing", "having" etc. shall be read expansively or open-ended and without limitation. Singular forms such as "a", "an" or "the" include plural references unless the context clearly indicates otherwise. Thus, for example, reference to a "BsAB" includes a single BsAB as well as a plurality of BsAB, either the same or different. Likewise reference to "cell" includes a single cell as well as a plurality of cells.

Unless otherwise indicated, the term "at least" preceding a series of elements is to be understood to refer to every element in the series. The terms "at least one" and "at least one of" include for example, one, two, three, four, or five or more elements. It is furthermore understood that slight variations above and below a stated range can be used to achieve substantially the same results as a value within the range. Also, unless indicated otherwise, the disclosure of ranges is intended as a continuous range including every value between the minimum and maximum values.

The term "antibody" includes, but is not limited to, an immunoglobulin (e.g., IgG1, IgG2a, IgG2b, IgG3, IgG4, IgM, IgD, IgE, IgA) and an antigen binding fragment thereof, but it also includes any proteinaceous binding molecule with immunoglobulin-like function. An antibody fragment generally contains an antigen binding or variable region. Examples of (recombinant) antibody fragments are immunoglobulin fragments such as Fab fragments, Fab' fragments, Fv fragments, single-chain Fv fragments (scFv), diabodies or domain antibodies (Holt, L. J., et al., Trends Biotechnol. (2003), 21, 11, 484-490). An example of a proteinaceous binding molecule with immunoglobulin-like functions is a mutein based on a polypeptide of the lipocalin family (WO 03/029462, Beste et al., Proc. Natl. Acad. Sci. USA (1999) 96, 1898-1903). Lipocalins, such as the bilin binding protein, the human neutrophil gelatinase-associated lipocalin, human Apolipoprotein D or glycodelin, possess natural ligand-binding sites that can be modified so that they bind to selected small protein regions known as haptens. Examples of other proteinaceous binding molecules are the so-called glubodies (see e.g. international patent application WO 96/23879 or Napolitano, E. W., et al., Chemistry & Biology (1996) 3, 5, 359-367), proteins based on the ankyrin scaffold (Mosavi, L. K., et al., Protein Science (2004) 13, 6, 1435-1448) or crystalline scaffold (e.g. international patent application WO 01/04144), the proteins described in Skerra, J. Mol. Recognit. (2000) 13, 167-187, Adnectins, tetranectins and avimers. Avimers contain so called A-domains that occur as strings of multiple domains in several cell surface receptors (Silverman, J., et al., Nature Biotechnology (2005) 23, 1556-1561). Adnectins, derived from a domain of human fibronectin, contain three loops that can be engineered for immunoglobulin-like binding to targets (Gill, D. S. & Damle, N. K., Current Opinion in Biotechnology (2006) 17, 653-658). Tetranectins, derived from the respective human homotrimeric protein, likewise contain loop regions in a C-type lectin domain that can be engineered for desired binding (ibid.). Peptoids, which can act as protein ligands, are oligo(N-alkyl) glycines that differ from peptides in that the side chain is connected to the amide nitrogen rather than the alpha carbon atom. Peptoids are typically resistant to proteases and other modifying enzymes and can have a much higher cell permeability than peptides (see e.g. Kwon, Y.-U., and Kodadek, T., J. Am. Chem. Soc. (2007) 129, 1508-1509).

Antibodies or antibody fragments can be produced synthetically or recombinantly. A number of technologies are available to produce antibodies. For example, phage-antibody technology can be used to generate antibodies (Knappik et al., J. Mol. Biol. 296:57-86, 2000). Another approach for obtaining antibodies is to screen a DNA library from B cells as described in WO 91/17271 and WO 92/01047. In these methods, libraries of phage are produced in which members display different antibodies on their outer surfaces. Antibodies are usually displayed as Fv or Fab fragments. Phage displaying antibodies are selected by affinity enrichment for binding to a selected protein. Antibodies can also be produced using trioma methodology (e.g., Oestberg et al., Hybridoma 2:361-367, 1983; U.S. Pat. Nos. 4,634,664; 4,634,666).

Antibodies can also be purified from any cell that expresses the antibodies, including host cells that have been transfected with antibody-encoding expression constructs. The host cells can be cultured under conditions whereby the antibodies are expressed. Purified antibody can be separated from other cellular components that can associate with the antibody in the cell, such as certain proteins, carbohydrates, or lipids, using methods well known in the art. Such methods include, but are not limited to, size exclusion chromatography, ammonium sulfate fractionation, ion exchange chromatography, affinity chromatography, and preparative gel electrophoresis. Purity of the preparations can be assessed by any means known in the art, such as SDS-polyacrylamide gel electrophoresis. A preparation of purified antibodies can contain more than one type of antibody.

Alternatively, antibodies according to the current invention can be produced using chemical methods to synthesize its amino acid sequence, such as by direct peptide synthesis using solid-phase techniques (e.g., Merrifield, J. Am. Chem. Soc. 85:2149-2154, 1963; Roberge et al., Science 269:202-204, 1995). Protein synthesis can be performed using manual techniques or by automation. Optionally, fragments of antibodies can be separately synthesized and combined using chemical methods to produce a full-length molecule.

The term "Fc domain" or "Fc region" as used herein refers to a C-terminal region of an antibody heavy chain that contains at least a portion of the constant region. The term includes native sequence Fc regions and variant Fc regions. For example, a human IgG heavy chain Fc region may extend from Cys226, or from Pro230, to the carboxyl-terminus of the heavy chain.

An immunoglobulin may be monoclonal or polyclonal. The term "polyclonal" refers to immunoglobulins that are heterogenous populations of immunoglobulin molecules, derived for example from the sera of animals immunized with an antigen or an antigenic functional derivative thereof. For the production of polyclonal immunoglobulins, one or more of various host animals may be immunized by injection with the antigen. Various adjuvants may be used to increase the immunological response, depending on the host species.

"Monoclonal immunoglobulins", also called "monoclonal antibodies", are substantially homogenous populations of immunoglobulins to a particular antigen. They may be obtained by any technique which provides for the production of immunoglobulin molecules by continuous cell lines in culture. Monoclonal immunoglobulins may be obtained by methods well known to those skilled in the art (see for example, Köhler et al., Nature (1975) 256, 495-497, and U.S. Pat. No. 4,376,110). An immunoglobulin or immunoglobulin fragment with specific binding affinity can be isolated, enriched, or purified from a prokaryotic or eukaryotic organism. Routine methods known to those skilled in the art enable production of both immunoglobulins or immunoglobulin fragments and proteinaceous binding molecules with immunoglobulin-like functions, in both prokaryotic and eukaryotic organisms.

The term "bispecific antibody" according to the current invention refers to an antibody construct which is at least bispecific, i.e. the construct comprises at least a first binding domain and a second binding domain, wherein the first binding domain binds to one target or antigen (here ALK-1) and the second binding domain binds to another antigen or target (here BMPR-2). Antibody constructs according to the invention thus comprise specificities for at least two different antigens or targets. Bispecific antibody constructs according to the invention also encompass multispecific antibody constructs comprising multiple binding domains/binding sites, such as trispecific antibody constructs, where the construct comprises three binding domains.

Bispecific antibody formats comprise IgG-like and non-IgG-like antibodies (Fan et al (2015) Journal of Hematology & Oncology. 8: 130). IgG-like antibodies have a monoclonal antibody (mAb) structure of two Fab arms and one Fc region, wherein the two Fab sites bind different antigens. The most common IgG-like antibody types comprise two Fab regions, and the Fc region. Each heavy and light chain pair may be from a unique mAb. The Fc region is usually made from the two heavy chains. These BsABs can be manufactured for instance with the quadroma or the hybrid hybridoma method or another method known in the art. Non-IgG-like BsABs lack an Fc region. Non-IgG-like BsABs include chemically linked Fabs, comprising only the Fab regions, and various types of bivalent and trivalent single-chain variable fragments (scFvs). There are also fusion proteins mimicking the variable domains of two antibodies. These formats comprise bi-specific T-cell engagers (BiTEs).

Bispecific antibodies according to the current invention include but are not limited to multivalent single chain antibodies, diabodies and triabodies, and antibodies having the constant domain structure of full length antibodies to which further antigen-binding sites are linked via one or more linker or peptide-linker. Possible further antigen-binding sites comprise for example single chain Fv, VH domain and/or VL domain, Fab, (Fab)2, VHH nanobodies (Hamers-Casterman C et al., (1993) Nature 363(6428), 446-448), single domain antibodies, scFabs, or fragments of any of these.

Bispecific antibodies according to the current invention include but are not limited to Fc fusions to which further antigen-binding sites are linked via one or more linker or peptide-linker, for example N-terminal and/or C-terminal. Possible further antigen-binding sites comprise for example single chain Fv, VH domain and/or VL domain, Fab, (Fab)2, VHH nanobodies, single domain antibodies, scFabs, or fragments of any of these.

Antibodies or bispecific antibodies comprising an Fc region may or may not comprise a modification promoting the association of the first and the second subunit of the Fc domain. A "modification promoting the association of the first and the second subunit of the Fc domain" is a manipulation of the peptide backbone or the post-translational modifications of an Fc domain subunit that reduces or prevents the association of a polypeptide comprising the Fc domain subunit with an identical polypeptide to form a homodimer. A modification promoting association as used herein particularly includes separate modifications made to each of the two Fc domain subunits desired to associate (i.e. the first and the second subunit of the Fc domain), wherein the modifications are complementary to each other so as to promote association of the two Fc domain subunits. For example, a modification promoting association may alter the structure or charge of one or both of the Fc domain subunits so as to make their association sterically or electrostatically favorable. Thus, (hetero)dimerization occurs between a polypeptide comprising the first Fc domain subunit and a polypeptide comprising the second Fc domain subunit, which might be non-identical, e.g. in the sense that further components fused to each of the subunits (e.g. antigen binding moieties) are not the same. In some embodiments the modification promoting association comprises an amino acid mutation in the Fc domain, specifically an amino acid substitution. In a particular embodiment, the modification promoting association comprises a separate amino acid mutation, specifically an amino acid substitution, in each of the two subunits of the Fc domain.

The term "linker" as used herein refers to any molecule enabling a direct topological connection of different portions of a BsAB or antibody construct. Examples for linkers establishing a covalent connection between the different antibody portions include peptide linker and non-proteinaceous polymers, including but not limited to polyethylene glycol (PEG), polypropylene glycol, polyoxyalkylenes, or copolymers of polyethylene glycol, polypropylene glycol.

The term "peptide linker" according to the current invention refers to a sequence of amino acids, wherein said sequence links the amino acid sequence of a first portion of an antibody construct to a second portion of an antibody construct. For example, a peptide linker can link a first (variable and/or binding) domain to a second variable and/or binding) domain of the antibody construct. For example, a peptide linker can also link a portion of the antibody construct to another portion of the antibody construct, such as an antigen binding domain to an Fc domain or a fragment thereof. Suitable peptide linkers are described in U.S. Pat. Nos. 4,751,180, 4,935,233, WO 88/09344 and Holliger et al. (1993) Proc. Natl. Acad. Sci. USA 90:6444-6448; Poljak et al. (1994) Structure 2:1121-1123. Preferably, the peptide linker has a length that is adequate to link two entities in such a way that they maintain their conformation relative to each other, such that the desired activity is not hampered. In particular, where the antibody construct according to the current invention comprises one or more linker, the one or more linker preferably have a length and sequence which do not disturb the individual binding specificities of the binding domains. The linker peptide may or may not predominantly include the following amino acid residues: Gly, Ser, Ala, or Thr.

Useful linkers include glycine-serine polymers, including for example $(GS)_n$, $(GSGGS)_n$, $(GGGGS)_n$, $(GGGS)_n$, and $(GGGGS)_nG$, where n is an integer of at least one (and preferable 2, 3, 4, 5, 6, 7, 8, 9, 10). Useful linkers also include glycine-alanine polymers, alanine-serine polymers, and other flexible linkers. Linker sequences may include any sequence of any length of CL/CH1 domain or not all residues of CL/CH1 domain.

Linkers can be derived from immunoglobulin light chain, for example Cκ or Cλ. Linkers can be derived from immunoglobulin heavy chains of any isotype, including for example Cγ1, Cγ2, Cγ3, Cγ4, Cα1, Cα2, Cδ, Cα, and Cμ. Linker sequences may also be derived from other proteins such as Ig-like proteins (e.g. TCR, FcR, KIR), hinge region-derived sequences, other natural sequences from other proteins, or can be charged linkers.

Methods for linking the domains to each other according to the current invention are well known in the art and comprise for example genetic engineering. Methods for preparing fused and operatively linked bispecific single chain constructs and expressing them in mammalian cells or bacteria are well-known in the art (e.g. WO 99/54440 or Sambrook et al., Molecular Cloning: A Laboratory Manual, Cold Spring Harbor Laboratory Press, Cold Spring Harbor, N.Y., 2001).

The term "valent" according to the current invention denotes the presence of a specified number of binding sites in an antibody molecule. As such, the terms bivalent, trivalent, tetravalent denote the presence of two, three or four binding sites, respectively, in an antibody construct. The bispecific antibodies according to the invention are at least bivalent and may be multivalent, for example bivalent, trivalent, tetravalent or hexavalent.

The term "binding domain" as used herein refers to any portion of the bispecific antibody which binds to a specific target or antigen. A binding domain is an antigen binding site. A binding domain can be for example an antibody or immunoglobulin on its own or an antibody fragment. Such a binding domain may or may not have a tertiary structure which is independent from the rest of the BsAB and may or may not bind its target as an individual entity.

Bispecific antibodies, antibodies, antibody fragments or antigen binding sites can be full length from a single species. Bispecific antibodies, antibodies, antibody fragments or antigen binding sites can be chimeric. Bispecific antibodies, antibodies, antibody fragments or antigen binding sites can be fully or partially humanized, as known in the art.

Where an antibody, bispecific antibody, antibody fragment or antigen binding site according to the current invention is in a certain format, this does not exclude further modifications including but not limited to natural or synthetic attachments or fusion to other moieties. In particular, an antibody construct or a BsAB may be PEGylated or (hyper)glycosylated.

The term "BMP-9" refers to the protein Growth/differentiation factor 2. The BMP-9 protein is encoded by the gene GDF2. The BMP-9 protein comprises human, murine, and further mammalian and non-mamalian homologues. Sequence(s) for human BMP-9 are accessible via UniProt Identifier Q9UK05 (GDF2_HUMAN), for instance human isoform Q9UK05-1. Sequence(s) for murine BMP-9 are accessible via UniProt Identifier Q9WV56 (GDF2_MOUSE). Different isoforms and variants may exist for the different species and are all comprised by the term BMP-9. Also comprised are BMP-9 molecules before and after maturation, i.e., independent of cleavage of one or more pro-domains. In addition, synthetic variants of the BMP-9 protein may be generated and are comprised by the term BMP-9. The protein BMP-9 may furthermore be subject to various modifications, e.g, synthetic or naturally occurring modifications. Recombinant human BMP-9 (rhBMP-9) is commercially available or can be manufactured as known in the art.

The term "ALK-1" refers to the protein Serine/threonine-protein kinase receptor R3. Alternative names comprise SKR3, Activin receptor-like kinase 1, ALK1, TGF-B superfamily receptor type I and TSR-I. The ALK-1 protein is encoded by the gene ACVRL1. The ALK-1 protein comprises human, murine, and further mammalian homologues. Sequence(s) for human ALK-1 are accessible via UniProt Identifier P37023 (ACVL1_HUMAN), for instance human isoform P37023-1. Sequence(s) for murine ALK-1 are accessible via UniProt Identifier Q61288 (ACVL1_MOUSE). Different isoforms and variants may exist for the different species and are all comprised by the term ALK-1. In addition, synthetic variants of the ALK-1 protein may be generated, e.g. by introducing at least one mutation, and are comprised by the term ALK-1. The protein ALK-1 may furthermore be subject to various modifications, e.g, synthetic or naturally occurring modifications.

The term "BMPR-2" refers to the protein Bone morphogenetic protein receptor type-2. Alternative names comprise BMP type-2 receptor, Bone morphogenetic protein receptor type II, BMP type II receptor, BMR2, PPH1, BMPR3, BRK-3, POVD1, T-ALK, BMPRII and BMPR-II. The BMPR-2 protein is encoded by the gene BMPR2. The BMPR-2 protein comprises human, murine, and further mammalian homologues. Sequence(s) for human BMPR-2 are accessible via UniProt Identifier Q13873 (BMPR2_HUMAN), for instance human isoform 1 (identifier: Q13873-1), and human isoform 2 (identifier: Q13873-2). Sequence(s) for murine BMPR-2 are accessible via UniProt Identifier O35607 (BMPR2_MOUSE). Different isoforms and variants may exist for the different species and are all comprised by the term BMPR-2. In addition, synthetic variants of the BMPR-2 protein may be generated, e.g. by introducing at least one mutation, and are comprised by the term BMPR-2. The protein BMPR-2 may furthermore be subject to various modifications, e.g, synthetic or naturally occurring modifications.

The term "ALK-2" refers to the protein Activin receptor type-1. The ALK-2 protein is encoded by the gene ACVR1. The ALK-2 protein comprises human and further homologues. Sequence(s) for human ALK-2 are accessible via UniProt Identifier Q04771 (ACVR1_HUMAN), for instance human isoform Q04771-1. Different isoforms and variants may exist for the different species and are all comprised by the term ALK-2. In addition, synthetic variants of the ALK-2 protein may be generated and are comprised by the term ALK-2. The protein ALK-2 may furthermore be subject to various modifications, e.g, synthetic or naturally occurring modifications.

The terms "treatment" and "treating" as used herein, refer to a prophylactic or preventative measure having a therapeutic effect and preventing, slowing down (lessen), or at least partially alleviating or abrogating an abnormal, including pathologic, condition in the organism of a subject. Those in need of treatment include those already with the disorder as well as those prone to having the disorder or those in whom the disorder is to be prevented (prophylaxis). Generally a treatment reduces, stabilizes, or inhibits progression of a symptom that is associated with the presence and/or progression of a disease or pathological condition. It is an objective according to the current invention to provide bispecific antibody for use as a medicament as well as BsABs for use in the treatment of pulmonary hypertension.

The term "therapeutic effect" refers to the inhibition or activation of factors causing or contributing to the abnormal condition. A therapeutic effect relieves to some extent one or more of the symptoms of an abnormal condition or disease. The term "abnormal condition" refers to a function in the cells or tissues of an organism that deviates from their normal functions in that organism. An abnormal condition can inter alia relate to cell proliferation, cell differentiation, cell permeability, or cell survival. Examples of therapeutic effect in the context of PH and PAH are an improved barrier function for lung endothelial cells, reduced apoptosis of lung endothelial cells, reduced right ventricular hypertrophy, and a decrease in right ventricular systolic blood pressure (RVSP).

The term "pharmaceutical composition" as used herein relates to a composition for administration to a subject, preferably a human patient. In a preferred embodiment, the pharmaceutical composition comprises a composition for parenteral, transdermal, intraluminal, intraarterial or intrathecal administration or for administration by direct injection into tissue. In particular it is envisaged that said pharmaceutical composition is administered to a patient via infusion or injection. Administration of the suitable compositions may occur by different ways, such as by intravenous, intraperitoneal, subcutaneous, intramuscular, topical or intradermal administration. The pharmaceutical composition according to the current invention may further comprise a pharmaceutically acceptable carrier. Examples of a suitable pharmaceutically acceptable carrier are well known in the art and include phosphate buffered saline solutions, water, emulsions, wetting agents, sterile solutions etc. Compositions comprising a suitable pharmaceutically acceptable carrier can be formulated using conventional methods well known in the art. These pharmaceutical compositions can be administered to the subject at a suitable dose. The dosage regiment can be determined by the attending physician in view of the relevant clinical factors. Factors that may influence such a dosage regimen include size, weight, body surface area, age and sex of the subject or patient as well as time and route of administration.

As used in this document, the expression "pharmaceutically acceptable" refers to those active compounds, materials, compositions, carriers, and/or dosage forms which are, within the scope of sound medical judgment, suitable for use in contact with the tissues of human beings and animals without excessive toxicity, irritation, allergic response, or other problems or complications, commensurate with a reasonable benefit/risk ratio.

An "effective close" of a compound or BsAB is an amount—either as a single dose or as part of a series of doses—which at the dosage regimen applied yields a desired effect.

The "osteogenic activity" of a compound or an antibody is the ability of the compound or antibody to promote osteogenesis (formation of bones) in cells or tissue as monitored for example by osteocalcin induction and/or matrix mineralization. For example, at an effective dose a compound or an antibody with osteogenic activity can induce the differentiation of mouse myoblast cell line C2C12 (ATCC, catalogue number CRL-1772) from myoblastic to osteoblastic.

Embodiments

According to a first aspect, the current invention comprises a bispecific antibody (BsAB), wherein said antibody comprises two binding domains, wherein the first binding domain is specific for ALK-1 and the second binding domain is specific for BMPR-2.

In some embodiments, the BsAB bridges the ALK-1/BMPR-2 complex or brings the complex in a structural configuration, which is competent for the downstream signaling steps.

BsABs according to the current invention are usually characterized by a longer half-life than the natural ligand of the ALK-1/BMPR-2 complex, BMP-9, or its variants. Furthermore, BsABs according to the current invention can be produced with high yields. Affinities are better accessible than for BMP-9 and its variants, because the BsABs or their binding domains can be easily maturated, or screening approaches can be used to detect binders with optimized binding capabilities. For BsABs, each binding site can be optimized individually. Finally, even in the absence of functional BMP-9 signaling, e.g. due to a genetic defect, an antibody approach could still be able to rescue the ALK-1/BMPR-2 signaling cascade.

The antibodies disclosed herein specifically bind to ALK-1 and BMPR-2; i.e., they bind to their targets with an affinity that is higher (e.g., at least two-fold higher) than their binding affinity for an irrelevant antigen (e.g., bovine serum albumin (BSA), casein).

In some embodiments according to the first aspect, the BsABs specifically binds an extracellular domain of ALK-1 and/or an extracellular domain of BMPR-2. In some embodiments, the ALK-1 is human ALK-1 or a fragment thereof, and/or the BMPR-2 is human BMPR-2 or a fragment thereof. In some embodiments, the BsAB binds an extracellular domain of human ALK-1 or a fragment thereof and/or an extracellular domain of human BMPR-2 or a fragment thereof.

In some embodiments, the BsAB binds to ALK-1 with a Kd of at most about $10^{-4}$ M to about $10^{-13}$ M (e.g., $10^{-4}$ M, $10^{-4.5}$ M, $10^{-5}$ M, $10^{-5.5}$ M, $10^{-6}$M, $10^{-6.5}$ M, $10^{-7}$ M, $10^{-7.5}$ M, $10^{-8}$ M, $10^{-8.5}$ M, $10^{-9}$ M, $10^{-9.5}$ M, $10^{-10}$ M, $10^{-10.5}$ M, $10^{-11}$ M, $10^{-11.5}$ M, $10^{-12}$ M, $10^{-12.5}$ M, $10^{-13}$ M).

In some embodiments, the BsAB binds to BMPR-2 with a Kd of at most about $10^{-4}$ M to about $10^{-13}$ M (e.g., $10^{-4}$ M, $10^{-4.5}$ M, $10^{-5}$ M, $10^{-5.5}$ M, $10^{-6}$M, $10^{-6.5}$ M, $10^{-7}$ M, $10^{-7.5}$ M, $10^{-8}$ M, $10^{-8.5}$ M, $10^{-9}$ M, $10^{-9.5}$ M, $10^{-10}$ M, $10^{-10.5}$ M, $10^{-11}$ M, $10^{-11.5}$ M, $10^{-12}$ M, $10^{-12.5}$ M, $10^{-13}$ M).

In some embodiments, the BsAB binds to ALK-1 and BMPR-2 with a Kd of at most about $10^{-4}$ M to about $10^{-13}$ M (e.g., $10^{-4}$ M, $10^{-4.5}$ M, $10^{-5}$ M, $10^{-5.5}$ M, M, $10^{-6.5}$ M, $10^{-7}$ M, $10^{-7.5}$ M, $10^{-8}$ M, $10^{-8.5}$ M, $10^{-9}$M, $10^{-9.5}$M, $10^{-10}$ M, $10^{-10.5}$ M, $10^{-11}$ M, $10^{-11.5}$ M, $10^{-12}$ M, $10^{-12.5}$ M, $10^{-13}$ M).

In some embodiments, the BsAB binds to ALK-2 or an antigen according to SEQ ID 117 with a Kd of more than about $10^{-4}$ M, $10^{-4.5}$ M, $10^{-5}$ M, $10^{-5.5}$ M, $10^{-6}$ M, $10^{-6.5}$ M or $10^{-7}$ M. In some preferred embodiments, the BsAB does not bind to ALK-2 with an affinity that is higher (e.g. at least two fold higher) than the binding affinity for an irrelevant antigen such as BSA.

The Kd of antibody binding to an antigen can be assayed using any method known in the art including, for example, immunoassays such as enzyme-linked immununospecific assay (ELISA), Bimolecular Interaction Analysis (BIA) (e.g., Sjolander & Urbaniczky; Anal. Chem. 63:2338-2345, 1991; Szabo, et al., Curr. Opin. Struct. Biol. 5:699-705, 1995), and fluorescence-activated cell sorting (FACS) for quantification of antibody binding to cells that express an antigen. BIA is a technology for analyzing biospecific interactions in real time, without labeling any of the interactants (e.g., BIACORE™). Changes in the optical phenomenon surface plasmon resonance (SPR) can be used as an indication of real-time reactions between biological molecules.

In some embodiments, the antibody according to the current invention, in addition to binding domains for ALK-1 and BMPR-2 further comprises a binding domain for a ligand of the ALK-1/BMPR-2 receptor such as BMP-9, or for another molecule involved in ALK-1/BMPR-2 signaling.

Except if there is an obvious incompatibility for a person skilled in the art, each of the embodiments describing the binding capabilities can be combined with each of the embodiments describing the format of the antibody.

In some preferred embodiments, the BsAB or at least a portion thereof is monoclonal. In some embodiments, the BsAB is chimeric. In some preferred embodiments, the BsAB is fully or partially humanized.

In some embodiments according to the first aspect, the format of the BsAB is IgG-like. In some embodiments according to the first aspect, the format of the BsAB is non-IgG-like. In some embodiments according to the first aspect, the bispecific antibody is in a format selected from the group consisting of (scFv)2, scFv-single domain mAb, diabodies, and oligomers of any of the aforementioned formats. In a preferred embodiment, the format of the BsAB according to the first aspect or any other aspect is scFv-Fc (kih).

In some embodiments according to the first aspect, the bispecific antibody comprises at least one scFv domain, which includes a variable heavy domain and a variable light domain, linked together by a scFv linker. As discussed, for this format, a number of suitable scFv linkers is available, including traditional peptide bonds, generated by recombinant techniques (Huston et al. (1988) Proc. Natl. Acad. Sci USA 85:5879-5883).

In some embodiments according to the first aspect, the bispecific antibody comprises at least one linker. In some embodiments, the at least one linker comprises at least one peptide linker. In some embodiments, the at least one peptide linker is from 1 to 50 amino acids in length, preferably 1 to 30 amino acids in length, most preferably 4 to 16 amino acids in length. In some embodiments, the at least one peptide linker has a size of 4, 5, 6, 7, 8, 9, 10, 11, 12, 13, 14, 15 or 16 amino acids. In some embodiments, the at least one peptide linker has a size of 4, 3, 2, or one amino acid. In a preferred embodiment, the at least one peptide linker is rich of glycine. In one embodiment, the at least one peptide linker consists of a single glycine. In a preferred embodiment, the one or more linker does not promote secondary structures. In a preferred embodiment, the BsAB comprises a GGGGSnG peptide linker, wherein n is an integer selected from the list consisting of 1, 2, 3, 4, 5, 6, 7, 8, 9 and 10.

Where a BsAB comprises a linker, each embodiment describing the linker can be and is specifically suggested to be combined with each embodiment describing the format of the BsAB, and/or each embodiment describing the binding capabilities, except if a person skilled in the art would consider the combination to be obviously incompatible.

In a preferred embodiment, the BsAB comprises at least one $(GGGGS)_3G$ peptide linker, wherein at least one of the at least one linker links an scFv region and a Fc region. In a preferred embodiment, the BsAB comprises at least one $(GGGGS)_3$ peptide linker, wherein at least one of the at least one linker links VH chain and VL chain.

Bispecific antibodies do usually not occur naturally and are usually artificial hybrid antibodies or immunoglobulins. Bispecific antibodies can for example be prepared as full length antibodies or antibody fragments. A variety of formats for bispecific antibodies and methods to produce them are well known in the art. These methods include but are not limited to fusion of hybridomas or linking of Fab' fragments (Songsivilai & Lachmann, Clin. Exp. Immunol 79:315-321 (1990)).

Techniques for making bi- or multispecific antibodies include, but are not limited to, recombinant co-expression of two immunoglobulin heavy chain-light chain pairs having different specificities (see Milstein and Cuello, Nature 305: 537 (1983)), WO 93/08829, and Traunecker et al., EMBO J. 10: 3655 (1991)), and chemical conjugation of two different monoclonal antibodies (see Staerz et al. (1985) Nature 314(6012): 628-31). Multispecific antibodies may also be made by cross-linking two or more antibodies or fragments (see, e.g., U.S. Pat. No. 4,676,980, and Brennan et al., Science, 229: 81 (1985)); using leucine zippers to produce bi-specific antibodies (see, e.g., Kostelny et al., J Immunol, 148(5): 1547-1553 (1992)); using "diabody" technology for making bispecific antibody fragments (see, e.g., Hollinger et al., Proc. Natl. Acad. Sci. USA, 90:6444-6448 (1993)); and using single-chain Fv (sFv) dimers (see, e.g. Gruber et al., J. Immunol, 152:5368 (1994)); and preparing trispecific antibodies as described, e.g., in Tutt et al. J. Immunol 147: 60 (1991) and by controlled Fab arm exchange (cFAE) Labrijn A F et al. Proc Natl Acad Sci USA 2013; 110:5145-50.

In some preferred embodiments according to the first aspect, the bispecific antibody comprises at least one Fc domain. In a preferred embodiment, where the BsAB comprises at least one Fc region, the BsAB further comprises a modification promoting the association of the first and the second subunit of the Fc domain, such as a knob-in-hole mutation.

In a preferred embodiment the modification promoting association is based on the "knob-in-hole" (kih) engineering (see, e.g., U.S. Pat. No. 5,731,168, Ridgway et al., Protein Engineering 9(7):617 (1996); Atwell et al., J. Mol. Biol. 1997 270:26; U.S. Pat. No. 8,216,805). Knobs into holes technology relies on introducing a mutation for a large amino acid in the heavy chain from one mAb, and a mutation for a small amino acid in the other mAb's heavy chain. This allows better fitting of the target heavy chains (and their corresponding light chains) and makes BsAB production more reliable. In addition, as described in Merchant et al., Nature Biotech. 16:677 (1998), these "knob-in-hole" mutations can be combined with disulfide bonds to skew formation to heterodimerization.

In some preferred embodiments according to the current invention, the BsAB is a scFv-Fc (kih) construct combining two monospecific antibody scFv fragments linked to heterodimeric human IgG Fc, wherein the first scFv fragment specifically binds human BMPR-2 or a fragment thereof and wherein the second scFv fragment specifically binds human ALK-1 or a fragment thereof. The IgG Fc can be for example an IgG2 or any other type of immunoglobulin.

In some embodiments, the first binding domain of a BsAB according to the first aspect is a VHH binding domain and/or the second binding domain of the BsAB is a VHH binding domain. In some of these embodiments, the BsAB furthermore comprises an Fc domain, wherein the first subunit of the Fc domain comprises one or more knob mutations and the second subunit of the Fc domain comprises one or more hole mutations according to the knobs into holes method.

In some embodiments the first binding domain of the BsAB comprises a Fab or fragment thereof and/or the second binding domain comprises a Fab or fragment thereof. In some of these embodiments, the BsAB furthermore comprises an Fc domain, wherein the first subunit of the Fc domain comprises one or more knob mutations and the second subunit of the Fc domain comprises one or more hole mutations according to the knobs into holes method.

In some embodiments, the BsAB according to the first aspect comprises (i) SEQ IDs 2-7, and/or (ii) SEQ IDs 9-14, and/or (iii) SEQ IDs 30-35, and/or (iv) SEQ IDs 37-42, and/or (v) SEQ IDs 37-42.

Each embodiment described for the first aspect can be and is specifically suggested to be combined with each embodiment according to the second aspect, except if a person skilled in the art considers the combination obviously incompatible. Each embodiment described for the first aspect can be and is specifically suggested to be combined with each combination of embodiments according to the second aspect, except if a person skilled in the art considers the combination obviously incompatible. Each combination of embodiments described for the first aspect can be and is specifically suggested to be combined with each embodiment according to the second aspect, except if a person skilled in the art considers the combination obviously incompatible. Each combination of embodiments described for the first aspect can be and is specifically suggested to be combined with each combination of embodiments according to the second aspect, except if a person skilled in the art considers the combination obviously incompatible.

According to a second aspect, the current invention comprises a BsAB according to the first aspect, which has agonistic activity for ALK-1/BMPR-2 signaling in a target cell.

BsAB with agonistic activity for ALK-1/BMPR-2 signaling have a higher probability to revert vessel muscularization and restore barrier function in lung endothelial cells by decreasing the endothelial permeability.

In a preferred embodiment, the target cell expresses ALK-1 and BMPR-2, either naturally or after manipulation. In one embodiment, the target cell is the U2OS ACVRL1/BMPR-2 Dimerization Cell Line (DiscoverX Corporation).

In a preferred embodiment according to the second aspect, the antibody has agonistic activity for ALK-1/BMPR-2 signaling in a target cell, wherein said target cell is an endothelial cell.

In a healthy mammal, BMPR-2 and ALK-1 are primarily expressed on endothelial cells. In some embodiments, the endothelial cell is derived from a mammalian donor, such as mouse, rat, rodent, pig, dog and human. In some preferred embodiments, the endothelial cell is a lung cell. In some preferred embodiments, the endothelial cell is a human lung cell or a rodent lung cell. In some preferred embodiments, the endothelial cell is selected from the list comprising HPAEC, HAoEC, HCAEC and HMVEC-L cells Agonistic activity for ALK-1/BMPR-2 signaling can be assessed with multiple methods and readout systems. According to the current invention a BsAB is called agonistic for ALK-1/BMPR-2 signaling, if the BsAB shows agonistic activity in at least one of the following assays or methods.

A first class of methods comprises methods including various well described biophysical methods for the detection of structural changes occurring upon signaling via ALK-1/BMPR-2. A preferred method to evaluate occurrence of the initial step of ALK-1/BMPR-2 signaling is via the PathHunter Dimerization assay (U2OS ACVRL1/BMPR-2 Dimerization Cell Line, DiscoverX Corporation). The assay detects ligand induced dimerization of two subunits of a receptor-dimer pair. The cells have been engineered to co-express one receptor subunit fused to Enzyme Donor (ED), and a second dimer partner fused to Enzyme Acceptor (EA). Binding of an agonist according to the current invention to one or both receptor subunits induces the interaction of the dimer partners, forcing complementation of the two enzyme fragments. This results in the formation of a functional enzyme that hydrolyzes a substrate to generate a chemiluminescent signal as readout.

In a preferred embodiment, the BsAB according to the second aspect promotes dimerization of ALK-1 and BMPR-2. Suitable assays to detect dimerization of ALK-1 and BMPR-2 are the PathHunter Dimerization assay (U2OS ACVRL1/BMPR-2 Dimerization Cell Line, DiscoverX Corporation) or any assay using the principle of the PathHunter Dimerization assay as described herein.

According to the current invention BsABs are called agonistic for ALK-1/BMPR-2 signaling, if an EC50 can be determined for the BsAB by using the PathHunter U2OS ALK-1/BMPR-2 dimerization assay. However, even if no EC50 can be determined by the PathHunter U2OS ALK-1/BMPR-2 dimerization assay, a BsAB according to the current invention may still be called agonistic for ALK-1/BMPR-2 signaling, if an alternative method described below to assay agonistic activity for ALK-1/BMPR-2 signaling shows significant agonistic activity for the BsAB. For example, further methods described herein to assay agonistic activity for ALK-1/BMPR-2 signaling include SMAD1 and/or 5 phosphorylation assays, ApoOne/CTB assay, and assays on endothelial barrier function in vitro or in sepsis mouse models, MCT rat or Sugen/Hypoxia-induced pulmonary hypertension rat models.

Figure 8:
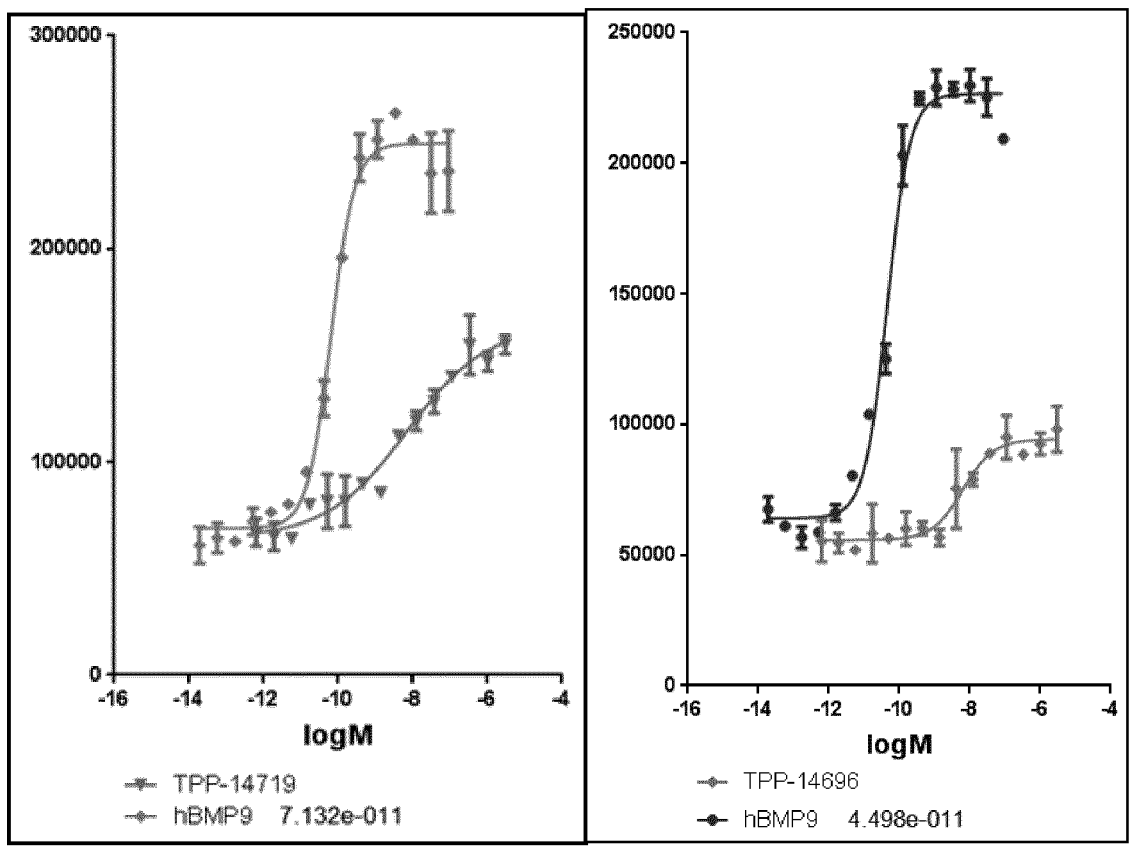
FIG. 8 shows the results for the agonistic BsAbs TPP-14669 and TPP-14719 in the PathHunter U2OS ALK-1/BMPR-2 dimerization cell assay obtained from DiscoverX Corporation (catalogue number 93-0962C3).

Half maximal effective concentration (EC50) refers to the concentration of a drug, antibody or toxicant which induces a response halfway between the baseline and maximum after a specified exposure time. An EC50 can be determined for an antibody of the current invention, if an inflection point can be determined by mathematical modeling (e.g., non-linear regression) of the dose-response curve describing the relationship between applied antibody concentration and chemiluminescent signal. For example, if the dose-response curve follows a sigmoidal curve, an EC50 can be determined. If not stated otherwise the EC50 as mentioned herein is the EC50 for agonistic activity, e.g. as determined from an ALK-1/BMPR-2 dimerization assay (FIG. 8).

In order to describe the magnitude of the agonistic activity of a bispecific antibody according to the current invention, the respective EC50 for recombinant BMP-9 as well as for the antibody are determined by titration as described in the manufacturer's instructions for the PathHunter U2OS ACVRL1/ACVR2 Dimerization Cell Line. Of note, the exposure time is preferably comparable for both, antibody and BMP-9. Under usual conditions, for an assay performed based on manufacturer's instructions, the EC50 for BMP-9 is about 0.1 nM. In a preferred embodiment, the EC50 values for the antibody and for BMP-9 are in the same order of magnitude. In another preferred embodiment the EC50 values for the BsAB are lower or in the same order of magnitude as the EC50 for TPP-14696 or TPP-14719 (FIG. 8).

In a preferred embodiment, the BsAB according to the second aspect promotes dimerization of ALK-1 and BMPR-2. For example, this can be shown in the PathHunter Dimerization assay using the U2OS ACVRL1/BMPR-2 Dimerization Cell Line. In a preferred embodiment, the BsAB according to the second aspect promotes dimerization of ALK-1 and BMPR-2 in the PathHunter Dimerization assay using the U2OS ACVRL1/BMPR-2 Dimerization Cell Line. A BsAB promotes dimerization of ALK-1 and BMPR-2 in the PathHunter Dimerization assay using the U2OS ACVRL1/BMPR-2 Dimerization Cell Line, if an EC50 can be determined for the BsAB by using the PathHunter U2OS ALK-1/BMPR-2 dimerization assay.

In some embodiments for a BsAB which is agonistic for ALK-1/BMPR-2 signaling, the ratio between the determined EC50 for the antibody and the determined EC50 for recombinant BMP-9 is between 0.000001 and 1000000.

In some embodiments for a BsAB which is agonistic for ALK-1/BMPR-2 signaling, the ratio between the determined EC50 for the antibody and the determined EC50 for recombinant BMP-9 is between 0.00001 and 100000.

In some further embodiments for a BsAB which is agonistic for ALK-1/BMPR-2 signaling, the ratio between the determined EC50 for the antibody and the determined EC50 for recombinant BMP-9 is between 0.0001 and 10000.

In some preferred embodiment for a BsAB which is agonistic for ALK-1/BMPR-2 signaling, the ratio between the determined EC50 for the antibody and the determined EC50 for recombinant BMP-9 is between 0.001 and 1000.

In some even more preferred embodiments for a BsAB which is agonistic for ALK-1/BMPR-2 signaling, the ratio between the determined EC50 for the antibody and the determined EC50 for recombinant BMP-9 is between 0.01 and 100.

In some preferred embodiment for a BsAB which is agonistic for ALK-1/BMPR-2 signaling, the ratio between the determined EC50 for the antibody and the determined EC50 for recombinant BMP-9 is between 0.1 and 10.

In a preferred embodiment for a BsAB which is agonistic for ALK-1/BMPR-2 signaling, the ratio between the determined EC50 for the antibody and the determined EC50 for recombinant BMP-9 is between about n and about m, wherein n is an element of a first set consisting of 0.0001, 0.0002, 0.0003, 0.0004, 0.0005, 0.0006, 0.0007, 0.0008, 0.0009, 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, and 1, and wherein m is an element of a second set consisting of 1.1, 1.2, 1.3, 1.4, 1.5, 1.6, 1.7, 1.8, 1.9, 2, 3, 4, 5, 6, 7, 8, 9, 10, 20, 30, 40, 50, 60, 70, 80, 90, 100. In this particular context, the term "about" refers to +/−10%.

In a preferred embodiment for a BsAB which is agonistic for ALK-1/BMPR-2 signaling, the EC50 of the bispecific antibody according to the current invention is higher than or equal to the EC50 of BMP-9.

Alternative methods to evaluate agonistic activity include for example methods for the quantification of one or more target gene products of ALK-1/BMPR-2 signaling. Suitable methods are well known in the art and comprise gene arrays and quantitative real-time PCR analysis, mass spectrometry based proteomics and Western Blot analysis. A BsAB is called agonistic for ALK-1/BMPR-2 signaling, if upon administration of an effective dose of said BsAB at least one suitable target gene product is significantly upregulated in a target cell. The set of suitable target genes of ALK-1/BMPR-2 signaling comprises various genes, such as angiogenesis related genes IL-8, ET-1, ID1, HPTPη and TEAD4 (Lux et al, BMC Cardiovascular Disorders 2006; 6:13). Lux et al. describe a model for the identification of target genes for ALK-1 signaling, wherein human microvascular endothelial cell line HMEC-1 was infected with a recombinant constitutively active ALK-1 adenovirus for the subsequent analysis of target gene expression.

For human pulmonary artery endothelial cells, treatment with rhBMP-9 activated key components of the canonical BMP signaling in endothelial cells, as demonstrated by Western Blot analysis for SMAD1 and SMAD5 phosphorylation. A further class of suitable methods to evaluate the agonistic activity with respect to ALK-1/BMPR-2 signaling therefore relies on detecting an increase in phosphorylated SMADs or other chemical modifications occurring during the signal transduction. Suitable methods according to this class are likewise well described in the art and include mass spectrometry based phosphoproteomics and Western Blot analysis as described in example 5 (see also FIG. 2).

In a preferred embodiment according to the second aspect, an effective dose of the BsAB promotes phosphorylation of SMAD1 and/or SMAD5.

According to the current invention, BsABs leading to an induction of SMAD1 and/or SMAD5 phosphorylation in endothelial cells comparable to the natural ligand BMP-9 are considered to be potent agonists for ALK-1/BMPR-2 signaling. Of note, required concentrations (effective doses) of BsAB and BMP-9 may strongly deviate from each other.

In this particular context, for a BsAB or a compound, an "effective dose" for phosphorylation of a SMAD is a concentration or amount of said BsAB or of said compound, where a signal can be detected by Western Blot or by phosphoproteomic analysis, and where said signal indicates the phosphorylation of that SMAD in an endothelial cell.

A BsAB or compound is called agonistic for ALK-1/BMPR-2 signaling, if an effective dose of said antibody or compound induces phosphorylation of SMAD1 or SMAD5 in a target cell. For example, for a specific target cell, effective doses of rhBMP-9 for phosphorylation of SMAD5 are 1 ng/ml and 10 ng/ml (see FIG. 2). Of note, within this context, a multitude of effective doses may exist.

In one embodiment for a BsAB which is agonistic for ALK-1/BMPR-2 signaling according to the second aspect, at least one effective dose for phosphorylation of SMAD1 and/or SMAD5 is in the range from 0.0001 ng/ml to 100 µg/ml.

In one embodiment for a BsAB which is agonistic for ALK-1/BMPR-2 signaling according to the second aspect, at least one effective dose for phosphorylation of SMAD1 and/or SMAD5 is in the range from 0.001 ng/ml to 10 µg/ml.

In one embodiment for a BsAB which is agonistic for ALK-1/BMPR-2 signaling according to the second aspect, at least one effective dose for phosphorylation of SMAD1 and/or SMAD5 is in the range from 0.01 ng/ml to 1 µg/ml.

In one embodiment for a BsAB which is agonistic for ALK-1/BMPR-2 signaling according to the second aspect, at least one effective dose for phosphorylation of SMAD1 and/or SMAD5 is in the range from 0.1 ng/ml to 0.1 µg/ml.

In one embodiment for a BsAB which is agonistic for ALK-1/BMPR-2 signaling according to the second aspect, at least one effective dose for phosphorylation of SMAD1 and/or SMAD5 is in the range from 1 ng/ml to 10 ng/ml.

Recombinant human BMP-9 (rhBMP-9) reduced apoptosis of human pulmonary endothelial cells (HPAEC) in vitro. In particular, treatment with 5 ng/ml rhBMP-9 overnight reduced apoptosis in human PAECs, as shown with two independent assays, the ApoOne/CTB assay as well as a PARP-based Western Blot analysis. Another way to assess agonistic activity with respect to ALK-1/BMPR-2 signaling of a BsAB is therefore by analyzing the anti-apoptotic activity of the BsAB using primary endothelial cells, such as HPAEC, HAoEC, HCAEC or HMVEC-L cells. The anti-apoptotic activity can be analyzed using various assays, including the ApoOne/CTB assay as described in example 6.

In some preferred embodiments according to the second aspect, an effective dose of said BsAB has an anti-apoptotic effect in endothelial cells, i.e. an effective dose of said BsAB reduces the apoptosis or apoptotic index of endothelial cells observed upon induction of apoptosis.

In some of these preferred embodiments, an effective dose of said BsAB reduces the apoptosis or apoptotic index of endothelial cells treated with an effective dose of TNFα and/or cycloheximide (CHX). In some other or the same of these preferred embodiments, an effective dose of said BsAB reduces the apoptosis or apoptotic index of endothelial cells observed upon starvation of the cells, e.g. as described in example 6. As known in the art apoptotic index (caspase 3/7 activity per live cell) is a measure for apoptosis. In some of the aforementioned preferred embodiments an effective dose of said BsAB reduces the apoptosis of endothelial cells treated with an effective dose of TNFα and/or cycloheximide (CHX). In some of the aforementioned preferred embodiments an effective dose of said BsAB reduces the apoptosis of endothelial cells observed upon starvation of the cells. In some of the aforementioned preferred embodiments an effective dose of said BsAB reduces the apoptotic index of endothelial cells treated with an effective dose of TNFα and/or cycloheximide (CHX). In some of the aforementioned preferred embodiments an effective dose of said BsAB reduces the apoptotic index of endothelial cells observed upon starvation of the cells.

In some embodiments, the endothelial cells are selected from the list comprising HPAEC, HAoEC, HCAEC and HMVEC-L cells. In a preferred embodiment, treatment with an effective dose of TNFα and cycloheximide (CHX) occurs as described in example 6 and/or FIG. 3. In a preferred embodiment, apoptotic index is determined for HPAEC cells, 4 hours after treatment with 10 ng/ml TNFα and 20 µg/ml cycloheximide (CHX). BsABs leading to a decrease of the apoptotic index (caspase 3/7 activity per live cell) in at least one endothelial cell line are considered to be agonistic with respect to ALK-1/BMPR-2 signaling.

BsABs leading to a decrease of the apoptotic index (caspase 3/7 activity per live cell) in at least one endothelial cell line, where the decrease is comparable to the decrease induced by treatment with BMP-9 are considered to be potent agonists with respect to ALK-1/BMPR-2 signaling.

In one embodiment for a BsAB which is agonistic for ALK-1/BMPR-2 signaling according to the second aspect, the apoptotic index after treatment with BsAB is between <1% and 95% of the apoptotic index for the vehicle control.

In one embodiment for an BsAB which is agonistic for ALK-1/BMPR-2 signaling according to the second aspect, the apoptotic index after treatment with BsAB is between <1% and 90% of the apoptotic index for the vehicle control.

In one embodiment for an BsAB which is agonistic for ALK-1/BMPR-2 signaling according to the second aspect, the apoptotic index after treatment with BsAB is between <1% and 85% of the apoptotic index for the vehicle control.

In one embodiment for an BsAB which is agonistic for ALK-1/BMPR-2 signaling according to the second aspect, the apoptotic index after treatment with BsAB is between <1% and 80% of the apoptotic index for the vehicle control.

In one embodiment for an BsAB which is agonistic for ALK-1/BMPR-2 signaling according to the second aspect, the apoptotic index after treatment with BsAB is between <60% and 80% of the apoptotic index for the vehicle control.

In a preferred embodiment for an BsAB which is agonistic for ALK-1/BMPR-2 signaling according to the second aspect, the apoptotic index after treatment with BsAB is between about n % and about m %, wherein n is an element of a first set consisting of 60, 61, 62, 63, 64, 65, 66, 67, 68, 69, and 70, and wherein m is an element of a second set consisting of 71, 72, 73, 74, 75, 76, 78, 79, and 80. In this particular context, the term "about" refers to +/−0.5.

Figure 4:
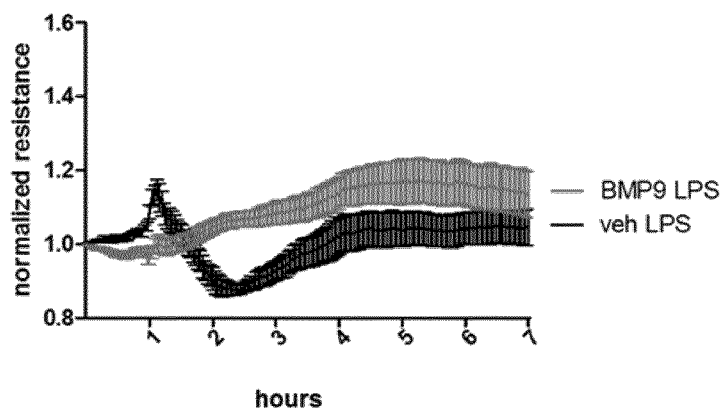
FIG. 4 illustrates the effect of human BMP-9 on the electrical resistance of the HPAEC monolayer exposed to LPS. 400 ng/ml LPS, which decreases the electrical resistance and thus the endothelial barrier function in the absence of BMP-9, has no effect on the HPAEC when pre-incubated with 20 ng/ml BMP-9 for 1 h.
Figure 5:
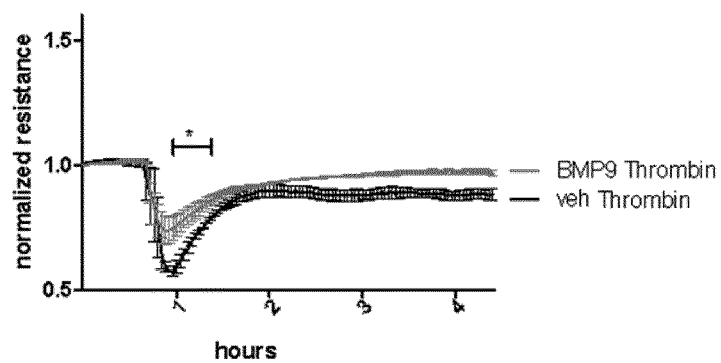
FIG. 5 illustrates the effect of human BMP-9 (BMP-9) on the electrical resistance of the HPAEC monolayer exposed to thrombin. 20 ng/ml BMP-9 significantly reduced the effect of 0.5 U/ml thrombin on the electrical resistance and thus the endothelial barrier function of the HPAEC monolayer.

Another way to assess agonistic activity with respect to ALK-1/BMPR-2 signaling of a BsAB is by using an assay for analyzing the preservation of endothelial barrier function in vitro. An example for an in vitro assay is described in example 7 (see also FIGS. 4 and 5). Agonistic activity for ALK-1/BMPR-2 signaling induced by BMP-9 inhibits the LPS-induced decrease of electrical resistance in primary human pulmonary artery endothelial cells in vitro. In this setup, electrical resistance is a suitable readout for both ALK-1/BMPR-2 signaling and endothelial barrier function.

Suitable endothelial cells for such an in vitro assay include primary human endothelial cells, human Pulmonary Artery Endothelial Cells (HPAEC), human Umbilical Vein Endothelial Cells (HUVEC), human Aortic Endothelial Cells (HAoEC), Human Coronary Artery Endothelial Cells (HCAEC), human Pulmonary Artery Endothelial Cells (HPAEC) and human lung microvascular endothelial cells (HMVEC-L). After 1 h measuring the baseline electrical resistance in the presence of vehicle (veh), BMP-9, or BsABs, one or more substances are added which enhance the endothelial permeability or impair the barrier function of the endothelial cell layer. Examples for such substances are LPS and thrombin. The effect of BsABS on the endothelial barrier function is compared to vehicle and BMP-9.

BsABs preserving the endothelial electrical resistance of endothelial monolayers, and thus the endothelial barrier function in a BMP 9-like manner are considered to be potent agonists for ALK-1/BMPR-2 signaling.

BsABs significantly inhibiting thrombin/LPS-induced decrease of electrical resistance in endothelial cells are considered to be agonistic with respect to ALK-1/BMPR-2 signaling.

In a preferred embodiment for a BsAB according to the second aspect, pre-incubation with an effective dose of BsAB significantly reduces the effect of an effective dose of thrombin on electrical resistance for at least one endothelial cell line. In some embodiments, the effective dose of thrombin is 0.5 U/ml.

In a preferred embodiment for a BsAB according to the second aspect, pre-incubation with an effective dose of BsAB significantly reduces the effect of an effective dose of LPS on electrical resistance for at least one endothelial cell line. In some embodiments, the effective dose of LPS is 400 ng/ml.

An alternative way to evaluate agonistic activity of a BsAB for ALK-1/BMPR-2 signaling is by using an assay for analyzing the preservation of endothelial barrier function in vivo. A suitable model is a mouse model for sepsis as described in example 8. According to this method, BMP-9 reduces the number of white blood cells infiltrating the lung in a mouse sepsis model (see FIG. 6 for an effect on counts of white blood cells in the broncho-alveolar lavage fluid).

BsABs reducing the invasion of white blood cells or leakage of proteins into the lung in a BMP 9-like manner are considered to be potent agonists for ALK-1/BMPR-2 signaling.

BsABs which significantly reduce the invasion of white blood cells (WBCs) or leakage of proteins into the lung upon LPS treatment compared to a vehicle control are considered to be agonistic for ALK-1/BMPR-2 signaling according to the current invention.

In some embodiments, pre-treatment with an effective dose of BsAB according to the second aspect reduces the number of WBCs in the broncho-alveolar lavage fluid (BALF) of a mouse model for sepsis upon treatment with an effective dose of LPS. In some embodiments, an effective dose for LPS is 5 mg/kg.

The Monocrotaline (MCT)—treated rat model is a widely used animal model of pulmonary arterial hypertension. After subcutaneous injection the pyrrolizidine alkaloid MCT is activated by the liver to the toxic MCT pyrrole which causes endothelial injury in the pulmonary vasculature within few days with subsequent remodeling of small pulmonary arteries (de novo muscularization and medial hypertrophy). As described in example 9, the Monocrotaline (MCT)—treated rat model is an alternative way to evaluate agonistic activity for ALK-1/BMPR-2 signaling according to the current invention in vivo.

A BsAB is agonistic for ALK-1/BMPR-2 signaling, if the ratio of the right to the left ventricular mass (right and left ventricles, the latter including the septum) obtained as described in example 9 is significantly reduced for animals of the Monocrotaline (MCT)—treated rat model treated with BsAB compared to the vehicle control.

In the alternative, a BsAB is also agonistic for ALK-1/BMPR-2 signaling, if under the same conditions, the plasma proBNP levels are significantly lower for animals of the Monocrotaline (MCT)—treated rat model treated with BsAB compared to the vehicle control. Plasma levels of the biomarker proBNP are determined as known in the art.

BsABs reducing the right ventricular pressure and/or the right ventricular hypertrophy and/or plasma proBNP levels in a BMP 9-like manner are considered to be potent agonists for ALK-1/BMPR-2 signaling.

The Sugen (SU5416) rat model is a widely used animal model for pulmonary arterial hypertension. Subcutaneous injections of the VEGFR-Inhibitor SU5416 in combination with housing the animals in a hypoxic atmosphere (10% 02) lead to progressive pulmonary vascular remodeling. This assay is a further option, to evaluate agonistic activity of an BsAB according to the second aspect.

A BsAB is agonistic for ALK-1/BMPR-2 signaling, if the ratio of the right to the left ventricular mass (right and left ventricles, the latter including the septum) obtained as described in example 10 is reduced for animals of the Sugen rat model treated with BsAB compared to the vehicle control.

In the alternative, a BsAB is also agonistic for ALK-1/BMPR-2 signaling, if under the same conditions the plasma proBNP levels are significantly lower for animals of the Sugen rat model treated with BsAB compared to the vehicle control.

BsABs reducing in this model the right ventricular pressure and/or the right ventricular hypertrophy and/or plasma proBNP levels in a BMP 9-like manner are considered as potent agonists for ALK-1/BMPR-2 signaling.

According to a third aspect of the current invention, the antibody according to the first aspect or the antibody according to the second aspect has a lower osteogenic activity than rhBMP-9.

BsABs with lower osteogenic activity than rhBMP-9 have a lower risk to induce bone formation as a side effect. Each embodiment described for the first aspect can be and is specifically suggested to be combined with each embodiment according to the third aspect, except if a person skilled in the art considers the combination obviously incompatible. Each embodiment described for the first aspect can be and is specifically suggested to be combined with each combination of embodiments according to the third aspect, except if a person skilled in the art considers the combination obviously incompatible. Each combination of embodiments described for the first aspect can be and is specifically suggested to be combined with each embodiment according to the third aspect, except if a person skilled in the art considers the combination obviously incompatible. Each combination of embodiments described for the first aspect can be and is specifically suggested to be combined with each combination of embodiments according to the third aspect, except if a person skilled in the art considers the combination obviously incompatible.

Each embodiment described for the second aspect can be and is specifically suggested to be combined with each embodiment according to the third aspect, except if a person skilled in the art considers the combination obviously incompatible. Each embodiment described for the second aspect can be and is specifically suggested to be combined with each combination of embodiments according to the third aspect, except if a person skilled in the art considers the combination obviously incompatible. Each combination of embodiments described for the second aspect can be and is specifically suggested to be combined with each embodiment according to the third aspect, except if a person skilled in the art considers the combination obviously incompatible. Each combination of embodiments described for the second aspect can be and is specifically suggested to be combined with each combination of embodiments according to the third aspect, except if a person skilled in the art considers the combination obviously incompatible.

Each embodiment resulting from combination of at least one embodiment according to the first aspect and at least one embodiment according to the second aspect can be combined and is specifically suggested to be combined with each embodiment according to the third aspect, except if a person skilled in the art considers the combination obviously incompatible.

Each embodiment resulting from combination of at least one embodiment according to the first aspect and at least one embodiment according to the second aspect can be combined and is specifically suggested to be combined with each embodiment obtained by combination of at least two embodiments according to the third aspect, except if a person skilled in the art considers the combination obviously incompatible.

In a particularly preferred embodiment, the BsAB according to the current invention does not bind ALK-2 or binds ALK-2 or an antigen according to SEQ ID 117 with a $K_D$ of more than $10^{-6}$ M. In a particularly preferred embodiment, the BsAB according to the third aspect does not bind to ALK-2 (see for example FIG. 9) or has equal or lower affinity for ALK-2 or for an antigen according to SEQ ID 117 than for an irrelevant antigen such as BSA. In a highly preferred embodiment the BsAB according to the third aspect does not induce dimerization of ALK-2/BMPR-2. Osteogenic activity is assumed to occur via ALK-2 signaling, hence omitting ALK-2 binding and/or dimerization can be assumed to at least partially avoid the osteogenic activity of natural BMP-9. Suitable assays to monitor dimerization of ALK-2/BMPR-2 are commercially available and rely on the same principle as the ALK-1/BMPR-2 assays described herein.

In a particularly preferred embodiment, there is provided a BsAB, wherein said BsAB comprises two binding domains, wherein the first binding domain is specific for ALK-1 and the second binding domain is specific for BMPR-2, and wherein said BsAB has agonistic activity with respect to ALK-1/BMPR-2 signaling, and wherein the BsAB does not induce dimerization of ALK-2/BMPR-2.

In a particularly preferred embodiment, the BsAB according to the first, second or third aspect binds ALK-2 or an antigen according to SEQ ID 117 with an affinity that is lower or equal to the binding affinity of the BsAB for BSA.

In a particularly preferred embodiment, the BsAB comprises two binding domains, wherein the first binding domain is specific for ALK-1 and the second binding domain is specific for BMPR-2, and wherein said BsAB promotes dimerization of ALK-1/BMPR-2, and wherein the BsAB binds ALK-2 or an antigen according to SEQ ID 117 with an affinity that is lower or equal to the binding affinity of the BsAB for BSA.

In a particularly preferred embodiment, there is provided a BsAB, wherein said BsAB comprises two binding domains, wherein the first binding domain is specific for ALK-1 and the second binding domain is specific for BMPR-2, and wherein said BsAB promotes dimerization of ALK-1/BMPR-2, and wherein the BsAB does not promote dimerization of ALK-2/BMPR-2.

In a particularly preferred embodiment, there is provided a BsAB, wherein said BsAB comprises two binding domains, wherein the first binding domain is specific for ALK-1 and the second binding domain is specific for BMPR-2, and wherein said BsAB has agonistic activity with respect to ALK-1/BMPR-2 signaling, and wherein an effective dose of the BsAB has a lower osteogenic activity than an effective dose of rhBMP-9, or has no osteogenic activity. Determination of agonistic activity with respect to ALK-1/BMPR-2 signaling can occur by any method specified herein. Determination of osteogenic activity can occur by any method specified herein, and preferably occurs using the C2C12 method.

BsAB with agonistic activity for ALK-1/BMPR-2 signaling but with lower osteogenic activity than rhBMP-9 or without osteogenic activity are likely to revert endothelial dysfunction, decrease right ventricular systolic blood pressure (RVSP), and/or revert PAH.

Bone morphogenic proteins (BMPs) are known to promote osteogenesis. Whereas human BMP-9, BMP-9 variants and designer BMP-9s, such as mutated BMP-9 versions are likely to induce osteogenic activities via ALK-2 signaling, this is different for BsABs targeting only and specifically the ALK-1/BMPR-2 receptor complex. Due to their genuine specificity for ALK-1 (and BMPR-2), induction of signaling via ALK-2 is unlikely for antibodies according to the current invention, and can furthermore be excluded by specific assays (e.g. example 11, example 12).

The potential osteogenic activity of BsAbs may be assessed using any method specific for assessing the osteogenic activity of wild type BMPs. BMPs promote the growth and differentiation of a number of cell types. Differentiation may be monitored using, for example, luminescence reporters for alkaline phosphatase or calorimetric reagents such as Alcian Blue or PNPP (Asahina et al. (1996) Exp. Cell Res, 222:38-47; lnada et al. (1996) Biochem. Biophvs. Res. Commun. 222:317-322; Jortikka et al. (1998) Life ScL 62:2359-2368; Cheng et al. (2003) J. Bone Joint Surgery 95A:1544-1552).

A mouse myoblast cell line such as C2C12 (ATCC, catalogue number CRL-1772) is a preferred option for evaluation of osteogenic activity of BsABs showing agonistic activity with respect to ALK-1/BMPR-2 signaling. The C2C12 cell line differentiates rapidly, forming contractile myotubes and producing characteristic muscle proteins. Treatment with BMPs causes a shift in the differentiation pathway from myoblastic to osteoblastic. Alkaline phosphatase (ALP) activity in C2C12 cells can be used as a marker of the osteoblastic activity. As described in the examples, an Alkaline Phosphatase Assay Kit can be used for read-out of ALP activity. Multiple Alkaline Phosphatase Assay Kits are commercially available.

In a preferred embodiment according to the third aspect, the BsAB according to the first aspect is characterized in that C2C12 cells treated with the EC50 of rhBMP-9 have a higher alkaline phosphatase (ALP) activity than C2C12 cells treated with the same concentration of BsAB. In the particular context the EC50 is the EC50 for agonistic activity as determined from an ALK-1/BMPR-2 dimerization assay (FIG. 8).

In a preferred embodiment according to the third aspect, the BsAB according to the second aspect is characterized in that C2C12 cells treated with the EC50 of rhBMP-9 have a higher alkaline phosphatase (ALP) activity than C2C12 cells treated with the same concentration of the BsAB.

In a preferred embodiment according to the third aspect, the BsAB according to the first or second aspect is characterized in that C2C12 cells treated with the EC50 of rhBMP-9 have a higher alkaline phosphatase (ALP) activity than C2C12 cells treated with the EC50 of BsAB.

A BsAB according to the current invention is considered to have a lower osteogenic activity than rhBMP-9, if C2C12 cells treated with the EC50 of rhBMP-9 have a higher alkaline phosphatase (ALP) activity than C2C12 cells treated with the same concentration of BsAB. The EC50 of rhBMP-9 (for agonistic activity) is determined by titration as known in the art.

A BsAB according to the current invention is considered to have a lower osteogenic activity than rhBMP-9, if C2C12 cells treated with an EC50 of rhBMP-9 have a higher alkaline phosphatase (ALP) activity than C2C12 cells treated with an EC50 of BsAB.

In a preferred embodiment according to the third aspect, a BsAB according to the first aspect or a BsAB according to the second aspect has no osteogenic activity in C2C12 cells.

A BsAB according to the current invention is considered to have no osteogenic activity in C2C12 cells, if treatment of C2C12 cells with the BsAB, e.g. with an effective dose or the EC50 of the BsAB, does not lead to a higher alkaline phosphatase (ALP) activity than for C2C12 cells treated with a vehicle control.

Further methods for assessing osteogenic activity in vitro or in vivo are known in the art. However, for the sake of clarity, whenever a BsAB is considered to have a lower osteogenic activity than rhBMP-9 based on the C2C12 assay, this result prevails.

The rat limb bud cartilage differentiation assay may also be used to monitor activity in primary cells. In alternative embodiments, reporter gene or kinase assays may be used. Since BMPs activate JAK-STAT signaling, a BMP responsive cell line containing a STAT-responsive reporter such as GFP or luciferase may be used (Kusanagi et al. (2000) Mol Biol. Cell., 11:555-565). For example, BMP activity in kidney cells may be determined using cell-based assays; see e.g. Wang and Hirschberg (2004) J. Biol. Chem. 279:23200-23206. Osteogenic activity may also be measured in vivo, via rat ectopic bone assays or mammalian bone growth models. In some embodiments, osteogenic activity is measured in non-human primate models. These models are described in Isaacs et al., Mol. Endocrinol. 24:1469-1477 (2010). Methods for evaluating bone mass and quality are known in the art and comprise X-ray diffraction: DXA: DEQCT; pQCT, chemical analysis, density fractionation, histophotometry, histomorphometry, and histochemical analysis as described, for example, in Lane et al. J Bone Min. Res. 18:2105-2115 (2003). One assay for determining cortical bone density is the MicroCT assay. Following pQCT measurement, the microCT evaluation can be performed, for example, using a Scanco mCT40 (Scanco Medical AG) on a femur.

According to a fourth aspect, there is provided a BsAB according to the first, second or third aspect for use as a medicament.

In some embodiments the use as a medicament comprises increasing or rescuing the ALK-1/BMPR-2 signaling in at least one target cell of a subject. In some embodiments, the at least one target cell is an endothelial cell, such as a lung endothelial cell. In some embodiments, the subject is a human or a mammal. In some embodiments the use as a medicament comprises modulation of ALK-1/BMPR-2 signaling by administration of an effective dose of a BsAB according to the invention to a human subject in need thereof. In some embodiments the use as a medicament comprises modulation of ALK-1/BMPR-2 signaling by administration of an effective dose of a BsAB according to the invention to a subject in need thereof, wherein the BsAB induces no osteogenic activity and/or a lower osteogenic activity than an equal dose or the EC50 of rhBMP-9. In some embodiments, the use as a medicament comprises administering to a subject in need thereof a pharmaceutical composition comprising an effective dose of a BsAB according to the current invention. In certain embodiments according to the fourth aspect, the use as a medicament further comprises administering at least one additional therapeutic agent appropriate for effecting combination therapy, e.g., an agent for decreasing the blood pressure by relaxation of the pulmonary arteries, such as a Ca antagonists, an ET antagonists, a PDE V inhibitor or an sGC stimulator.

According to a fifth aspect, there is provided a BsAB according to the first, second or third aspect for use in the treatment of vascular disease or pulmonary hypertension.

In some embodiments the use in the treatment of vascular disease or pulmonary hypertension comprises increasing or rescuing the ALK-1/BMPR-2 signaling in at least one target cell of a subject. In some embodiments, the at least one target cell is an endothelial cell, such as a lung endothelial cell. In some embodiments, the subject is a mammal. In some preferred embodiments, the subject is a human patient. In some embodiments, the use in the treatment of vascular disease or pulmonary hypertension comprises modulation of ALK-1/BMPR-2 signaling by administration of an effective dose of a BsAB according to the invention to a subject in need thereof. In some embodiments, the use in the treatment of vascular disease or pulmonary hypertension comprises modulation of ALK-1/BMPR-2 signaling by administration of an effective dose of a BsAB according to the invention to a subject in need thereof, wherein the BsAB induces no osteogenic activity and/or a lower osteogenic activity than an equal dose of rhBMP-9. In some embodiments, the use in the treatment of vascular disease or pulmonary hypertension comprises administering to a subject in need thereof a pharmaceutical composition comprising an effective dose of a BsAB according to the current invention.

In some embodiments, the PH is pulmonary arterial hypertension (PAH). In some embodiments the PAH is Group 1 PAH. The Group 1 PAH may for example be or include idiopathic or primary pulmonary hypertension. In some embodiments, the PH is an idiopathic pulmonary arterial hypertension (IPAH). The Group 1 PAH may in some embodiments also be or involve familial hypertension. In some embodiments the Group 1 PAH may include or may be pulmonary hypertension secondary to chronic hypoxia. In some embodiments the Group 1 PAH may include or may be pulmonary hypertension secondary to, but not limited to, connective tissue disease, congenital heart defects (shunts), pulmonary fibrosis, portal hypertension, HIV infection, sickle cell disease, a drug and/or a toxin (e.g., anorexigens, cocaine chronic pulmonary obstructive disease, sleep apnea, and schistosomiasis. In some embodiments the Group 1 PAH may include or may be pulmonary hypertension associated with significant venous or capillary involvement (pulmonary veno-occlusive disease, pulmonary capillary hemangiomatosis). In some embodiments the Group 1 PAH may include or may be pulmonary hypertension associated with secondary pulmonary hypertension that is out of proportion to the degree of left ventricular dysfunction. In some embodiments the Group 1 PAH may include or may be persistent pulmonary hypertension in a newborn baby. In some embodiments the subject is human. In some embodiment the subject is a mammal.

According to a sixth aspect, there is provided a method to test the suitability of a BsAB for use in the therapy, e.g. of pulmonary hypertension, comprising the step of (i) evaluating the agonistic activity of the BsAB for ALK-1/BMPR-2 signaling.

In some embodiments according to the sixth aspect said method is a method to test the suitability of a BsAB for use in the therapy, e.g. of pulmonary hypertension, comprising the steps of (i) evaluating the agonistic activity of the BsAB for ALK-1/BMPR-2 signaling, and/or (ii) evaluating the osteogenic activity of the BsAB.

In some embodiments according to the sixth aspect, the therapy is the therapy of a disease characterized by dysfunctional ALK-1/BMPR-2 signaling, e.g. pulmonary hypertension.

In some embodiments according to the sixth aspect, evaluating the agonistic activity of the BsAB for ALK-1/BMPR-2 signaling occurs by one of the suitable methods described herein.

In some preferred embodiments according to the sixth aspect, evaluating the agonistic activity of the BsAB for ALK-1/BMPR-2 signaling occurs by analyzing the ability of the BsAB to promote dimerization of ALK-1 and BMPR-2. In some of these preferred embodiments according to the sixth aspect, evaluating the agonistic activity of the BsAB for ALK-1/BMPR-2 signaling occurs by using the U2OS ACVRL1/BMPR-2 Dimerization Cell Line.

In a preferred embodiment according to the sixth aspect, there is provided a method comprising (i) analyzing the ability of the BsAB to promote dimerization of ALK-1 and BMPR-2, and (ii) optionally comparing the binding affinities of the BsAB for ALK-2 and BSA and (iii) selecting the BsAB as suitable, where the BsAB at least promotes dimerization as determined according to step (i) and optionally binds ALK-2 with an affinity that is lower or equal to the BsABs affinity for BSA, as determined according to step (ii).

In a preferred embodiment according to the sixth aspect, there is provided a method comprising (i) analyzing the ability of the BsAB to promote dimerization of ALK-1 and BMPR-2, and (ii) optionally analyzing the ability of the BsAB to promote dimerization of ALK-2 and BMPR-2 and (iii) selecting the BsAB as suitable, where the BsAB at least promotes dimerization of ALK-1 and BMPR-2 as determined according to step (i) and optionally does not promote dimerization of ALK-2 and BMPR-2 as determined according to step (ii).

In a preferred embodiment according to the sixth aspect, there is provided a method comprising (i) analyzing the ability of the BsAB to promote dimerization of ALK-1 and BMPR-2, and (ii) optionally comparing the osteogenic activity of an effective dose of the BsAB with the osteogenic activity of an effective dose of BMP-9 and (iii) selecting the BsAB as suitable, where the BsAB at least promotes dimerization of ALK-1 and BMPR-2 as determined according to step (i) and optionally shows less osteogenic activity than an effective dose of BMP-9 as determined according to step (ii).

A BsAB is considered suitable for use in the therapy, e.g. of pulmonary hypertension, if an EC50 can be determined for the BsAB by using the PathHunter U2OS ALK-1/BMPR-2 dimerization assay. However, even if no EC50 can be determined by the PathHunter U2OS ALK-1/BMPR-2 dimerization assay, a BsAB according to the current invention may still be suitable, if an alternative method described herein to assay agonistic activity for ALK-1/BMPR-2 signaling shows significant agonistic activity for the BsAB. A BsAB is considered particularly suitable for use in the therapy, e.g. of pulmonary hypertension, if the EC50 of the bispecific antibody according to the current invention is higher than or equal to the EC50 of BMP-9, for the U2OS ACVRL1/BMPR-2 Dimerization assay.

In another preferred embodiment according to the sixth aspect, evaluating the agonistic activity of the BsAB for ALK-1/BMPR-2 signaling occurs by an assay on SMAD1/SMAD5 phosphorylation, as described for the second aspect of the current invention.

A BsAB or compound is considered suitable for use in the therapy, e.g. of pulmonary hypertension, if an effective dose of said antibody or compound induces phosphorylation of SMAD1 and/or SMAD5. For example, effective doses of rhBMP-9 for phosphorylation of SMAD5 are 1 ng/ml and 10 ng/ml (see FIG. 2).

A BsAB or compound is considered particularly suitable for use in the therapy, e.g. of pulmonary hypertension, if an effective dose of the BsABs leads to an induction of SMAD1 and/or SMAD5 phosphorylation in an endothelial cell line which is comparable to the induction occurring upon treatment with an effective dose of rhBMP-9. Of note, required concentrations for BsAB and BMP-9 may strongly deviate from each other.

In another preferred embodiment, according to the sixth aspect, evaluating the agonistic activity of the BsAB for ALK-1/BMPR-2 signaling occurs by analyzing the anti-apoptotic activity of the BsAB using primary endothelial cells, such as HPAEC, HAoEC, HCAEC or HMVEC-L cells as described in example 6.

A BsAB or compound is considered suitable for use in the therapy, e.g. of pulmonary hypertension, if an effective dose of said BsAB reduces the apoptotic index for endothelial cells. In some embodiments, the endothelial cells are selected from the list comprising HPAEC, HAoEC, HCAEC and HMVEC-L cells.

A BsAB leading to a decrease of the apoptotic index (caspase 3/7 activity per live cell) in at least one endothelial cell line is considered suitable for use in the therapy of pulmonary hypertension.

BsABs according to the current invention leading to a decrease of the apoptotic index (caspase 3/7 activity per live cell) in at least one endothelial cell line, where the decrease is comparable to the decrease induced by treatment with BMP-9 are considered suitable for use in the therapy of pulmonary hypertension.

In another preferred embodiment, according to the sixth aspect, evaluating the agonistic activity of the BsAB for ALK-1/BMPR-2 signaling occurs by using an assay for analyzing the preservation of endothelial barrier function in vitro or in vivo.

In some embodiments, evaluating the agonistic activity of the BsAB for ALK-1/BMPR-2 signaling occurs by an assay as described in example 7. In some embodiments, evaluating the agonistic activity of the BsAB for ALK-1/BMPR-2 signaling occurs by evaluation of the endothelial barrier function in a mouse model for sepsis as described in example 8. In some embodiments, evaluating the agonistic activity of the BsAB for ALK-1/BMPR-2 signaling occurs using a Monocrotaline-induced pulmonary hypertension rat model as described in example 9. In some embodiments, evaluating the agonistic activity of the BsAB for ALK-1/BMPR-2 signaling occurs using a Sugen/Hypoxia-induced pulmonary hypertension rat model as described in example 10.

A BsAB or is considered suitable for use in the therapy of pulmonary hypertension, if the BsAB is considered to have agonistic activity for ALK-1/BMPR-2 signaling based on any of the aforementioned assays.

In a preferred embodiment according to the sixth aspect, evaluating the osteogenic activity of the BsAB occurs by any one of the methods described herein.

In a preferred embodiment according to the sixth aspect, evaluating the osteogenic activity of the BsAB occurs by using the C2C12 assay.

A BsAB is considered to be not suitable for use in the therapy, e.g. of pulmonary hypertension, if C2C12 cells treated with a defined concentration of BsAB have a higher alkaline phosphatase (ALP) activity than C2C12 cells treated with the same concentration of rhBMP-9, wherein said defined concentration is the EC50 of rhBMP-9.

A BsAB is considered to be suitable for use in the therapy, e.g. of pulmonary hypertension, if the BsAB is characterized in that C2C12 cells treated with the EC50 of rhBMP-9 have a higher alkaline phosphatase (ALP) activity than C2C12 cells treated with the same concentration of the BsAB.

According to a seventh aspect, there is provided a pharmaceutical composition comprising a BsAB according to any one of the aspects 1, 2, 3, 4 or 5 and a pharmaceutically acceptable carrier. The pharmaceutical composition may also contain one or more further therapeutic, including prophylactic, ingredients. The carrier(s) must be "acceptable" in the sense of being compatible with the other ingredients of the formulation and not deleterious to the recipient thereof. In one embodiment according to the seventh aspect the one or more further therapeutic, including prophylactic, ingredients is at least one agent decreasing blood pressure by relaxation of the pulmonary arteries.

EXAMPLES

Example 1 Identification of Binders for BMPR-2 and ALK 1: Antibody Generation from BioInvent Antibody Libraries Fully human antibody phage display libraries (BioInvent n-CoDeR Fab lambda and scFv lambda libraries) were used to isolate human monoclonal antibodies of the present invention by selection against soluble biotinylated antigen. The following protocol was applied to both libraries. Streptavidin-coupled Dynabeads M-280 (Invitrogen™) were coated for one hour at room temperature (RT) with the biotinylated antigen (1 tube) and the biotinylated off-target (3 tubes), respectively. Dynabeads were washed and subsequently blocked for 1 h at RT with end-over-end rotation. For depletion of off-target binders the blocked phage library was added to the blocked off-target loaded Dynabeads and incubated for 10 min at room temperature with end-over-end rotation. This depletion step was repeated 2 times. The depleted phage library was added to the blocked target loaded Dynabeads and incubated for 60 min at RT with end-over-end rotation. After stringent washing (3× in blocking buffer and 9× in PBS (150 mM NaCl; 8 mM Na2HPO4; 1.5 mM KH2PO4; adjusted to pH=7.4-7.6) with 0.05% Tween-20). Dynabeads with Fab-phages binding specifically to the coated target were directly used to infect *Escherichia coli* strain HB101. Subsequently the phages were amplified in *Escherichia coli* strain HB101 using M13KO7 Helper Phage (Invitrogen™). In the following selection rounds the target concentration was decreased to augment the selection pressure for high affinity binders. For a first qualitative assessment, for each clone pool monoclonal cultivation and expression of 88 randomly picked Fab-phage clones was performed and subsequently tested for binding to the respective target previously used for panning. For the specific example, a "binder" is a Fab-phage molecule showing in the ELISA assay at least a signal intensity of the average signal intensity of non-binding control Fab-phage molecules plus 10 times the standard deviation (average+ 10× standard deviation of non-target binding Fab-phage). In a next step, VH and VL of 39744 and 38272 clones originating from ALK-1 and BMPR-2 panning clone pools were sequenced, respectively. Clones having undesired sequence features and stop codons, were removed. 4483 and 1059 VH/VL combinations having distinct amino acid sequences were found for ALK-1 and BMPR-2 panning pools originating clones, respectively. For each VH/VL distinct sequence combination, up to four representative clones were selected and investigated in Enzyme Linked Immunosorbent Assay (ELISA). For clones originating from ALK-1 panning clone pools, binding was measured to the targets, human ALK-1 and mouse ALK-1, and to the off-target human ROR1-Fc (SEQ ID NO 113). For clones originating from BMPR-2 panning clone pools, binding was measured to the target human BMPR-2 and to the off-target human ROR1-Fc. For that purpose Streptavidin-coated 384-well plates were first coated with the respective protein. Subsequently the plates were washed and incubated with soluble scFv, soluble Fab, or Fab-on-Phage comprising supernatants from *Escherichia coli* (*E. coli*) cultures transformed to express the antibody fragment to be screened. Unbound antibody fragments were subsequently removed by washing. Next, the plate-bound antibody fragments were detected using horseradish-peroxidase labelled secondary antibody for detection. 200 clones having a distinct VH/VL amino acid sequence combination, and binding specifically to human and mouse ALK-1 were identified. 388 clones having a distinct VH/VL amino acid sequence combination, and binding specifically to human BMPR-2 were identified.

Example 2 Evaluation of Receptor Binding Activity/Biochemical Characteristics of the Antibodies The receptor binding activity may be assessed using any methods suitable for assessing the activity of wild type BMPs. The affinity of a BsAb for one or more BMP receptors can be determined by receptor binding assays. For example, affinities for ALK-2, ALK-3, ALK-6, ActR11, ActR11b, or BMPR11 can be determined. Suitable binding assays include, but are not limited to ELISA, fluorescence anisotropy and intensity, scintillation proximity assays (SPA), Biacore (Pearce et al., Biochemistry 38:81-89 (1999)), DELFIA assays, and AlphaScreen™ (PerkinElmer; Bosse R., Illy C, and Chelsky D (2002)).

For example, Biacore or surface plasmon resonance (SPR) assays are used (McDonnell, Gurr. Opin. Chem. Biol. 5:572-577 (2001). Fluorescence assays can be easily developed by labeling either receptor or BsAb with a fluorescent dye. Additionally, scintillation proximity assays (SPA) can be used to determine receptor binding affinity.

SPR experiments for quantitative binding analyses were performed using a Biacore T200 instrument (GE Healthcare Biacore, Inc.) equipped with Series S Sensor Chips CM5 (GE Healthcare Biacore, Inc.). Binding assays were carried out at 25° C. with assay buffer HBS-EP+(10 mM HEPES pH 7.4, 150 mM NaCl, 3 mM EDTA, 0.05% Surfactant P20). Antigens were covalently immobilized to the chip surface via amine coupling chemistry. The same proteins that had previously been used to isolate the antibodies of the invention during panning and screening [murine ALK-1-Fc SEQ ID NO: 114, human ALK-1-Fc SEQ ID NO: 116, as well as BMPR-2-Fc SEQ ID NO: 115 (human and murine extracellular are identical)] were used here as analytes to determine $K_D$ values. Reagents for amine coupling (1-ethyl-3-(3-dimethylaminopropyl) carbodiimide hydrochloride (EDC), N-hydroxysuccinimide (NHS), ethanolamine-HCl pH 8.5) were used from the Amine Coupling Kit (GE Healthcare, product code BR-1000-50). The sensor chip surface was activated with a freshly prepared solution of 0.2 M EDC and 0.05 M NHS passed over the chip surface for 420 seconds at a flow rate of 10 µl/min, followed by an injection of antigen (dissolved to 0.5 µg/ml in immobilization buffer, 10 mM sodium acetate pH 5.0) with a target level of 50 RU. Excess of activated groups were blocked with a 1 molar solution of ethanolamine injected at a flow rate of 10 µl/min for 420 seconds.

To determine kinetics and affinity a concentration series from 1.56 nM to 200 nM of the antibodies was injected over the immobilized antigens at a flow rate of 30 µl/min for 180 seconds and the dissociation was monitored for 10 minutes. The sensor surface was regenerated for 20 seconds with regeneration solution (glycine-HCl pH 1.5) after each assay cycle consisting of a single analyte injection.

Obtained sensorgrams were double-referenced, (reference cell correction followed by buffer sample subtraction). $K_D$ values were calculated based on the ratio of dissociation ($k_d$) and association ($k_a$) rate constants which were obtained by globally fitting sensorgrams with a first order 1:1 Langmuir binding model, implemented in the Biacore Evaluation Software Package (Biacore T200 Evaluation Software Version 2.0, GE Healthcare Biacore, Inc.).

Two BMPR2 and two murine and human Alk1 x-reactive binders are given as examples in table 1.

TABLE 1

Affinities of BMPR-2 and ALK-1 specific antibodies

| Antibody | Target | $K_D$ [M] | SEQ ID |
|---|---|---|---|
| TPP-13660 | Human ALK-1 | $8.5 \times 10^{-9}$ | 97, 98 |
| | Murine ALK-1 | $2.5 \times 10^{-8}$ | 97, 98 |
| TPP-13654 | Human ALK-1 | $8.6 \times 10^{-9}$ | 83, 84 |
| | Murine ALK-1 | $2.5 \times 10^{-8}$ | 83, 84 |
| TPP-13667 | BMPR-2 | $8.8 \times 10^{-9}$ | 111, 112 |
| TPP-13469 | BMPR-2 | $6.2 \times 10^{-9}$ | 69, 70 |

Example 3: Construction and Expression of BsAbs in scFv-Fc (Kih) Format

Figure 7:
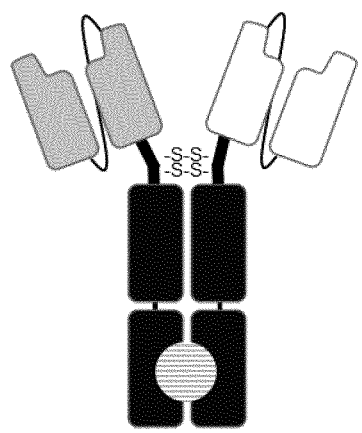
FIG. 7 is a schematic representation of a scFv-Fc (kih) construct combining two mono-specific antibody scFv fragments linked to heterodimeric human IgG Fc. White: scFv specific to BMPR-2, grey: scFv specific to ALK-1, black: human IgG Fc domains with knob-into-hole mutations, represented by shaded circle.

In a first step all binders obtained from the BioInvent n-CoDeR Fab lambda and scFv lambda libraries against the targets BMPR-2 and ALK-1 were transferred to one compatible scFv format by using standard recombinant DNA techniques (Sambrook, J. et al. eds., MOLECULAR CLONING: A LABORATORY MANUAL (2d Ed. 1989) Cold Spring Harbor Laboratory Press, NY. Vols. 1-3). The VH sequences were linked by a 15 amino acid $(GGGGS)_3$ linker to the VL sequence of the respective binding binders. All resulting scFv binding domains to ALK-1 were then fused to an human IgG Fc domain containing the knob mutation, whereas all BMPR-2 scFv binding domains were fused to a human IgG2 Fc domain containing the hole mutations. The scFv binding domains are linked via the sequence GG GGSGGGGSGG GGSG to the respective Fc hetero-dimerization domains (FIG. 7). The constructs binding ALK-1 scFv-linker-Fc (knob) and scFv-linker-Fc (hole) were both cloned into the vector pTT5 for expression in HEK293E cells. By combining each ALK-1 specific knob construct with each BMPR-2 specific hole construct, a combinatorial set of BsAbs binding to ALK-1 and BMPR-2 was generated, that was then screened for a potential agonistic pair.

Example 4 Evaluation of Agonistic Activity

Agonistic Activity of BsABs in Recombinant Cells Expressing ALK 1 and BMPR-2

In order to test the molecules of the invention for potential agonistic activity, the PathHunter U2OS ALK 1/BMPR-2 dimerization cell obtained from DiscoverX Corporation (catalogue number 93-0962C3) was used. All products necessary for cell seeding, culturing of cells, cell culture media, and stimulation media were obtained from DiscoverX Corporation. Handling of cells and testing of molecules for potential agonistic activity was performed according to the manufacturer's instructions. Molecules leading to an increase in signal intensity, e.g. comparable to the natural ligand BMP-9 strongly promote dimerization of ALK-1/BMPR-2. Those molecules leading to an increase in signal intensity, e.g. comparable to the natural ligand BMP-9 are considered as BsABs with potent agonistic effect on ALK-1/BMPR-2 signaling. From the 1240 screened bispecifics 36 molecules lead to an increase in signal intensity and were considered as BsABs with potent agonistic effect on ALK-1/BMPR-2 signaling. In FIG. 8 the results for the agonistic BsABs TPP-14669 and TPP-14719 are shown with an overview of the molecule composition in table 2.

TABLE 2

Molecule composition of BsAB TPP-14669 and TPP-14719

| Bispecific Antibody | Agonistic activity in PathHunter U2OS cells $EC_{50}$ [nM] | ALK-1 binding entity | BMPR-2 binding entity | Bispecific Antibody SEQ ID |
|---|---|---|---|---|
| TPP-14696 | 6.3 | TPP-13654 | TPP-13667 | 1, 8, 15, 22 |
| TPP-14719 | 6.9 | TPP-13660 | TPP-13469 | 29, 36, 43, 50 |

Example 5 Evaluation of Agonistic Activity

Determination of BsABs Agonistic Activity Using Primary Endothelial Cells

Primary human endothelial cells used for testing bsAbs agonistic activity are either obtained from PromoCell GmbH or from Lonza (Verviers, Belgium). PromoCell GmbH: Human Pulmonary Artery Endothelial Cells (HPAEC) (catalogue number C-12241); Human Umbilical Vein Endothelial Cells (HUVEC) (catalogue number C-12203); Human Aortic Endothelial Cells (HAoEC) (catalogue number C-12271); Human Coronary Artery Endothelial Cells (HCAEC) (catalogue number C-12221); Lonza (Verviers, Belgium): Human Pulmonary Artery Endothelial Cells (catalogue number HPAEC) (CC-2530); Human lung microvascular endothelial cells (HMVEC-L) (catalogue number CC-2527).

Figure 2:
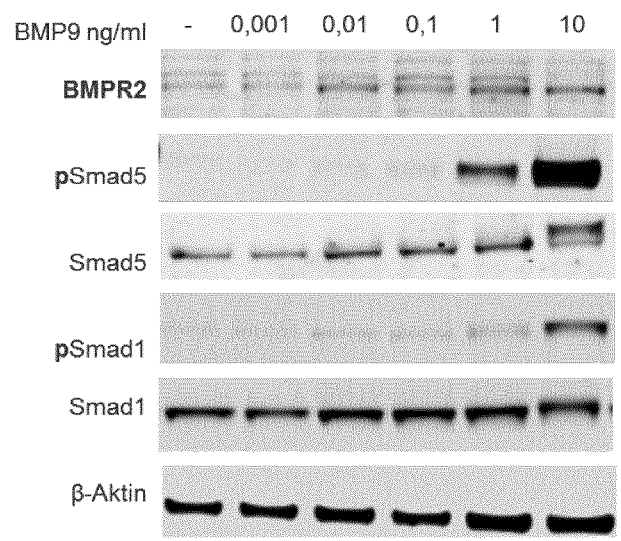
FIG. 2 illustrates recombinant human BMP-9 (rhBMP-9) induced SMAD1 and/or 5 phosphorylation (pSmad1 and pSmad5, respectively) in cultured human pulmonary endothelial cells (HPAEC) in vitro. Indicated concentrations of BMP-9 were added to the cell culture medium 2 hours before the cell lysis and subsequent western blot analysis. Beta-Actin staining served as loading control.

All tests are performed using recombinant human BMP-9 as a reference, since BMP-9 is the natural activator of ALK-1/BMPR-2 signaling. Using the following description of the method, BMP-9 showed phosphorylation of Smadl/5 in HPAEC, the type of endothelial cells involved in the pathogenesis of pulmonary arterial hypertension (FIG. 2).

Cells are cultivated following the manufacturer's instructions. All media and reagents are either obtained from Promocell or Lonza. For analyzing BsABs agonistic activity, cells are seeded in 6 well microtiter plates. After one day of growing, mediums are exchanged by starvation medium containing 0.1% of fetal calf serum and cells are cultured for another 24 hours. Following this, cells are incubated with various concentrations of BMP-9 as well as with various concentrations of BsABs for 2 to 4 hours. For preparation of protein lysates, cells are lysed in 1×RIPA buffer (10×RIPA Buffer, Abcam, catalogue number ab156034) containing 1× Halt Protease and Phosphatase Inhibitor Cocktail (100× Halt Protease and Phosphatase Inhibitor Cocktail, Thermo Scientific, catalogue number 78440). Preparation of crude protein extracts are performed following the manufacturer's protocol. Protein samples are separated by Sodium dodecyl sulfate polyacrylamide gel electrophoresis (SDS PAGE), separated proteins are transferred onto Nitrocellulose membranes and the phosphorylation status of BMP-9 dependent signal transduction molecules SMAD-1 and SMAD-5 are analyzed by using specific anti-phospho SMAD-1 and anti-phospho SMAD-5 antibodies (NEB, Smad 1/5/9 Antibody Sampler Kit, catalogue number 12656T). Those molecules leading to an induction of SMAD1 or SMAD5 phosphorylation in endothelial cells comparable to the natural ligand BMP-9 are considered as BsABs with potent agonistic effect on ALK-1/BMPR-2 signaling.

Example 6 Evaluation of Agonistic Activity

Determination of BsABs Anti-Apoptotic Activity Using Primary Endothelial Cells

Primary human endothelial cells used for testing BsABs agonistic activity are either obtained from PromoCell GmbH or from Lonza (Verviers, Belgium). PromoCell GmbH: Human Pulmonary Artery Endothelial Cells (HPAEC) (catalogue number C-12241); Human Umbilical Vein Endothelial Cells (HUVEC) (catalogue number C-12203); Human Aortic Endothelial Cells (HAoEC) (catalogue number C-12271); Human Coronary Artery Endothelial Cells (HCAEC) (catalogue number C-12221); Lonza (Verviers, Belgium): Human Pulmonary Artery Endothelial Cells (catalogue number HPAEC) (CC-2530); Human lung microvascular endothelial cells (HMVEC-L) (catalogue number CC-2527).

Figure 3:
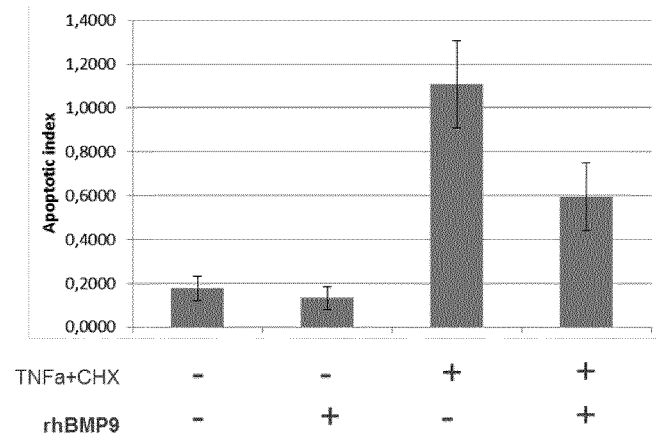
FIG. 3 illustrates the reduction of apoptosis in human pulmonary endothelial cells (HPAEC) in vitro after treatment with recombinant human BMP-9 (rhBMP-9). HPAEC were incubated for 16 h with 5 ng/ml rhBMP-9. 10 ng/ml TNFα and 20 µg/ml cycloheximide (CHX) were added 4 h before determining cell apoptosis using the ApoOne/CTB assay (Promega) according to the manufacturer's instructions.

Generally, all tests are performed using BMP-9 as a reference, since BMP-9 is the natural activator of ALK-1/BMPR-2 signaling. Using the following description of the method, BMP-9 reduced the apoptotic index in HPAEC (FIG. 3).

Cells are cultivated following the manufacturer's instructions. All media and reagents are either obtained from PromoCell or Lonza. For analyzing BsABs agonistic activity, after one day of growing, mediums are exchanged by starvation medium containing 0.1% of fetal calf serum and cells are cultured for another 24 hours. Following this, cells are incubated with various concentrations of BMP-9 as well as with various concentrations of BsABs overnight. Finally, the apoptotic index of the endothelial cells is determined using the ApoOne/CTB assay (Promega) according to the manufacturer's instructions. Those molecules leading to a decrease of the apoptotic index (caspase 3/7 activity per live cell) in endothelial cells comparable to the natural ligand BMP-9 are considered as BsABs with potent agonistic effect on ALK-1/BMPR-2 signaling. For example cells can also be incubated with TNFα and cycloheximide (CHX) for 4 hours to induce apoptosis and to determine whether the effect can be rescued by addition of an effective dose of BsAB.

Example 7 Evaluation of Agonistic Activity

Determination of Preservation of Endothelial Barrier Function In Vitro

Primary human endothelial cells used for testing BsABs agonistic activity are either obtained from PromoCell GmbH or from Lonza (Verviers, Belgium). PromoCell GmbH: Human Pulmonary Artery Endothelial Cells (HPAEC) (catalogue number C-12241); Human Umbilical Vein Endothelial Cells (HUVEC) (catalogue number C-12203); Human Aortic Endothelial Cells (HAoEC) (catalogue number C-12271); Human Coronary Artery Endothelial Cells (HCAEC) (catalogue number C-12221); Lonza (Verviers, Belgium): Human Pulmonary Artery Endothelial Cells (catalogue number HPAEC) (CC-2530); Human lung microvascular endothelial cells (HMVEC-L) (catalogue number CC-2527).

As described previously, all tests are performed using BMP-9 as a reference, since BMP-9 is the natural activator of ALK-1/BMPR-2 signaling. The following description of the method revealed, while either LPS (Lipopolysaccharides) (FIG. 4) or thrombin (FIG. 5) decreased the electrical resistance (measures the endothelial barrier function) of HPAEC (Lonza), BMP-9 preserved the endothelial barrier function.

Cells are cultivated following the manufacturer's instructions. All media and reagents are either obtained from Promocell or Lonza. Endothelial cells are seeded on 1% gelatine-coated biochips containing gold microelectrodes (e.g. ECIS 8W10E+). On the second day after seeding, cells are serum-starved for 1 h in the presence of vehicle, BMP-9, or BsABs. Electrical resistance is then measured at 4000 Hz frequency using electric cell-substrate impedance sensing system (e.g. ECIS, Applied Biophysics, Troy, N.Y., USA). After 1 h measuring the baseline electrical resistance in the presence of vehicle (veh), BMP-9, or BsABs, LPS, thrombin or other substances enhancing the endothelial permeability, respectively impairing the barrier function of the endothelial cell layer are added to the cell medium. The effect of BsABS on the endothelial barrier function is compared to vehicle and BMP-9. BsABs preserving the endothelial electrical resistance of endothelial monolayers, and thus the endothelial barrier function in a BMP 9-like manner are considered as BsABs with potent agonistic effect on ALK-1/BMPR-2 signaling.

Example 8 Evaluation of Agonistic Activity

Determination of the Endothelial Barrier Function in a Mouse Model for Sepsis

Figure 6:
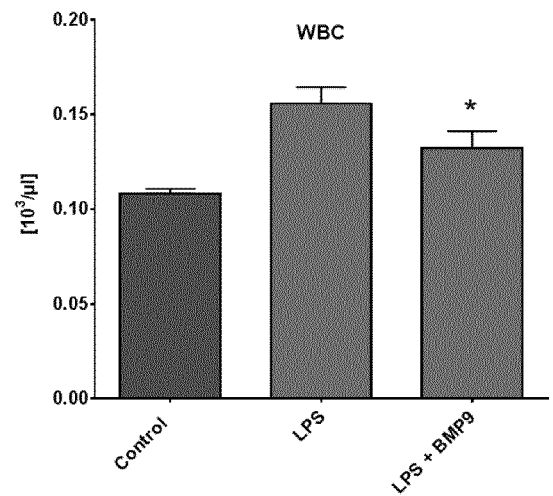
FIG. 6 illustrates the effect of BMP-9 on the number of white blood cells (WBC) in the broncho-alveolar lavage fluid (BALF) of a mouse model for sepsis. The broncho-alveolar lavage was performed 48 h after a single intraperitoneal injection of 5 mg/kg LPS. The treatment with daily 100 ng/animal BMP-9 started 1 h prior to the LPS injection (LPS+BMP-9). The animals which received LPS but no treatment with BMP-9 (LPS) received daily intraperitoneal injections of vehicle (PBS) starting 1 h prior to the LPS application. Control animals (Control) received neither LPS, nor BMP-9, nor vehicle. *: p<0.05; vs. LPS (One-way Anova, Fisher's LSD test); mean±SEM, n=6-7. BMP-9 restores the barrier function in lung endothelial cells: BMP-9 reduces the LPS-induced migration of leucocytes into the lung in an in vivo mouse sepsis model (100 ng BMP-9 1 hour prior to 5 mg LPS/kg i.p., BAL 48 h post LPS).

As described previously, all tests are performed using BMP-9 as a reference, since BMP-9 is the natural activator of ALK-1/BMPR-2 signaling. Using the following description of the method, BMP 9 reduced the number of white blood cells infiltrating the lung in a mouse sepsis model. (FIG. 6).

Male BALB/cAnN mice (Charles River Laboratories, Sulzfeld, Germany) in the age of 6-8 weeks weighing 18-22 g are anesthetized in a chamber with isoflurane (5% v/v). 1 h prior to an intraperitoneal injection of 5 mg/kg LPS to induce systemic inflammation (sepsis), the animals receive intraperitoneal injections of BsABS, 100 ng/animal BMP 9, or vehicle. Control animals remain untreated. Due to the known half-life of BMP 9, animals treated with BMP 9 receive another 100 ng/animal 24 h and 48 h after the first application. Those animals receiving vehicle get also daily vehicle injections. Dependent on the pharmacokinetic profile of BsABs, the animal receive further or no further injections of BsABs 24 and/or 48 hours after the first injection. If the first injection of BsABs leads to efficient levels over the whole study, the animals receive vehicle instead. 48 hours after the application of LPS, respectively 1 hour after the last injection of BMP 9, vehicle, or BsAB/vehicle, the mice are sacrificed by deep anesthesia with ketamine/rompun (200 mg/kg and 20 mg/kg i.p.) and final bleeding. The tracheas are cannulated and the lungs of the animals are lavaged (broncho-alveolar lavage fluid, BALF) three times, each time with 0.5 ml ice-cold 0.9% saline. The number of white blood cells in the BALF is counted automatically in a cell counter or FACS device. The total protein content of the BALF is determined using photometric standard protocols. BsABs reducing the invasion of white blood cells or leakage of proteins into the lung in a BMP 9-like manner are considered as BsABs with potent agonistic effect on ALK-1/BMPR-2 signaling.

Example 9 Evaluation of Agonistic Activity In Vivo

Determination of the BsABs Activity on ALK-1/BMPR-2 Signaling in Monocrotaline-Induced Pulmonary Hypertension in Rats Adult male Sprague-Dawley rats weighing 250 to 280 g are purchased from Charles River Laboratories (Sulzfeld, Germany). Rats receive a single subcutaneous injection of 60 mg/kg MCT (Sigma-Aldrich Chemie GmbH, M ünchen, Germany) under isoflurane anesthesia (2% v/v). Therefore, MCT is dissolved in 1 M aqueous HCl, diluted with physiologic saline and neutralized to pH 7.4 with 1 M aqueous NaOH to reach a final injection volume of 0.5 ml per rat. Fourteen days after the MCT injection, the animals are randomized to be treated with either BsABs, or BMP-9, or vehicle for 14 days until the day of the final hemodynamic analysis on day 28. Control animals remain untreated. Due to the known half-life of BMP-9, animals receive intraperitoneal injections of 750 ng/animal daily. Those animals receiving vehicle get also daily vehicle injections. The animals treated with BsABs receive injections according to their pharmacokinetic profile (see above). If the required frequency of BsAB injections is lower than daily, the animals receive vehicle instead to ensure that the number of injections is identical in each treatment group. On day 28 after the injection of MCT, the rats are anesthetized with pentobarbital (60 mg/kg i.p.). After tracheotomy, anesthesia is maintained by inhalation of isoflurane (1.8% v/v) under conditions of artificial ventilation. $FiO_2$ is set at 0.5, respiration volume to 10 ml/kg at 60 strokes/min, inspiration to expiration ratio to 1:1, and the positive end-expiratory pressure to 1.0 cm $H_2O$. Core body temperature is maintained at 37° C. using a controlled heating pad. A Millar microtip catheter is inserted into the left carotid artery to measure heart rate and systemic arterial pressure. A fluid filled polyethylene catheter is inserted through the right jugular vein into the right ventricle for measurement of right ventricular pressure. All hemodynamic measurements were performed with a PowerLab System using the Chart 5.0 Software. EDTA plasma samples were taken for plasma proBNP measurement. After final bleeding of the animals, the right and the left ventricles, the latter including the septum are weighed to calculate the ratio of the right to the left ventricular mass to determine right ventricular hypertrophy. BsABs reducing the right ventricular pressure, respectively the right ventricular hypertrophy and/or plasma proBNP levels in a BMP-9-like manner are considered as BsABs with potent agonistic effect on ALK-1/BMPR-2 signaling.

Example 10 Evaluation of Agonistic Activity In Vivo

Determination of the BsABs Activity on ALK-1/BMPR-2 Signaling in Sugen/Hypoxia-Induced Pulmonary Hypertension in Rats Adult male Dahl/SS rats weighing 160 to 180 g are purchased from Charles River Laboratories (Sulzfeld, Germany). Rats receive a single subcutaneous injection of 20 mg/kg of the VEGFR-Inhibitor SU5416 under isoflurane anesthesia (2% v/v) Immediately after the injection, the animals are housed under hypoxic conditions (10% $O_2$) for the following four weeks and under normoxic conditions for another two weeks. Fourteen days after the SU5416 injection, the animals are randomized to be treated with either BsABs, or BMP-9, or vehicle for 28 days until the day of the final hemodynamic analysis on day 42. Control animals remain untreated. Due to the known half-life of BMP-9, animals receive intraperitoneal injections of 750 ng/animal daily. Those animals receiving vehicle get also daily vehicle injections. The animals treated with BsABs receive injections according to their pharmacokinetic profile (see above). If the required frequency of BsAB injections is lower than daily, the animals receive vehicle instead to ensure that the number of injections is identical in each treatment group. On day 42, the rats are anesthetized with pentobarbital (60 mg/kg i.p.). After tracheotomy, anesthesia is maintained by inhalation of isoflurane (1.8% v/v) under conditions of artificial ventilation. $FiO_2$ is set at 0.5, respiration volume to 10 ml/kg at 60 strokes/min, inspiration to expiration ratio to 1:1, and the positive end-expiratory pressure to 1.0 cm $H_2O$. Core body temperature is maintained at 37 C using a controlled heating pad. A Millar microtip catheter is inserted into the left carotid artery to measure heart rate and systemic arterial pressure. A fluid filled polyethylene catheter is inserted through the right jugular vein into the right ventricle for measurement of the right ventricular pressure. All hemodynamic measurements are performed with a PowerLab System using the Chart 5.0 Software. EDTA plasma samples were taken for plasma proBNP measurement. After final bleeding of the animals, the right and the left ventricles, the latter including the septum are weighed to calculate the ratio of the right to the left ventricular mass to determine right ventricular hypertrophy. BsABs reducing the right ventricular pressure and/or the right ventricular hypertrophy, and/or plasma proBNP levels in a BMP-9-like manner are considered as potent BsABs.

Example 11 Evaluation of ALK-1/BMPR-2 Specificity of BsAbs

Figure 9:
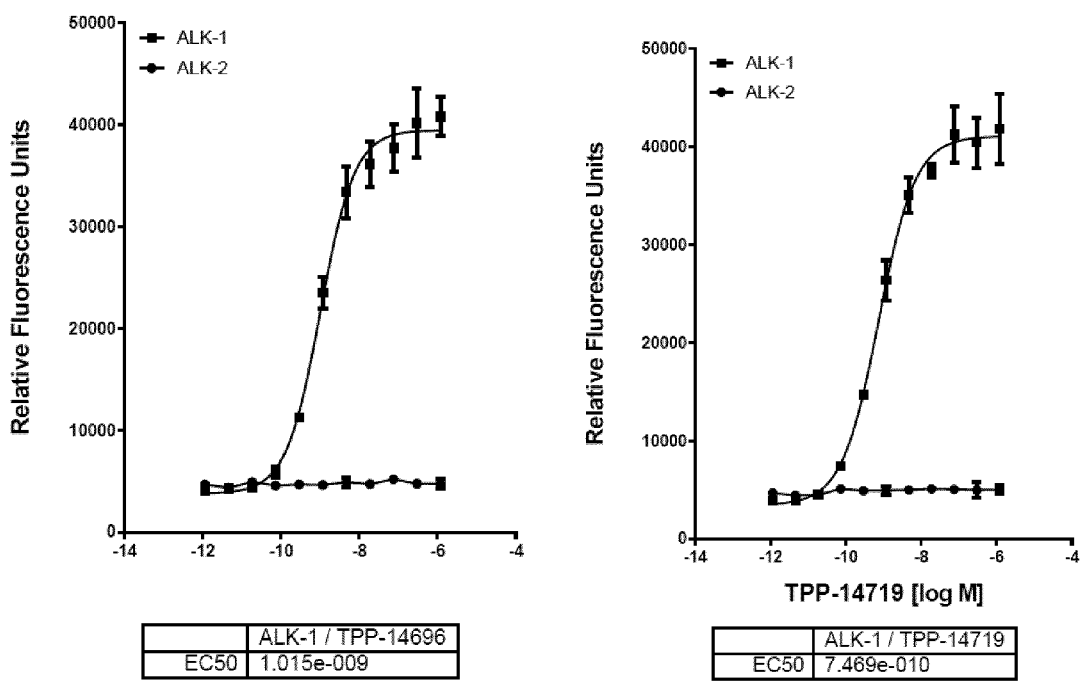
FIG. 9 shows selectivity data for the ALK-1/BMPR-2 receptor complex compared to the ALK-2/BMPR-2 receptor wherein the specificity of the agonistic antibodies has been evaluated by ELISA. Antigens human ALK-1-Fc and human ALK-2-Fc were coated at 2 µg/ml and binding of TPP-14696 and TPP-14719 was detected by anti-human IgG2 (Fc specific) antibody (Sigma 19513) followed by anti-mouse IgG (whole molecule)-HRP (Sigma A9044, 1:40000).

In order to determine the selectivity for the ALK-1/BMPR-2 receptor complex compared to the ALK-2/BMPR-2 receptor, the specificity of the agonistic antibodies has been evaluated by ELISA (FIG. 9). The antigens human ALK-1-Fc and human ALK-2-Fc were coated at 2 µg/ml and binding of TPP-14696 and TPP-14719 was detected by anti-human IgG2 (Fc specific) antibody (Sigma 19513) followed by anti-mouse IgG (whole molecule)—HRP (Sigma A9044, 1:40000).

Example 12 Evaluation of Osteogenic Activity of BsAbs

For testing potential osteogenic activity of agonistic molecules, the mouse myoblast cell line C2C12 (ATCC, catalogue number CRL-1772) is used. For this, the cells are cultured according to the manufacturer's instructions.

For determination of osteogenic activity, cells are seeded in 96-well plates at a cell density of 5000 cells/well. After 24 hours, cells are starved for additional 20 hours in DMEM medium (Invitrogen, catalogue number 61965-059) containing 0.25% of FCS (Invitrogen, catalogue number 10082-147). Following this starvation period, cells are treated with various concentrations of BMP-9 and BsABs, respectively, for 72 hours. Determination of BMP-9 and BsABs-induced alkaline phosphatase (ALP) activity in C2C12 cells treated as described above, the Alkaline Phosphatase Assay Kit (Abcam, catalogue number ab83369) is used. Thereby, sample preparation and determination of ALP activity is performed according to the manufacturer's instructions. Those BsABs showing agonistic activity on the DiscoverX PathHunter cell line as well as on primary endothelial cells but which do not show any activity on the C2C12 cell line are considered as BsABs with potent agonistic activity which is selective for ALK-1/BMPR-2.

The invention claimed is:

1. A bispecific antibody (BsAB), wherein said BsAB comprises an ALK-1 binding domain and a BMPR-2 binding domain, wherein said BsAB promotes dimerization of ALK-1 and BMPR-2, and wherein said BsAB is TPP-14696 comprising the amino acid sequences of SEQ ID NOS: 1, 8, 15, and 22 or TPP-14719 comprising the amino acid sequences of SEQ ID NOS: 29, 36, 43, and 50.

2. A BsAB according to claim 1, wherein the ALK-1 is human ALK-1 or a fragment thereof, and wherein the BMPR-2 is human BMPR-2 or a fragment thereof.

* * * * *